US012703731B2

(12) United States Patent
Gan et al.

(10) Patent No.: US 12,703,731 B2
(45) Date of Patent: Aug. 11, 2026

(54) LONG-ACTING GLP-1 COMPOUND

(71) Applicant: Gan & Lee Pharmaceuticals Co., Ltd., Beijing (CN)

(72) Inventors: Zhongru Gan, Beijing (CN); Wei Chen, Beijing (CN); Yining Zhang, Beijing (CN); Fangkai Xue, Beijing (CN); Lingyu Cai, Beijing (CN); Jianghong Niu, Beijing (CN); Bin Mu, Beijing (CN)

(73) Assignee: Gan & Lee Pharmaceuticals Co., Ltd., Beijing (CN)

( * ) Notice: Subject to any disclaimer, the term of this patent is extended or adjusted under 35 U.S.C. 154(b) by 860 days.

(21) Appl. No.: 17/758,113

(22) PCT Filed: Dec. 29, 2020

(86) PCT No.: PCT/CN2020/141057

§ 371 (c)(1),
(2) Date: Jun. 28, 2022

(87) PCT Pub. No.: WO2021/136303

PCT Pub. Date: Jul. 8, 2021

(65) Prior Publication Data

US 2024/0239859 A1 Jul. 18, 2024

(30) Foreign Application Priority Data

Dec. 30, 2019 (CN) ......................... 201911397405.2
Sep. 29, 2020 (CN) ......................... 202011053306.5

(51) Int. Cl.

| | |
|---|---|
| ***C07K 14/605*** | (2006.01) |
| ***A61K 38/28*** | (2006.01) |
| ***A61K 47/02*** | (2006.01) |
| ***A61K 47/10*** | (2017.01) |
| ***A61P 3/04*** | (2006.01) |
| ***A61P 3/10*** | (2006.01) |

(52) U.S. Cl.
CPC ............ *C07K 14/605* (2013.01); *A61K 38/28* (2013.01); *A61K 47/02* (2013.01); *A61K 47/10* (2013.01); *A61P 3/04* (2018.01); *A61P 3/10* (2018.01)

(58) Field of Classification Search
None
See application file for complete search history.

(56) References Cited

U.S. PATENT DOCUMENTS

| | | | | |
|---|---|---|---|---|
| 8,129,343 | B2 * | 3/2012 | Lau | A61P 25/08 514/11.7 |
| 2007/0203058 | A1 | 8/2007 | Lau et al. | |
| 2009/0156478 | A1 | 6/2009 | Lau et al. | |
| 2010/0292133 | A1 | 11/2010 | Spetzler et al. | |
| 2011/0098439 | A1 | 4/2011 | Madsen et al. | |
| 2011/0098440 | A1 | 4/2011 | Madsen et al. | |
| 2011/0105720 | A1 | 5/2011 | Madsen et al. | |
| 2012/0221865 | A1 * | 8/2012 | Hahn | H04N 21/4331 713/193 |
| 2013/0345134 | A1 | 12/2013 | Sauerberg et al. | |
| 2015/0072926 | A1 | 3/2015 | Vilhelmsen et al. | |
| 2017/0312225 | A1 | 11/2017 | Nielsen et al. | |
| 2021/0236601 | A1 | 8/2021 | Bjerregaard et al. | |
| 2021/0393744 | A1 | 12/2021 | Xu et al. | |
| 2023/0126068 | A1 * | 4/2023 | Gan | A61K 47/02 514/5.9 |
| 2024/0025957 | A1 * | 1/2024 | Gan | A61K 38/28 |
| 2024/0239862 | A1 * | 7/2024 | Gan | A61K 47/02 |
| 2024/0316157 | A1 | 9/2024 | Jiao et al. | |
| 2025/0011385 | A1 * | 1/2025 | Gan | A61K 9/08 |
| 2025/0276043 | A1 | 9/2025 | Zhang et al. | |

FOREIGN PATENT DOCUMENTS

| | | | |
|---|---|---|---|
| CN | 101133082 | A | 2/2008 |
| CN | 101784562 | A | 7/2010 |
| CN | 101784563 | A | 7/2010 |
| CN | 101842386 | A | 9/2010 |
| CN | 102037008 | A | 4/2011 |
| CN | 103260608 | A | 8/2013 |
| CN | 104203266 | A | 12/2014 |
| CN | 109248323 | A | 1/2019 |
| CN | 112153979 | A | 12/2020 |
| WO | 99/43708 | A1 | 9/1999 |
| WO | 00/34331 | A2 | 6/2000 |
| WO | 00/69911 | A1 | 11/2000 |
| WO | 2006097537 | A2 | 9/2006 |
| WO | 2009030771 | A1 | 3/2009 |

(Continued)

OTHER PUBLICATIONS

International Search Report (Form PCT/ISA/210) for International Patent Application No. PCT/CN2020/141057, issued from the International Searching Authority, date of mailing Mar. 25, 2021, 16 pages.
Written Opinion of the International Searching Authority (Form PCT/ISA/237) for International Patent Application No. PCT/CN2020/141057, issued from the International Searching Authority, date of mailing Mar. 25, 2021, 13 pages.
International Preliminary Report on Patentability (Form PCT/IB/373) for International Patent Application No. PCT/CN2020/141057, issued from the International Searching Authority, date of mailing Mar. 25, 2021, 7 pages.
U.S. Appl. No. 17/758,089, entitled “Insulin Derivative,” filed Jun. 28, 2022, 118 pages.

(Continued)

*Primary Examiner* — Sudhakar Katakam
*Assistant Examiner* — Zachary J Miknis
(74) *Attorney, Agent, or Firm* — Ice Miller LLP

(57) ABSTRACT

A novel GLP-1 derivative, compared with GLP-1 derivatives such as liraglutide and semaglutide which are on the market, has comparable or better effect, potency or efficacy, longer or comparable duration of action in vivo or half-life in vivo, has better or comparable GLP-1 receptor binding affinity and has better or comparable DPP-IV stability.

11 Claims, 17 Drawing Sheets

Specification includes a Sequence Listing.

(56) References Cited

FOREIGN PATENT DOCUMENTS

| | | | | |
|---|---|---|---|---|
| WO | WO-2017032798 A1 * | 3/2017 | ................ | A61P 3/10 |
| WO | 2017205191 A1 | 11/2017 | | |
| WO | WO-2018109162 A1 * | 6/2018 | ............. | A61P 43/00 |
| WO | 2019200594 A1 | 10/2019 | | |
| WO | 2021136293 A1 | 7/2021 | | |

OTHER PUBLICATIONS

U.S. Appl. No. 17/758,101, entitled “Insulin Derivative,” filed Jun. 28, 2022, 130 pages.

U.S. Appl. No. 17/758,108, entitled “Insulin Derivative,” filed Jun. 28, 2022, 159 pages.

Lau, Jesper et al. “Discovery of the Once-Weekly Glucagon-Like Peptide-1 (GLP-1) Analogue Semaglutide,” Journal of Medicinal Chemistry, vol. 58 (2015) pp. 7370-7380.

Cheang, Jia Ying et al. “Glucagon-Like Peptide-1 (GLP-1)-Based Therapeutics: Current Status and Future Opportunities beyond Type 2 Diabetes,” ChemMedChem Communications, vol. 13, issue 7 (Apr. 2018) pp. 662-671.

Knudsen, Lotte Bjerre et al. “The Discovery and Development of Liraglutide and Semaglutide,” Frontiers in Endocrinology, vol. 10, article 155 (Apr. 2019) pp. 1-32.

Coskun, Tamer et al. “LY3298176, a novel dual GIP and GLP-1 receptor agonist for the treatment of type 2 diabetes mellitus: From discovery to clinical proof of concept,” Molecular Metabolism, vol. 18 (Dec. 2018) pp. 3-14.

* cited by examiner

*p < 0.05compound 2 compared to semaglutide

Combined male and female mice n = 9–11

Vehicle
Semaglutide-100 μg/kg
Compound 10-100 μg/kg
Compound 10-300 μg/kg
Cumulative water intake (mL)
800
600
400
200
0
0 2 4 6 8 10 12 14 16 18 20 22 24 26 28 30
Time (day)

SEQUENCE LISTING

```
<160> NUMBER OF SEQ ID NOS: 17

<210> SEQ ID NO 1
<211> LENGTH: 31
<212> TYPE: PRT
<213> ORGANISM: Artificial Sequence
<220> FEATURE:
<223> OTHER INFORMATION: GLP-1(7-37) peptide

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 2
<211> LENGTH: 31
<212> TYPE: PRT
<213> ORGANISM: Artificial Sequence
<220> FEATURE:
<223> OTHER INFORMATION: [Gly8, Arg34]GLP-1-(7-37) peptide

<400> SEQUENCE: 2

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30


<210> SEQ ID NO 3
<211> LENGTH: 31
<212> TYPE: PRT
<213> ORGANISM: Artificial Sequence
<220> FEATURE:
<223> OTHER INFORMATION: [Arg34]GLP-1-(7-37) peptide

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30


<210> SEQ ID NO 4
<211> LENGTH: 21
<212> TYPE: PRT
<213> ORGANISM: Artificial Sequence
<220> FEATURE:
<223> OTHER INFORMATION: A chain of desB30 human insulin

<400> SEQUENCE: 4

Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 5
<211> LENGTH: 29
<212> TYPE: PRT
<213> ORGANISM: Artificial Sequence
<220> FEATURE:
<223> OTHER INFORMATION: B chain of desB30 human insulin

<400> SEQUENCE: 5

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25
```

<210> SEQ ID NO 6
<211> LENGTH: 21
<212> TYPE: PRT
<213> ORGANISM: Artificial Sequence
<220> FEATURE:
<223> OTHER INFORMATION: A chain of A14E, B16H, B25H, desB30 human insulin

<400> SEQUENCE: 6

```
Gly Ile Val Glu Gln Cys Cys Thr Ser Ile Cys Ser Leu Glu Gln Leu
1               5                   10                  15

Glu Asn Tyr Cys Asn
            20
```

<210> SEQ ID NO 7
<211> LENGTH: 29
<212> TYPE: PRT
<213> ORGANISM: Artificial Sequence
<220> FEATURE:
<223> OTHER INFORMATION: B chain of A14E, B16H, B25H, desB30 human insulin

<400> SEQUENCE: 7

```
Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25
```

<210> SEQ ID NO 8
<211> LENGTH: 21
<212> TYPE: PRT
<213> ORGANISM: Artificial Sequence
<220> FEATURE:
<223> OTHER INFORMATION: A chain of A14E, B16E, B25H, desB30 human insulin

<400> SEQUENCE: 8

```
Gly Ile Val Glu Gln Cys Cys Thr Ser Ile Cys Ser Leu Glu Gln Leu
1               5                   10                  15

Glu Asn Tyr Cys Asn
            20
```

<210> SEQ ID NO 9
<211> LENGTH: 29
<212> TYPE: PRT
<213> ORGANISM: Artificial Sequence
<220> FEATURE:
<223> OTHER INFORMATION: B chain of A14E, B16E, B25H, desB30 human insulin

<400> SEQUENCE: 9

```
Phe Val Asn Gln His Leu Cys Gly Ser His Leu Val Glu Ala Leu Glu
```

-continued

```
1               5                   10                  15

Leu Val Cys Gly Glu Arg Gly Phe His Tyr Thr Pro Lys
            20                  25


<210> SEQ ID NO 10
<211> LENGTH: 21
<212> TYPE: PRT
<213> ORGANISM: Artificial Sequence
<220> FEATURE:
<223> OTHER INFORMATION: A chain of human insulin

<400> SEQUENCE: 10

Gly Ile Val Glu Gln Cys Cys Thr Ser Ile Cys Ser Leu Tyr Gln Leu
1               5                   10                  15

Glu Asn Tyr Cys Asn
            20


<210> SEQ ID NO 11
<211> LENGTH: 30
<212> TYPE: PRT
<213> ORGANISM: Artificial Sequence
<220> FEATURE:
<223> OTHER INFORMATION: B chain of human insulin

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 12
<211> LENGTH: 21
<212> TYPE: PRT
<213> ORGANISM: Artificial Sequence
<220> FEATURE:
<223> OTHER INFORMATION: A chain of A21G human insulin

<400> SEQUENCE: 12

Gly Ile Val Glu Gln Cys Cys Thr Ser Ile Cys Ser Leu Tyr Gln Leu
1               5                   10                  15

Glu Asn Tyr Cys Gly
            20


<210> SEQ ID NO 13
<211> LENGTH: 30
<212> TYPE: PRT
<213> ORGANISM: Artificial Sequence
<220> FEATURE:
<223> OTHER INFORMATION: B chain of A21G human insulin

<400> SEQUENCE: 13

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 14
<211> LENGTH: 21
<212> TYPE: PRT
<213> ORGANISM: Artificial Sequence
<220> FEATURE:
<223> OTHER INFORMATION: A chain of A21G, desB30 human insulin

<400> SEQUENCE: 14
```

-continued

```
Gly Ile Val Glu Gln Cys Cys Thr Ser Ile Cys Ser Leu Tyr Gln Leu
1               5                   10                  15

Glu Asn Tyr Cys Gly
            20


<210> SEQ ID NO 15
<211> LENGTH: 29
<212> TYPE: PRT
<213> ORGANISM: Artificial Sequence
<220> FEATURE:
<223> OTHER INFORMATION: B chain of A21G, desB30 human insulin

<400> SEQUENCE: 15

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25


<210> SEQ ID NO 16
<211> LENGTH: 21
<212> TYPE: PRT
<213> ORGANISM: Artificial Sequence
<220> FEATURE:
<223> OTHER INFORMATION: A chain of B28D human insulin

<400> SEQUENCE: 16

Gly Ile Val Glu Gln Cys Cys Thr Ser Ile Cys Ser Leu Tyr Gln Leu
1               5                   10                  15

Glu Asn Tyr Cys Asn
            20


<210> SEQ ID NO 17
<211> LENGTH: 30
<212> TYPE: PRT
<213> ORGANISM: Artificial Sequence
<220> FEATURE:
<223> OTHER INFORMATION: B chain of B28D human insulin

<400> SEQUENCE: 17

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30
```

LONG-ACTING GLP-1 COMPOUND

CROSS-REFERENCE TO RELATED APPLICATIONS

This application is a Section 371 of International Application No. PCT/CN2020/141057, filed on Dec. 29, 2020, which published in the Chinese language on Jul. 8, 2021, under International Publication No. WO 2021/136303 A1 that claims priority to Chinese Patent Application No. CN 201911397405.2 filed on Dec. 30, 2019, and to Chinese Patent Application No. CN 202011053306.5 filed on Sep. 29, 2020. Each disclosure is incorporated herein by reference in its entirety.

REFERENCE TO SEQUENCE LISTING SUBMITTED ELECTRONICALLY

This application contains a sequence listing that is submitted electronically via EFS-Web as an ASCII formatted sequence listing with a file name "063038_7US1 Substitute Sequence Listing" and a creation date of Aug. 29, 2022, and having a size of 6.11 kb. The sequence listing, submitted via EFS-Web, is part of the specification and is herein incorporated by reference in its entirety.

TECHNICAL FIELD

The present invention relates to the field of therapeutic peptides, in particular to a novel long-acting GLP-1 compound, a pharmaceutical formulation thereof, a pharmaceutical composition thereof with a long-acting insulin, and medical use of the compound, the pharmaceutical formulation and the pharmaceutical composition.

BACKGROUND

Glucagon-like peptide 1 (GLP-1) and its analogues and derivatives are very effective in treating type 1 and type 2 diabetes, but their effectiveness is limited due to high clearance. In order to provide GLP-1 compounds that have a longer duration of action in vivo, a series of different methods have been used to modify the structure of glucagon-like peptide 1 (GLP-1). For example, WO99/43708 discloses GLP-1(7-35) and GLP-1(7-36) derivatives with a lipophilic substituent linked to a C-terminal amino acid residue. WO00/34331 discloses acylated GLP-1 analogues. WO00/69911 discloses activated insulinotropic peptides for injection into patients.

Currently marketed GLP-1 drugs include, for example, exenatide as a natural GLP-1 analogue administered twice daily; liraglutide and lixisenatide administered once daily, wherein liraglutide is a GLP-1 compound modified by hexadecanoic acid, and lixisenatide is a new molecule obtained by modifying the structure of exenatide; and semaglutide, exenatideLAR, abiglutide, dulaglutide and PEG-Loxenatide administered once a week. Among those drugs, exenatideLAR is prepared by encapsulating exenatide in a poly(lactic-co-glycolic acid) matrix by a microencapsulation method, and abiglutide is a recombinant fusion protein formed by fusing two modified GLP-1 peptide chains with human albumin in a dimer form; dulaglutide is obtained by fusing a modified GLP-1 chain to an Fc fragment of recombinant G4 immunoglobulin through disulfide bonds; PEG-Loxenatide is formed by engineering of amino acids and modification with polyethylene glycol on the basis of the chemical structural formula of exenatide; for semaglutide, administering once a week is mainly achieved by replacing Ala at position 8 with non-proteinogenic amino acid Aib on GLP-1(7-37) peptide, but the presence of the non-proteinogenic amino acid in semaglutide may result in a risk of developing a variety of unknown and potential side effects in humans relative to the natural amino acids.

On the one hand, there is still a need to develop compounds that have better potency, drug effect or efficacy, less risk of developing potential side effects, better weight loss and diet suppression effects, longer or comparable duration of action or half-life in vivo relative to the marketed similar drugs such as liraglutide, dulaglutide and semaglutide, to provide better medication options for diabetic patients.

On the other hand, with the rapid increase in the population with type 2 diabetes worldwide, there is a greater need for more effective drugs that are easier to administer. For example, a compound formulation comprising two active ingredients, insulin and a GLP-1 peptide, may be a very effective therapeutic agent. Therefore, at present, there is still a need for a compound formulation which can synergistically achieve better physical and chemical stability, longer duration of action and better drug effect.

SUMMARY

In order to overcome or improve at least one of the defects of the prior art, or to provide a useful alternative, a novel GLP-1 compound (also known as a GLP-1 derivative) is provided in a first aspect of the present invention. The novel GLP-1 compounds have better potency, drug effect or efficacy, smaller risks of developing potential side effects, better effect of weight loss, longer duration of action or half-life in vivo, better or comparable binding affinity for a GLP-1 receptor and better or comparable DPP-IV stability compared to the marketed GLP-1 derivatives such as liraglutide, dulaglutide and semaglutide. In addition, the pharmaceutical composition or the combo formulation of a long-acting GLP-1 compound disclosed herein and a long-acting insulin provided herein does not impair the physical stability of the GLP-1 compound and the insulin compound; instead, the combo formulation has better physical stability than the mono formulation. The physical stability of the combo formulation disclosed herein is beyond expectation compared to combo formulations of other long-acting GLP-1 compounds, e.g., the combo formulation of liraglutide and insulin degludec. Furthermore, the combo formulation also allows for an increase in the chemical stability of the GLP-1 compounds and the acylated insulin compared to the mono formulation. Both the GLP-1 compound disclose herein and the combo formulation comprising the GLP-1 compound and the insulin compounds provided herein are well capable of achieving a long pharmacokinetic (hereinafter also referred to as PK) profile, thus enabling subcutaneous treatment of diabetic patients twice a week, once a week, once every two weeks, or less frequently.

In a first aspect of the present invention, provided is a GLP-1 compound of formula B, or a pharmaceutically acceptable salt, amide or ester thereof:

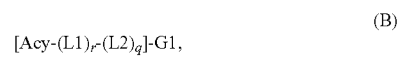

$$[Acy\text{-}(L1)_r\text{-}(L2)_q]\text{-}G1, \quad (B)$$

wherein G1 is a GLP-1 analogue having Arg at position 34 and Ala or Gly at position 8 of GLP-1(7-37) (SEQ ID NO: 1), and $[Acy\text{-}(L1)_r\text{-}(L2)_q]$ is a substituent linked to an ε amino group of the Lys residue at position 26 of the GLP-1 analogue, wherein r is an integer from 1 to 10, and q is 0 or an integer from 1 to 10;

Acy is a fatty diacid comprising 20-24 carbon atoms, wherein formally, a hydroxyl group has been removed from one of carboxyl groups in the fatty diacid;

L1 is an amino acid residue selected from the following: γGlu, αGlu, βAsp, αAsp, γ-D-Glu, α-D-Glu, β-D-Asp and α-D-Asp;

L2 is a neutral and alkylene glycol-containing amino acid residue;

Acy, L1 and L2 are linked by amide bonds; and an order of occurrence of L1 and L2 in the formula (B) can be independently interchanged.

In one embodiment, G1 is [Gly8, Arg34]GLP-1-(7-37) peptide or [Arg34]GLP-1-(7-37) peptide, preferably [Gly8, Arg34]GLP-1-(7-37) peptide.

In one embodiment, r is 1, 2, 3, 4, 5 or 6; preferably, r is 1, 2, 3 or 4; preferably, r is 1 or 2; preferably, r is 1.

In another embodiment, q is 0, 1, 2, 3, 4, 5, 6, 7 or 8; preferably, q is 0, 1, 2, 3 or 4; more preferably, q is 0, 1, or 2.

In one embodiment, Acy is a fatty diacid containing 20-23 carbon atoms; preferably, Acy is a fatty diacid containing 20, 21 or 22 carbon atoms, wherein formally, the hydroxyl group has been removed from one of the carboxyl groups in the fatty diacid.

In one embodiment, L2 is $—HN—(CH_2)_2—O—(CH_2)_2—O—CH_2—CO—$, $—HN—(CH_2)_2—O—(CH_2)_2—O—(CH_2)_2—O—(CH_2)_2—O—(CH_2)_2—CO—$, $—HN—(CH_2)_2—O—(CH_2)_2—O—(CH_2)_2—O—(CH_2)_2—O—(CH_2)_2—O—(CH_2)_2—O—(CH_2)_2—CO—$, $—HN—(CH_2)_2—O—(CH_2)_2—O—(CH_2)_2—O—(CH_2)_2—O—(CH_2)_2—O—(CH_2)_2—O—(CH_2)_2—O—(CH_2)_2—O—(CH_2)_2—CO—$, $—HN—(CH_2)_3—O—(CH_2)_4—O—(CH_2)_3—NH—CO—$, $—HN—(CH_2)_3—O—(CH_2)_4—O—(CH_2)_3—NH—CO—CH_2—O—CH_2—CO—$, $—HN—(CH_2)_3—O—(CH_2)_4—O—(CH_2)_3—NH—CO—(CH_2)_2—CO—$, $—HN—(CH_2)_2—O—(CH_2)_2—O—CH_2—CO—CH_2—O—CH_2—CO—$, $—HN—(CH_2)_3—O—(CH_2)_2—O—(CH_2)_2—O—(CH_2)_3—NH—CO—(CH_2)_2—CO—$, $—HN—(CH_2)_3—O—(CH_2)_2—O—(CH_2)_2—O—(CH_2)_3—NH—CO—CH_2—O—CH_2—CO—$, $—HN—(CH_2)_2—O—(CH_2)_2—O—(CH_2)_2—NH—CO—(CH_2)_2—CO—$, $—HN—(CH_2)_2—O—(CH_2)_2—O—(CH_2)_2—NH—CO—CH_2—O—CH_2—CO—$, $—HN—(CH_2)_3—O—(CH_2)_2—O—(CH_2)_2—O—(CH_2)_3—NH—CO—CH_2—O—CH_2—CO—$, $—HN—(CH_2)_3—O—(CH_2)_3—O—CH_2—CO—$, or $—HN—(CH_2)_4—O—(CH_2)_4—O—CH_2—CO—$; preferably, L2 is $—HN—(CH_2)_2—O—(CH_2)_2—O—CH_2—CO—$.

In one embodiment, L1 is selected from γGlu and βAsp; preferably, L1 is γGlu.

In one embodiment, Acy is $HOOC—(CH_2)_{18}—CO—$, $HOOC—(CH_2)_{19}—CO—$, $HOOC—(CH_2)_{20}—CO—$, $HOOC—(CH_2)_{21}—CO—$ or $HOOC—(CH_2)_{22}—CO—$; preferably, Acy is $HOOC—(CH_2)_{18}—CO—$, $HOOC—(CH_2)_{20}—CO—$ or $HOOC—(CH_2)_{22}—CO—$.

In one embodiment, the Acy, L1 and L2 in formula (B) are sequentially linked by amide bonds, and the C-terminus of L2 is linked to the ε amino group of the Lys residue at position 26 of the GLP-1 analogue.

In one embodiment, the compound according to the first aspect of the present invention is selected from the following group consisting of:

N-$ε^{26}$-[2-(2-[2-(2-[2-(2-[4-(19-carboxynonadecanoylamino)-4(S)-carboxybutanoylamino]ethoxy)ethoxy]acetylamino)ethoxy]ethoxy)acetyl][Gly8, Arg34]GLP-1-(7-37) peptide, N-$ε^{26}$-[2-(2-[2-(4-[19-carboxynonadecanoylamino]-4(S)-carboxybutanoylamino)ethoxy]ethoxy)acetyl][Gly8, Arg34]GLP-1-(7-37) peptide, N-$ε^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide, N-$ε^{26}$-[2-(2-[2-(4-[21-carboxyheneicosanoylamino]-4(S)-carboxybutanoylamino)ethoxy]ethoxy)acetyl][Gly8, Arg34]GLP-1-(7-37) peptide, N-$ε^{26}$-[2-(2-[2-(2-[2-(2-[4-(23-carboxytricosanoylamino)-4(S)-carboxybutanoylamino]ethoxy)ethoxy]acetylamino)ethoxy]ethoxy)acetyl][Gly8, Arg34]GLP-1-(7-37) peptide, N-$ε^{26}$-[2-(2-[2-(4-[23-carboxytricosanoylamino]-4(S)-carboxybutanoylamino) ethoxy]ethoxy)acetyl][Gly8, Arg34]GLP-1-(7-37) peptide, N-$ε^{26}$-(23-carboxytricosanoylamino)-4(S)-carboxybutanoyl-[Gly8, Arg34]GLP-1-(7-37) peptide, N-$ε^{26}$-(19-carboxynonadecanoylamino)-4(S)-carboxybutanoyl-[Gly8, Arg34]GLP-1-(7-37) peptide, N-$ε^{26}$-(21-carboxyheneicosanoylamino)-4(S)-carboxybutanoyl-[Gly8, Arg34]GLP-1-(7-37) peptide, N-$ε^{26}$-[2-(2-[2-(2-[2-(2-[4-(19-carboxynonadecanoylamino)-4(S)-carboxybutanoylamino]ethoxy)ethoxy]acetylamino)ethoxy]ethoxy)acetyl][Arg34]GLP-1-(7-37) peptide, N-$ε^{26}$-[2-(2-[2-(4-[19-carboxynonadecanoylamino]-4(S)-carboxybutanoylamino)ethoxy]ethoxy)acetyl][Arg34]GLP-1-(7-37) peptide, N-$ε^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Arg34]GLP-1-(7-37) peptide, N-$ε^{26}$-[2-(2-[2-(4-[21-carboxyheneicosanoylamino]-4(S)-carboxybutanoylamino)ethoxy]ethoxy)acetyl][Arg34]GLP-1-(7-37) peptide, N-$ε^{26}$-[2-(2-[2-(2-[2-(2-[4-(23-carboxytricosanoylamino)-4(S)-carboxybutanoylamino]ethoxy)ethoxy]acetylamino)ethoxy]ethoxy)acetyl][Arg34]GLP-1-(7-37) peptide, N-$ε^{26}$-[2-(2-[2-(4-[23-carboxytricosanoylamino]-4(S)-carboxybutanoylamino) ethoxy]ethoxy)acetyl][Arg34]GLP-1-(7-37) peptide, N-$ε^{26}$-(23-carboxytricosanoylamino)-4(S)-carboxybutanoyl-[Arg34]GLP-1-(7-37) peptide, N-$ε^{26}$-(19-carboxynonadecanoylamino)-4(S)-carboxybutanoyl-[Arg34]GLP-1-(7-37) peptide, and N-$ε^{26}$-(21-carboxyheneicosanoylamino)-4(S)-carboxybutanoyl-[Arg34]GLP-1-(7-37) peptide.

In one embodiment, the compound according to the first aspect of the present invention is selected from the following group consisting of:

N-$ε^{26}$-[2-(2-[2-(2-[2-(2-[4-(19-carboxynonadecanoylamino)-4(S)-carboxybutanoylamino]ethoxy)ethoxy]acetylamino)ethoxy]ethoxy)acetyl][Gly8, Arg34]GLP-1-(7-37) peptide, N-$ε^{26}$-[2-(2-[2-(4-[19-carboxynonadecanoylamino]-4(S)-carboxybutanoylamino)ethoxy]ethoxy)acetyl][Gly8, Arg34]GLP-1-(7-37) peptide, N-$ε^{26}$-(19-carboxynonadecanoylamino)-4(S)-carboxybutanoyl-[Gly8, Arg34]GLP-1-(7-37) peptide, N-$ε^{26}$-(19-carboxynonadecanoylamino)-4(S)-carboxybutanoyl-[Arg34]GLP-1-(7-37) peptide, N-ε$^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide, N-ε$^{26}$-[2-(2-[2-(4-[21-carboxyheneicosanoylamino]-4(S)-carboxybutanoylamino)ethoxy]ethoxy)acetyl][Gly8, Arg34]GLP-1-(7-37) peptide, N-ε$^{26}$-[2-(2-[2-(2-[2-(2-[4-(20-carboxyeicosanoylamino)-4(S)-carboxybutanoylamino]ethoxy)ethoxy]acetylamino)ethoxy]ethoxy)acetyl][Gly8, Arg34]GLP-1-(7-37) peptide, N-ε$^{26}$-[2-(2-[2-(4-[20-carboxyeicosanoylamino]-4(S)-carboxybutanoylamino)ethoxy]ethoxy)acetyl][Gly8, Arg34]GLP-1-(7-37) peptide, N-ε$^{26}$-[2-(2-[2-(2-[2-(2-[4-(22-carboxydocosanoylamino-4(S)-carboxybutanoylamino]ethoxy)ethoxy]acetylamino)ethoxy]ethoxy)acetyl][Gly8, Arg34]GLP-1-(7-37) peptide, N-ε$^{26}$-[2-(2-[2-(4-[22-carboxydocosanoylamino]-4(S)-carboxybutanoylamino)ethoxy]ethoxy)acetyl][Gly8, Arg34]GLP-1-(7-37) peptide, N-ε$^{26}$-(20-carboxyeicosanoylamino)-4(S)-carboxybutanoyl-[Gly8, Arg34]GLP-1-(7-37) peptide, N-ε$^{26}$-(22-carboxydocosanoylamino)-4(S)-carboxybutanoyl-[Gly8, Arg34]GLP-1-(7-37) peptide, N-ε$^{26}$-[2-(2-[2-(2-[2-(2-[4-(20-carboxyeicosanoylamino)-4(S)-carboxybutanoylamino]ethoxy)ethoxy]acetylamino)ethoxy]ethoxy)acetyl][Arg34]GLP-1-(7-37) peptide, -N-ε$^{26}$-[2-(2-[2-(4-[20-carboxyeicosanoylamino]-4(S)-carboxybutanoylamino)ethoxy]ethoxy)acetyl][Arg34]GLP-1-(7-37) peptide, N-ε$^{26}$-[2-(2-[2-(2-[2-(2-[4-(22-carboxydocosanoylamino)-4(S)-carboxybutanoylamino]ethoxy)ethoxy]acetylamino)ethoxy]ethoxy)acetyl][Arg34]GLP-1-(7-37) peptide, N-ε$^{26}$-[2-(2-[2-(4-[22-carboxydocosanoylamino]-4(S)-carboxybutanoylamino) ethoxy]ethoxy)acetyl][Arg34]GLP-1-(7-37) peptide, N-ε$^{26}$-(20-carboxyeicosanoylamino)-4(S)-carboxybutanoyl-[Arg34]GLP-1-(7-37) peptide, and N-ε$^{26}$-(22-carboxydocosanoylamino)-4(S)-carboxybutanoyl-[Arg34]GLP-1-(7-37) peptide.

In one embodiment, the compound according to the first aspect of the present invention is selected from the following group consisting of:

N-ε$^{26}$-[2-(2-[2-(4-[19-carboxynonadecanoylamino]-4(S)-carboxybutanoylamino)ethoxy]ethoxy)acetyl][Gly8, Arg34]GLP-1-(7-37) peptide and N-ε$^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide.

In a second aspect, the present invention provides a pharmaceutical formulation comprising the compound according to the first aspect of the present invention and a pharmaceutically acceptable excipient.

In one embodiment, the pharmaceutically acceptable excipient is selected from one or more of a buffer, a preservative, an isotonic agent, a stabilizer and a chelating agent.

In another embodiment, the pharmaceutically acceptable excipient is a buffer, a preservative and an isotonic agent.

In one embodiment, the pharmaceutical formulation comprises the compound according to the first aspect of the present invention, an isotonic agent, a preservative and a buffer. Preferably, in the pharmaceutical formulation, the compound according to the first aspect of the present invention is N-ε$^{26}$-[2-(2-[2-(4-[19-carboxynonadecanoylamino]-4(S)-carboxybutanoylamino)ethoxy]ethoxy)acetyl][Gly8, Arg34]GLP-1-(7-37) peptide or N-ε$^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide.

In one embodiment, the isotonic agent is selected from one or more of sodium chloride, propylene glycol, mannitol, sorbitol, glycerol, glucose and xylitol; preferably, the isotonic agent is propylene glycol, mannitol or sodium chloride.

In another embodiment, the preservative is selected from one or more of phenol, m-cresol, methyl p-hydroxybenzoate, propyl p-hydroxybenzoate, 2-phenoxyethanol, butyl p-hydroxybenzoate, 2-phenylethanol and benzyl alcohol; preferably, the preservative is phenol or m-cresol.

In another embodiment, the buffer is selected from one or more of sodium acetate, sodium carbonate, citrate, glycylglycine, histidine, glycine, lysine, arginine, sodium dihydrogen phosphate, disodium hydrogen phosphate, sodium phosphate and tris(hydroxymethyl)-aminomethane; preferably, the buffer is sodium acetate, citrate, sodium dihydrogen phosphate or disodium hydrogen phosphate.

In one embodiment, the formulation has a pH value from about 6.0 to about 10.0, preferably from about 6.5 to about 10.0, preferably from about 6.5 to about 9.5, preferably from about 6.5 to about 8.5, more preferably from about 7.0 to about 8.5, more preferably from about 7.0 to about 8.1, even more preferably from about 7.3 to about 8.1.

In one embodiment, the pharmaceutical formulation comprises the following ingredients:

about 0.1-1.2 mM, preferably about 0.2-1 mM, preferably about 0.3-0.7 mM, more preferably about 0.48-0.6 mM, compound according to the first aspect of the present invention;

about 10-1500 mM, preferably about 13-800 mM, preferably about 65-400 mM, preferably about 90-240 mM, preferably about 150-250 mM, preferably about 180-200 mM, more preferably about 183-195 mM, isotonic agent; wherein preferably, the isotonic agent is selected from one or more of propylene glycol, glycerol, mannitol and sodium chloride;

about 1-200 mM, preferably about 5-150 mM, preferably about 10-100 mM, preferably about 20-85 mM, preferably about 30-75 mM, preferably about 45-60 mM, more preferably about 50-60 mM, preservative; wherein preferably, the preservative is selected from one or more of phenol and m-cresol;

about 3-35 mM, preferably about 5-20 mM, more preferably about 5-15 mM, more preferably about 7-10 mM, buffer; wherein the buffer is selected from one or more of sodium acetate, citrate, sodium dihydrogen phosphate and disodium hydrogen phosphate; and the pharmaceutical formulation has a pH value from about 6.0 to about 10.0, preferably from about 6.5 to about 9.5, preferably from about 6.5 to about 8.5, more preferably from about 7.0 to about 8.5, more preferably from about 7.0 to about 8.1, even more preferably from about 7.3 to about 8.1.

In another embodiment, the pharmaceutical formulation comprises: about 0.3-0.7 mM, preferably about 0.48-0.6 mM, N-ε$^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide or N-ε$^{26}$-[2-(2-[2-(4-[19-carboxynonadecanoylamino]-4(S)-carboxybutanoylamino)ethoxy]ethoxy)acetyl][Gly8, Arg34]GLP-1-(7-37) peptide; about 180-200 mM, preferably about 183-195 mM, propylene glycol; about 45-60 mM, preferably about 50-60 mM, phenol; about 5-15 mM buffer, preferably about 7-10 mM disodium hydrogen phosphate; and the pharmaceutical formulation has a pH value from about 6.5 to about 8.5, preferably from about 7.0 to about 8.5, more preferably from about 7.3 to about 8.3.

In another embodiment, the pharmaceutical formulation comprises: about 0.5 mM N-$\varepsilon^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide or N-$\varepsilon^{26}$-[2-(2-[2-(4-[19-carboxynonadecanoylamino]-4(S)-carboxybutanoylamino)ethoxy]ethoxy)acetyl][Gly8, Arg34]GLP-1-(7-37) peptide; about 184 mM propylene glycol; about 58.5 mM phenol; about 10 mM disodium hydrogen phosphate; and the pharmaceutical formulation has a pH value from about 6.5 to about 8.5, preferably from about 7.0 to about 8.5, more preferably from about 7.0 to about 8.1, even more preferably from about 7.3 to about 8.1.

In another embodiment, the pharmaceutical formulation comprises: about 2.0 mg/mL N-$\varepsilon^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide or N-$\varepsilon^{26}$-[2-(2-[2-(4-[19-carboxynonadecanoylamino]-4(S)-carboxybutanoylamino)ethoxy]ethoxy) acetyl][Gly8, Arg34]GLP-1-(7-37) peptide; about 14 mg/mL propylene glycol; about 5.5 mg/mL phenol; about 1.42 mg/mL disodium hydrogen phosphate; and the pharmaceutical formulation has a pH value from about 6.5 to about 8.5, preferably from about 7.0 to about 8.5, more preferably from about 7.0 to about 8.1, even more preferably from about 7.3 to about 8.1.

In a third aspect, the present invention provides a pharmaceutical composition comprising a GLP-1 compound according to the first aspect of the present invention, and an acylated insulin.

In one embodiment, the acylated insulin is B29K(N(ε)-docosanedioyl-γGlu-OEG), desB30 human insulin; A14E, B16H, B25H, B29K(N(ε)-eicosanedioyl-γGlu-2×OEG), desB30 human insulin; or B29K(N(ε)-docosanedioyl-γGlu-12×PEG), desB30 human insulin.

In one embodiment, the acylated insulin is an insulin in which: an insulin parent is a natural insulin or insulin analogue and comprises at least one lysine residue, and an acyl moiety is linked to an amino group of the lysine residue or the N-terminal amino acid residue of the insulin parent, wherein the acyl moiety is shown as formula (A):

III-$(II)_m$-$(I)_n$-(A), wherein m is 0 or an integer from 1 to 10, and n is an integer from 5 to 20; I is a neutral and alkylene glycol-containing amino acid residue; II is an acidic amino acid residue; III is a fatty diacid containing 20-24 carbon atoms, wherein formally, a hydroxyl group has been removed from one of the carboxyl groups in the fatty diacid; III, II and I are linked by amide bonds; and an order of occurrence of II and I in formula (A) can be independently interchanged.

In one embodiment, n is an integer from 5 to 15; preferably, n is 5, 6, 7, 8, 9, 10, 11, 12, 13 or 14; preferably, n is 5, 6, 7, 8, 9, 10, 11 or 12; preferably, n is 5, 6, 7, 8, 9 or 10; preferably, n is 5, 6, 7, 8 or 9; preferably, n is 5, 6, 7 or 8.

In another embodiment, m is an integer from 1 to 6; preferably, m is 1, 2, 3 or 4; preferably, m is 1 or 2; preferably, m is 1.

In yet another embodiment, III is a fatty diacid containing 20-23 carbon atoms; preferably, III is a fatty diacid containing 20, 21 or 22 carbon atoms, wherein formally, a hydroxyl group has been removed from one of the carboxyl groups in the fatty diacid.

In another embodiment, the insulin parent comprises one lysine residue.

In one embodiment, I is $-HN-(CH_2)_2-O-(CH_2)_2-O-CH_2-CO-$, $-HN-(CH_2)_2-O-(CH_2)_2-O-(CH_2)_2-O-(CH_2)_2-O-(CH_2)_2-CO-$, $-HN-(CH_2)_2-O-(CH_2)_2-O-(CH_2)_2-O-(CH_2)_2-O-(CH_2)_2-O-(CH_2)_2-O-(CH_2)_2-CO-$, $-HN-(CH_2)_2-O-(CH_2)_2-O-(CH_2)_2-O-(CH_2)_2-O-(CH_2)_2-O-(CH_2)_2-O-(CH_2)_2-O-(CH_2)_2-O-(CH_2)_2-CO-$, $-HN-(CH_2)_3-O-(CH_2)_4-O-(CH_2)_3-NH-CO-$, $-HN-(CH_2)_3-O-(CH_2)_4-O-(CH_2)_3-NH-CO-CH_2-O-CH_2-CO-$, $-HN-(CH_2)_3-O-(CH_2)_4-O-(CH_2)_3-NH-CO-(CH_2)_2-CO-$, $-HN-(CH_2)_2-O-(CH_2)_2-O-CH_2-CO-CH_2-O-CH_2-CO-$, $-HN-(CH_2)_3-O-(CH_2)_2-O-(CH_2)_2-O-(CH_2)_3-NH-CO-(CH_2)_2-CO-$, $-HN-(CH_2)_3-O-(CH_2)_2-O-(CH_2)_2-O-(CH_2)_3-NH-CO-CH_2-O-CH_2-CO-$, $-HN-(CH_2)_2-O-(CH_2)_2-O-(CH_2)_2-NH-CO-(CH_2)_2-CO-$, $-HN-(CH_2)_2-O-(CH_2)_2-O-(CH_2)_2-NH-CO-CH_2-O-CH_2-CO-$, $-HN-(CH_2)_3-O-(CH_2)_2-O-(CH_2)_2-O-(CH_2)_3-NH-CO-CH_2-O-CH_2-CO-$, $-HN-(CH_2)_3-O-(CH_2)_3-O-CH_2-CO-$, or $-HN-(CH_2)_4-O-(CH_2)_4-O-CH_2-CO-$; preferably, I is $-HN-(CH_2)_2-O-(CH_2)_2-O-CH_2-CO-$.

In another embodiment, II is an amino acid residue selected from the following: γGlu, αGlu, βAsp, αAsp, γ-D-Glu, α-D-Glu, β-D-Asp and α-D-Asp; preferably, II is selected from γGlu and βAsp.

In another embodiment, III is $HOOC-(CH_2)_{18}-CO-$, $HOOC-(CH_2)_{19}-CO-$, $HOOC-(CH_2)_{20}-CO-$, $HOOC-(CH_2)_{21}-CO-$ or $HOOC-(CH_2)_{22}-CO-$; preferably, III is $HOOC-(CH_2)_{18}-CO-$, $HOOC-(CH_2)_{20}-CO-$ or $HOOC-(CH_2)_{22}-CO-$.

In one embodiment, formula (A) is linked to an amino group of the lysine residue or the N-terminal amino acid residue of the insulin parent via the C-terminus of I.

In one embodiment, the acyl moiety is linked to the ε amino group of the lysine residue of the insulin parent.

In one embodiment, the lysine residue of the insulin parent is at position B29.

In one embodiment, the insulin parent is selected from the following group consisting of: desB30 human insulin (SEQ ID NO: 4 and SEQ ID NO: 5, representing A chain and B chain, respectively); A14E, B16H, B25H, desB30 human insulin (SEQ ID NO: 6 and SEQ ID NO: 7, representing A chain and B chain, respectively); A14E, B16E, B25H, desB30 human insulin (SEQ ID NO: 8 and SEQ ID NO: 9, representing A chain and B chain, respectively); human insulin (SEQ ID NO: 10 and SEQ ID NO: 11, representing A chain and B chain, respectively); A21G human insulin (SEQ ID NO: 12 and SEQ ID NO: 13, representing A chain and B chain, respectively); A21G, desB30 human insulin (SEQ ID NO: 14 and SEQ ID NO:15, representing A chain and B chain, respectively); and B28D human insulin (SEQ ID NO: 16 and SEQ ID NO: 17, representing A chain and B chain, respectively).

In one embodiment, the acylated insulin is selected from the following group consisting of: B29K(N(ε)-eicosanedioyl-γGlu-5×OEG), desB30 human insulin; B29K(N(ε)-eicosanedioyl-γGlu-6×OEG), desB30 human insulin; B29K(N(ε)-eicosanedioyl-γGlu-γGlu-5×OEG), desB30 human insulin; B29K(N(ε)-eicosanedioyl-γGlu-γGlu-6×OEG), desB30 human insulin; B29K(N(ε)-eicosanedioyl-5×OEG-γGlu), desB30 human insulin; B29K(N(ε)-eicosanedioyl-6×OEG-γGlu), desB30 human insulin; B29K(N(ε)-eicosanedioyl-6×OEG-γGlu-γGlu), desB30 human insulin; B29K(N (ε)-eicosanedioyl-5×OEG-γGlu-γGlu), desB30 human insulin; B29K(N(ε)-eicosanedioyl-βAsp-5×OEG), desB30 human insulin; B29K(N(ε)-eicosanedioyl-βAsp-6×OEG), desB30 human insulin; B29K(N(ε)-eicosanedioyl-αGlu-5×OEG), desB30 human insulin; B29K(N(ε)-eicosanedioyl-αGlu-6×OEG), desB30 human insulin; B29K(N(ε)-eicosanedioyl-αGlu-αGlu-5×OEG), desB30 human insulin; B29K(N(ε)-eicosanedioyl-αGlu-αGlu-6×OEG), desB30 human insulin; B29K(N(ε)-eicosanedioyl-αAsp-5×OEG), desB30 human insulin; B29K(N(ε)-eicosanedioyl-αAsp-6×OEG), desB30 human insulin; A14E, B16H, B25H, B29K(N(ε)-eicosanedioyl-γGlu-5×OEG), desB30 human insulin; A14E, B16H, B25H, B29K(N(ε)-eicosanedioyl-γGlu-6×OEG), desB30 human insulin; A14E, B16H, B25H, B29K(N(ε)-eicosanedioyl-γGlu-γGlu-5×OEG), desB30 human insulin; A14E, B16H, B25H, B29K(N(ε)-eicosanedioyl-γGlu-γGlu-6×OEG), desB30 human insulin; A14E, B16H, B25H, B29K(N(ε)-eicosanedioyl-5×OEG-γGlu), desB30 human insulin; A14E, B16H, B25H, B29K(N(ε)-eicosanedioyl-6×OEG-γGlu), desB30 human insulin; A14E, B16H, B25H, B29K(N(ε)-eicosanedioyl-6×OEG-γGlu-γGlu), desB30 human insulin; A14E, B16H, B25H, B29K(N(ε)-eicosanedioyl-5×OEG-γGlu-γGlu), desB30 human insulin; A14E, B16H, B25H, B29K(N(ε)-eicosanedioyl-βAsp-5×OEG), desB30 human insulin; A14E, B16H, B25H, B29K(N(ε)-eicosanedioyl-βAsp-6×OEG), desB30 human insulin; A14E, B16H, B25H, B29K(N(ε)-eicosanedioyl-αGlu-5×OEG), desB30 human insulin; A14E, B16H, B25H, B29K(N(ε)-eicosanedioyl-αGlu-6×OEG), desB30 human insulin; A14E, B16H, B25H, B29K(N(ε)-eicosanedioyl-αGlu-αGlu-5×OEG), desB30 human insulin; A14E, B16H, B25H, B29K(N(ε)-eicosanedioyl-αGlu-αGlu-6×OEG), desB30 human insulin; A14E, B16H, B25H, B29K(N(ε)-eicosanedioyl-αAsp-5×OEG), desB30 human insulin; A14E, B16H, B25H, B29K(N(ε)-eicosanedioyl-αAsp-6×OEG), desB30 human insulin; A14E, B16E, B25H, B29K(N(ε)-eicosanedioyl-γGlu-5×OEG), desB30 human insulin; A14E, B16E, B25H, B29K(N(ε)-eicosanedioyl-γGlu-6×OEG), desB30 human insulin; A14E, B16E, B25H, B29K(N(ε)-eicosanedioyl-γGlu-γGlu-5×OEG), desB30 human insulin; A14E, B16E, B25H, B29K(N(ε)-eicosanedioyl-γGlu-γGlu-6×OEG), desB30 human insulin; A14E, B16E, B25H, B29K(N(ε)-eicosanedioyl-5×OEG-γGlu), desB30 human insulin; A14E, B16E, B25H, B29K(N(ε)-eicosanedioyl-6×OEG-γGlu), desB30 human insulin; A14E, B16E, B25H, B29K(N(ε)-eicosanedioyl-6×OEG-γGlu-γGlu), desB30 human insulin; A14E, B16E, B25H, B29K(N(ε)-eicosanedioyl-5×OEG-γGlu-γGlu), desB30 human insulin; A14E, B16E, B25H, B29K(N(ε)-eicosanedioyl-βAsp-5×OEG), desB30 human insulin; A14E, B16E, B25H, B29K(N(ε)-eicosanedioyl-βAsp-6×OEG), desB30 human insulin; A14E, B16E, B25H, B29K(N(ε)-eicosanedioyl-αGlu-5×OEG), desB30 human insulin; A14E, B16E, B25H, B29K(N(ε)-eicosanedioyl-αGlu-6×OEG), desB30 human insulin; A14E, B16E, B25H, B29K(N(ε)-eicosanedioyl-αGlu-αGlu-5×OEG), desB30 human insulin; A14E, B16E, B25H, B29K(N(ε)-eicosanedioyl-αGlu-αGlu-6×OEG), desB30 human insulin; A14E, B16E, B25H, B29K(N(ε)-eicosanedioyl-αAsp-5×OEG), desB30 human insulin; A14E, B16E, B25H, B29K(N(ε)-eicosanedioyl-αAsp-6×OEG), desB30 human insulin; B29K(N(ε)-eicosanedioyl-γGlu-7×OEG), desB30 human insulin; B29K(N(ε)-eicosanedioyl-γGlu-8×OEG), desB30 human insulin; B29K(N(ε)-eicosanedioyl-γGlu-γGlu-7×OEG), desB30 human insulin; B29K(N(ε)-eicosanedioyl-γGlu-γGlu-8×OEG), desB30 human insulin; B29K(N(ε)-eicosanedioyl-7×OEG-γGlu), desB30 human insulin; B29K(N(ε)-eicosanedioyl-8×OEG-γGlu), desB30 human insulin; B29K(N(ε)-eicosanedioyl-8×OEG-γGlu-γGlu), desB30 human insulin; B29K(N(ε)-eicosanedioyl-7×OEG-γGlu-γGlu), desB30 human insulin; B29K(N(ε)-eicosanedioyl-βAsp-7×OEG), desB30 human insulin; B29K(N(ε)-eicosanedioyl-βAsp-8×OEG), desB30 human insulin; B29K(N(ε)-eicosanedioyl-αGlu-7×OEG), desB30 human insulin; B29K(N(ε)-eicosanedioyl-αGlu-8×OEG), desB30 human insulin; B29K(N(ε)-eicosanedioyl-αGlu-αGlu-7×OEG), desB30 human insulin; B29K(N(ε)-eicosanedioyl-αGlu-αGlu-8×OEG), desB30 human insulin; B29K(N(ε)-eicosanedioyl-αAsp-7×OEG), desB30 human insulin; B29K(N(ε)-eicosanedioyl-αAsp-8×OEG), desB30 human insulin; A14E, B16H, B25H, B29K(N(ε)-eicosanedioyl-γGlu-7×OEG), desB30 human insulin; A14E, B16H, B25H, B29K(N(ε)-eicosanedioyl-γGlu-8×OEG), desB30 human insulin; A14E, B16H, B25H, B29K(N(ε)-eicosanedioyl-γGlu-γGlu-7×OEG), desB30 human insulin; A14E, B16H, B25H, B29K(N(ε)-eicosanedioyl-γGlu-γGlu-8×OEG), desB30 human insulin; A14E, B16H, B25H, B29K(N(ε)-eicosanedioyl-7×OEG-γGlu), desB30 human insulin; A14E, B16H, B25H, B29K(N(ε)-eicosanedioyl-8×OEG-γGlu), desB30 human insulin; A14E, B16H, B25H, B29K(N(ε)-eicosanedioyl-8×OEG-γGlu-γGlu), desB30 human insulin; A14E, B16H, B25H, B29K(N(ε)-eicosanedioyl-7×OEG-γGlu-γGlu), desB30 human insulin; A14E, B16H, B25H, B29K(N(ε)-eicosanedioyl-βAsp-7×OEG), desB30 human insulin; A14E, B16H, B25H, B29K(N(ε)-eicosanedioyl-βAsp-8×OEG), desB30 human insulin; A14E, B16H, B25H, B29K(N(ε)-eicosanedioyl-αGlu-7×OEG), desB30 human insulin; A14E, B16H, B25H, B29K(N(ε)-eicosanedioyl-αGlu-8×OEG), desB30 human insulin; A14E, B16H, B25H, B29K(N(ε)-eicosanedioyl-αGlu-αGlu-7×OEG), desB30 human insulin; A14E, B16H, B25H, B29K(N(ε)-eicosanedioyl-αGlu-αGlu-8×OEG), desB30 human insulin; A14E, B16H, B25H, B29K(N(ε)-eicosanedioyl-αAsp-7×OEG), desB30 human insulin; A14E, B16H, B25H, B29K(N(ε)-eicosanedioyl-αAsp-8×OEG), desB30 human insulin; A14E, B16E, B25H, B29K(N(ε)-eicosanedioyl-γGlu-7×OEG), desB30 human insulin; A14E, B16E, B25H, B29K(N(ε)-eicosanedioyl-γGlu-8×OEG), desB30 human insulin; A14E, B16E, B25H, B29K(N(ε)-eicosanedioyl-γGlu-γGlu-7×OEG), desB30 human insulin; A14E, B16E, B25H, B29K(N(ε)-eicosanedioyl-γGlu-γGlu-8×OEG), desB30 human insulin; A14E, B16E, B25H, B29K(N(ε)-eicosanedioyl-7×OEG-γGlu), desB30 human insulin; A14E, B16E, B25H, B29K(N(ε)-eicosanedioyl-8×OEG-γGlu), desB30 human insulin; A14E, B16E, B25H, B29K(N(ε)-eicosanedioyl-8×OEG-γGlu-γGlu), desB30 human insulin; A14E, B16E, B25H, B29K(N(ε)-eicosanedioyl-7×OEG-γGlu-γGlu), desB30 human insulin; A14E, B16E, B25H, B29K(N(ε)-eicosanedioyl-βAsp-7×OEG), desB30 human insulin; A14E, B16E, B25H, B29K(N(ε)-eicosanedioyl-βAsp-8×OEG), desB30 human insulin; A14E, B16E, B25H, B29K(N(ε)-eicosanedioyl-αGlu-7×OEG), desB30 human insulin; A14E, B16E, B25H, B29K(N(ε)-eicosanedioyl-αGlu-8×OEG), desB30 human insulin; A14E, B16E, B25H, B29K(N(ε)-eicosanedioyl-αGlu-αGlu-7×OEG), desB30 human insulin; A14E, B16E, B25H, B29K(N(ε)-eicosanedioyl-αGlu-αGlu-8×OEG), desB30 human insulin; A14E, B16E, B25H, B29K(N(ε)-eicosanedioyl-αAsp-7×OEG), desB30 human insulin; A14E, B16E, B25H, B29K(N(ε)-eicosanedioyl-αAsp-8×OEG), desB30 human insulin; B29K(N(ε)-docosanedioyl-γGlu-5×OEG), desB30 human insulin; B29K(N(ε)-docosanedioyl-γGlu-6×OEG), desB30 human insulin; B29K(N(ε)-docosanedioyl-γGlu-γGlu-5×OEG), desB30 human insulin; B29K(N(ε)-docosanedioyl-γGlu-γGlu-6×OEG), desB30 human insulin; B29K(N(ε)-docosanedioyl-5×OEG- γGlu), desB30 human insulin; B29K(N(ε)-docosanedioyl-6×OEG-γGlu), desB30 human insulin; B29K(N(ε)-docosanedioyl-6×OEG-γGlu-γGlu), desB30 human insulin; B29K(N(ε)-docosanedioyl-5×OEG-γGlu-γGlu), desB30 human insulin; B29K(N(ε)-docosanedioyl-βAsp-5×OEG), desB30 human insulin; B29K(N(ε)-docosanedioyl-βAsp-6×OEG), desB30 human insulin; B29K(N(ε)-docosanedioyl-αGlu-5×OEG), desB30 human insulin; B29K(N(ε)-docosanedioyl-αGlu-6×OEG), desB30 human insulin; B29K(N(ε)-docosanedioyl-αGlu-Glu-5×OEG), desB30 human insulin; B29K(N(ε)-docosanedioyl-αGlu-αGlu-6×OEG), desB30 human insulin; B29K(N(ε)-docosanedioyl-αAsp-5×OEG), desB30 human insulin; B29K(N(ε)-docosanedioyl-αAsp-6×OEG), desB30 human insulin; A14E, B16H, B25H, B29K(N(ε)-docosanedioyl-γGlu-5×OEG), desB30 human insulin; A14E, B16H, B25H, B29K(N(ε)-docosanedioyl-γGlu-6×OEG), desB30 human insulin; A14E, B16H, B25H, B29K(N(ε)-docosanedioyl-γGlu-γGlu-5×OEG), desB30 human insulin; A14E, B16H, B25H, B29K(N(ε)-docosanedioyl-γGlu-γGlu-6×OEG), desB30 human insulin; A14E, B16H, B25H, B29K(N(ε)-docosanedioyl-5×OEG-γGlu), desB30 human insulin; A14E, B16H, B25H, B29K(N(ε)-docosanedioyl-6×OEG-γGlu), desB30 human insulin; A14E, B16H, B25H, B29K(N(ε)-docosanedioyl-6×OEG-γGlu-γGlu), desB30 human insulin; A14E, B16H, B25H, B29K(N(ε)-docosanedioyl-5×OEG-γGlu-γGlu), desB30 human insulin; A14E, B16H, B25H, B29K(N(ε)-docosanedioyl-βAsp-5×OEG), desB30 human insulin; A14E, B16H, B25H, B29K(N(ε)-docosanedioyl-βAsp-6×OEG), desB30 human insulin; A14E, B16H, B25H, B29K(N(ε)-docosanedioyl-αGlu-5×OEG), desB30 human insulin; A14E, B16H, B25H, B29K(N(ε)-docosanedioyl-αGlu-6×OEG), desB30 human insulin; A14E, B16H, B25H, B29K(N(ε)-docosanedioyl-αGlu-αGlu-5×OEG), desB30 human insulin; A14E, B16H, B25H, B29K(N(ε)-docosanedioyl-αGlu-αGlu-6×OEG), desB30 human insulin; A14E, B16H, B25H, B29K(N(ε)-docosanedioyl-αAsp-5×OEG), desB30 human insulin; A14E, B16H, B25H, B29K(N(ε)-docosanedioyl-αAsp-6×OEG), desB30 human insulin; A14E, B16E, B25H, B29K(N(ε)-docosanedioyl-γGlu-5×OEG), desB30 human insulin; A14E, B16E, B25H, B29K(N(ε)-docosanedioyl-γGlu-6×OEG), desB30 human insulin; A14E, B16E, B25H, B29K(N(ε)-docosanedioyl-γGlu-γGlu-5×OEG), desB30 human insulin; A14E, B16E, B25H, B29K(N(ε)-docosanedioyl-γGlu-γGlu-6×OEG), desB30 human insulin; A14E, B16E, B25H, B29K(N(ε)-docosanedioyl-5×OEG-γGlu), desB30 human insulin; A14E, B16E, B25H, B29K(N(ε)-docosanedioyl-6×OEG-γGlu), desB30 human insulin; A14E, B16E, B25H, B29K(N(ε)-docosanedioyl-6×OEG-γGlu-γGlu), desB30 human insulin; A14E, B16E, B25H, B29K(N(ε)-docosanedioyl-5×OEG-γGlu-γGlu), desB30 human insulin; A14E, B16E, B25H, B29K(N(ε)-docosanedioyl-βAsp-5×OEG), desB30 human insulin; A14E, B16E, B25H, B29K(N(ε)-docosanedioyl-βAsp-6×OEG), desB30 human insulin; A14E, B16E, B25H, B29K(N(ε)-docosanedioyl-αGlu-5×OEG), desB30 human insulin; A14E, B16E, B25H, B29K(N(ε)-docosanedioyl-αGlu-6×OEG), desB30 human insulin; A14E, B16E, B25H, B29K(N(ε)-docosanedioyl-αGlu-αGlu-5×OEG), desB30 human insulin; A14E, B16E, B25H, B29K(N(ε)-docosanedioyl-αGlu-αGlu-6×OEG), desB30 human insulin; A14E, B16E, B25H, B29K(N(ε)-docosanedioyl-αAsp-5×OEG), desB30 human insulin; A14E, B16E, B25H, B29K(N(ε)-docosanedioyl-αAsp-6×OEG), desB30 human insulin; B29K(N(ε)-docosanedioyl-γGlu-7×OEG), desB30 human insulin; B29K(N(ε)-docosanedioyl-γGlu-8×OEG), desB30 human insulin; B29K(N(ε)-docosanedioyl-γGlu-γGlu-7×OEG), desB30 human insulin; B29K(N(ε)-docosanedioyl-γGlu-γGlu-8×OEG), desB30 human insulin; B29K(N(ε)-docosanedioyl-7×OEG-γGlu), desB30 human insulin; B29K(N(ε)-docosanedioyl-8×OEG-γGlu), desB30 human insulin; B29K(N(ε)-docosanedioyl-8×OEG-γGlu-γGlu), desB30 human insulin; B29K(N(ε)-docosanedioyl-7×OEG-γGlu-γGlu), desB30 human insulin; B29K(N(ε)-docosanedioyl-βAsp-7×OEG), desB30 human insulin; B29K(N(ε)-docosanedioyl-βAsp-8×OEG), desB30 human insulin; B29K(N(ε)-docosanedioyl-αGlu-7×OEG), desB30 human insulin; B29K(N(ε)-docosanedioyl-αGlu-8×OEG), desB30 human insulin; B29K(N(ε)-docosanedioyl-αGlu-αGlu-7×OEG), desB30 human insulin; B29K(N(ε)-docosanedioyl-αGlu-αGlu-8×OEG), desB30 human insulin; B29K(N(ε)-docosanedioyl-αAsp-7×OEG), desB30 human insulin; B29K(N(ε)-docosanedioyl-αAsp-8×OEG), desB30 human insulin; A14E, B16H, B25H, B29K(N(ε)-docosanedioyl-γGlu-7×OEG), desB30 human insulin; A14E, B16H, B25H, B29K(N(ε)-docosanedioyl-γGlu-8×OEG), desB30 human insulin; A14E, B16H, B25H, B29K(N(ε)-docosanedioyl-γGlu-γGlu-7×OEG), desB30 human insulin; A14E, B16H, B25H, B29K(N(ε)-docosanedioyl-γGlu-γGlu-8×OEG), desB30 human insulin; A14E, B16H, B25H, B29K(N(ε)-docosanedioyl-7×OEG-γGlu), desB30 human insulin; A14E, B16H, B25H, B29K(N(ε)-docosanedioyl-8×OEG-γGlu), desB30 human insulin; A14E, B16H, B25H, B29K(N(ε)-docosanedioyl-8×OEG-γGlu-γGlu), desB30 human insulin; A14E, B16H, B25H, B29K(N(ε)-docosanedioyl-7×OEG-γGlu-γGlu), desB30 human insulin; A14E, B16H, B25H, B29K(N(ε)-docosanedioyl-βAsp-7×OEG), desB30 human insulin; A14E, B16H, B25H, B29K(N(ε)-docosanedioyl-βAsp-8×OEG), desB30 human insulin; A14E, B16H, B25H, B29K(N(ε)-docosanedioyl-αGlu-7×OEG), desB30 human insulin; A14E, B16H, B25H, B29K(N(ε)-docosanedioyl-αGlu-8×OEG), desB30 human insulin; A14E, B16H, B25H, B29K(N(ε)-docosanedioyl-αGlu-αGlu-7×OEG), desB30 human insulin; A14E, B16H, B25H, B29K(N(ε)-docosanedioyl-αGlu-Glu-8×OEG), desB30 human insulin; A14E, B16H, B25H, B29K(N(ε)-docosanedioyl-αAsp-7×OEG), desB30 human insulin; A14E, B16H, B25H, B29K(N(ε)-docosanedioyl-αAsp-8×OEG), desB30 human insulin; A14E, B16E, B25H, B29K(N(ε)-docosanedioyl-γGlu-7×OEG), desB30 human insulin; A14E, B16E, B25H, B29K(N(ε)-docosanedioyl-γGlu-8×OEG), desB30 human insulin; A14E, B16E, B25H, B29K(N(ε)-docosanedioyl-γGlu-γGlu-7×OEG), desB30 human insulin; A14E, B16E, B25H, B29K(N(ε)-docosanedioyl-γGlu-γGlu-8×OEG), desB30 human insulin; A14E, B16E, B25H, B29K(N(ε)-docosanedioyl-7×OEG-γGlu), desB30 human insulin; A14E, B16E, B25H, B29K(N(ε)-docosanedioyl-8×OEG-γGlu), desB30 human insulin; A14E, B16E, B25H, B29K(N(ε)-docosanedioyl-8×OEG-γGlu-γGlu), desB30 human insulin; A14E, B16E, B25H, B29K(N(ε)-docosanedioyl-7×OEG-γGlu-γGlu), desB30 human insulin; A14E, B16E, B25H, B29K(N(ε)-docosanedioyl-βAsp-7×OEG), desB30 human insulin; A14E, B16E, B25H, B29K(N(ε)-docosanedioyl-βAsp-8×OEG), desB30 human insulin; A14E, B16E, B25H, B29K(N(ε)-docosanedioyl-αGlu-7×OEG), desB30 human insulin; A14E, B16E, B25H, B29K(N(ε)-docosanedioyl-αGlu-8×OEG), desB30 human insulin; A14E, B16E, B25H, B29K(N(ε)-docosanedioyl-αGlu-αGlu-7×OEG), desB30 human insulin; A14E, B16E, B25H, B29K(N(ε)-docosanedioyl-αGlu-Glu-8×OEG), desB30 human insulin; A14E, B16E, B25H, B29K(N(ε)-docosanedioyl-αAsp-7×OEG), desB30 human insulin; A14E, B16E, B25H, B29K(N(ε)-docosanedioyl-αAsp-8×OEG), desB30 human insulin; B29K(N(ε)-heneicosanedioyl-γGlu-5×OEG), desB30 human insulin; B29K(N(ε)- heneicosanedioyl-γGlu-6×OEG), desB30 human insulin; A14E, B16H, B25H, B29K(N(ε)-heneicosanedioyl-γGlu-5×OEG), desB30 human insulin; A14E, B16H, B25H, B29K(N(ε)-heneicosanedioyl-γGlu-6×OEG), desB30 human insulin; A14E, B16E, B25H, B29K(N(ε)-heneicosanedioyl-γGlu-5×OEG), desB30 human insulin; A14E, B16E, B25H, B29K(N(ε)-heneicosanedioyl-γGlu-6×OEG), desB30 human insulin; B29K(N(ε)-heneicosanedioyl-γGlu-7×OEG), desB30 human insulin; B29K(N(ε)-heneicosanedioyl-γGlu-8×OEG), desB30 human insulin; A14E, B16H, B25H, B29K(N(ε)-heneicosanedioyl-γGlu-7×OEG), desB30 human insulin; A14E, B16H, B25H, B29K(N(ε)-heneicosanedioyl-γGlu-8×OEG), desB30 human insulin; A14E, B16E, B25H, B29K(N(ε)-heneicosanedioyl-γGlu-7×OEG), desB30 human insulin; A14E, B16E, B25H, B29K(N(ε)-heneicosanedioyl-γGlu-8×OEG), desB30 human insulin; B29K(N(ε)-tricosanedioyl-γGlu-5×OEG), desB30 human insulin; B29K(N(ε)-tricosanedioyl-γGlu-6×OEG), desB30 human insulin; A14E, B16H, B25H, B29K(N(ε)-tricosanedioyl-γGlu-5×OEG), desB30 human insulin; A14E, B16H, B25H, B29K(N(ε)-tricosanedioyl-γGlu-6×OEG), desB30 human insulin; A14E, B16E, B25H, B29K(N(ε)-tricosanedioyl-γGlu-5×OEG), desB30 human insulin; A14E, B16E, B25H, B29K(N(ε)-tricosanedioyl-γGlu-6×OEG), desB30 human insulin; B29K(N(ε)-tricosanedioyl-γGlu-7×OEG), desB30 human insulin; B29K(N(ε)-tricosanedioyl-γGlu-8×OEG), desB30 human insulin; A14E, B16H, B25H, B29K(N(ε)-tricosanedioyl-γGlu-7×OEG), desB30 human insulin; A14E, B16H, B25H, B29K(N(ε)-tricosanedioyl-γGlu-8×OEG), desB30 human insulin; A14E, B16E, B25H, B29K(N(ε)-tricosanedioyl-γGlu-7×OEG), desB30 human insulin; A14E, B16E, B25H, B29K(N(ε)-tricosanedioyl-γGlu-8×OEG), desB30 human insulin; B29K(N(ε)-tetracosanedioyl-γGlu-5×OEG), desB30 human insulin; B29K(N(ε)-tetracosanedioyl-γGlu-6×OEG), desB30 human insulin; A14E, B16H, B25H, B29K(N(ε)-tetracosanedioyl-γGlu-5×OEG), desB30 human insulin; A14E, B16H, B25H, B29K(N(ε)-tetracosanedioyl-γGlu-6×OEG), desB30 human insulin; A14E, B16E, B25H, B29K(N(ε)-tetracosanedioyl-γGlu-5×OEG), desB30 human insulin; A14E, B16E, B25H, B29K(N(ε)-tetracosanedioyl-γGlu-6×OEG), desB30 human insulin; B29K(N(ε)-tetracosanedioyl-γGlu-7×OEG), desB30 human insulin; B29K(N(ε)-tetracosanedioyl-γGlu-8×OEG), desB30 human insulin; A14E, B16H, B25H, B29K(N(ε)-tetracosanedioyl-γGlu-7×OEG), desB30 human insulin; A14E, B16H, B25H, B29K(N(ε)-tetracosanedioyl-γGlu-8×OEG), desB30 human insulin; A14E, B16E, B25H, B29K(N(ε)-tetracosanedioyl-γGlu-7×OEG), desB30 human insulin; A14E, B16E, B25H, B29K(N(ε)-tetracosanedioyl-γGlu-8×OEG), desB30 human insulin; B29K(N(ε)-eicosanedioyl-γGlu-12×OEG), desB30 human insulin; B29K(N(ε)-docosanedioyl-γGlu-12×OEG), desB30 human insulin; A14E, B16H, B25H, B29K(N(ε)-eicosanedioyl-γGlu-12×OEG), desB30 human insulin; A14E, B16H, B25H, B29K(N(ε)-docosanedioyl-γGlu-12×OEG), desB30 human insulin; A14E, B16E, B25H, B29K(N(ε)-eicosanedioyl-γGlu-12×OEG), desB30 human insulin; A14E, B16E, B25H, B29K(N(ε)-docosanedioyl-γGlu-12×OEG), desB30 human insulin; A14E, B16H, B25H, B29K(N(ε)-eicosanedioyl-γGlu-9×OEG), desB30 human insulin; A14E, B16H, B25H, B29K(N(ε)-eicosanedioyl-γGlu-10×OEG), desB30 human insulin; A14E, B16H, B25H, B29K(N(ε)-eicosanedioyl-γGlu-11×OEG), desB30 human insulin; A14E, B16H, B25H, B29K(N(ε)-docosanedioyl-γGlu-9×OEG), desB30 human insulin; A14E, B16H, B25H, B29K(N(ε)-docosanedioyl-γGlu-10×OEG), desB30 human insulin; A14E, B16H, B25H, B29K(N(ε)-docosanedioyl-γGlu-11×OEG), desB30 human insulin; A14E, B16H, B25H, B29K(N(ε)-heneicosanedioyl-γGlu-12×OEG), desB30 human insulin; A14E, B16H, B25H, B29K(N(ε)-tricosanedioyl-γGlu-12×OEG), desB30 human insulin; A14E, B16H, B25H, B29K(N(ε)-tetracosanedioyl-γGlu-12×OEG), desB30 human insulin; A14E, B16E, B25H, B29K(N(ε)-eicosanedioyl-γGlu-9×OEG), desB30 human insulin; A14E, B16E, B25H, B29K(N(ε)-eicosanedioyl-γGlu-10×OEG), desB30 human insulin; A14E, B16E, B25H, B29K(N(ε)-eicosanedioyl-γGlu-11×OEG), desB30 human insulin; A14E, B16E, B25H, B29K(N(ε)-docosanedioyl-γGlu-9×OEG), desB30 human insulin; A14E, B16E, B25H, B29K(N(ε)-docosanedioyl-γGlu-10×OEG), desB30 human insulin; A14E, B16E, B25H, B29K(N(ε)-docosanedioyl-γGlu-11×OEG), desB30 human insulin; A14E, B16E, B25H, B29K(N(ε)-heneicosanedioyl-γGlu-12×OEG), desB30 human insulin; A14E, B16E, B25H, B29K(N(ε)-tricosanedioyl-γGlu-12×OEG), desB30 human insulin; A14E, B16E, B25H, B29K(N(ε)-tetracosanedioyl-γGlu-12×OEG), desB30 human insulin; B29K(N(ε)-eicosanedioyl-γGlu-9×OEG), desB30 human insulin; B29K(N(ε)-eicosanedioyl-γGlu-10×OEG), desB30 human insulin; B29K(N(ε)-eicosanedioyl-γGlu-11×OEG), desB30 human insulin; B29K(N(ε)-docosanedioyl-γGlu-9×OEG), desB30 human insulin; B29K(N(ε)-docosanedioyl-γGlu-10×OEG), desB30 human insulin; B29K(N(ε)-docosanedioyl-γGlu-11×OEG), desB30 human insulin; B29K(N(ε)-heneicosanedioyl-γGlu-12×OEG), desB30 human insulin; B29K(N(ε)-tricosanedioyl-γGlu-12×OEG), desB30 human insulin; B29K(N(ε)-tetracosanedioyl-γGlu-12×OEG), desB30 human insulin; A14E, B16H, B25H, B29K(N(ε)-docosanedioyl-γGlu-18×OEG), desB30 human insulin; and A14E, B16H, B25H, B29K(N(ε)-docosanedioyl-γGlu-24×OEG), desB30 human insulin.

The inventors have surprisingly found that the pharmaceutical composition of the compound according to the first aspect of the present invention and an acylated insulin does not impair the physical stability of the compound; instead, the combo formulation has better physical stability than the mono formulation. The physical stability of the combo formulation disclosed herein is beyond expectation compared to combo formulations of other long-acting insulin derivatives, e.g., insulin degludec and liraglutide. Furthermore, the combo formulation also allows for an increase in the chemical stability of the acylated insulin compared to the mono formulation.

In a fourth aspect of the present invention, provided is a compound according to the first aspect of the present invention, a pharmaceutical formulation according to the second aspect of the present invention or a pharmaceutical composition according to the third aspect of the present invention for use as a medicament.

In one embodiment, the compound according to the first aspect of the present invention, the pharmaceutical formulation according to the second aspect of the present invention or the pharmaceutical composition according to the third aspect of the present invention is for use in treating or preventing hyperglycemia, diabetes and/or obesity.

In a fifth aspect of the present invention, provided is use of the compound according to the first aspect of the present invention, the pharmaceutical formulation according to the second aspect of the present invention or the pharmaceutical composition according to the third aspect of the present invention for the manufacture of a medicament for use in treating or preventing hyperglycemia, diabetes and/or obesity.

In a sixth aspect of the present invention, provided is a method for treating or preventing hyperglycemia, diabetes and/or obesity, the method comprises administering an effective amount of the compound according to the first aspect of the present invention, the pharmaceutical formulation according to the second aspect of the present invention, or the pharmaceutical composition according to the third aspect of the present invention, the disease including, but not limited to, for example, hyperglycemia, diabetes, and obesity.

DETAILED DESCRIPTION

Definitions

GLP-1 Analogues and GLP-1 Derivatives

Figure 1A:
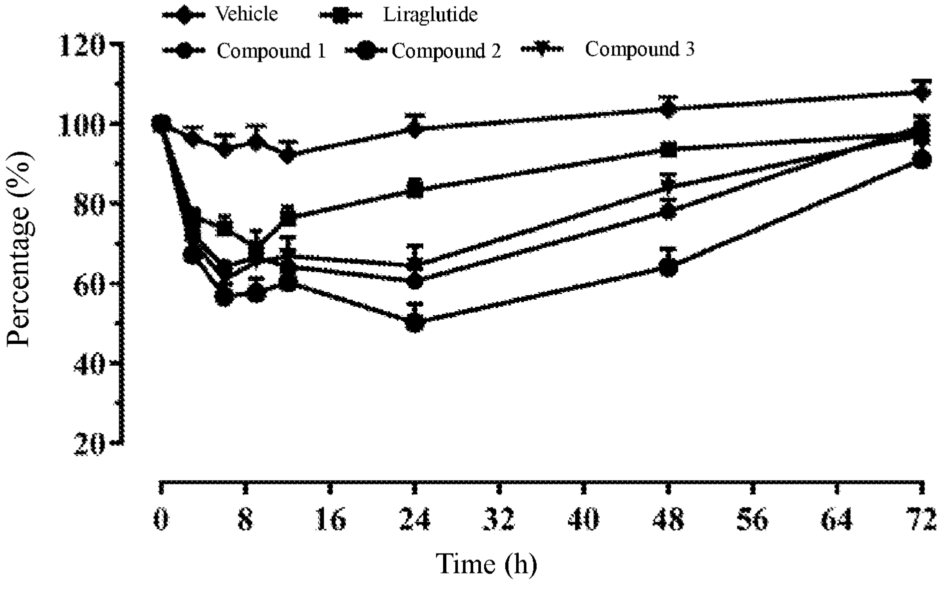
FIG. 1*a* shows the hypoglycemic effect and duration of action of the title compounds of Examples 1-3 according to the present invention, liraglutide and vehicle on db/db mice, wherein the percentage on the ordinate refers to the percentage of blood glucose at each monitoring point obtained by dividing the blood glucose at the corresponding time point after the administration by the baseline blood glucose before administration (same below).
Figure 1B:
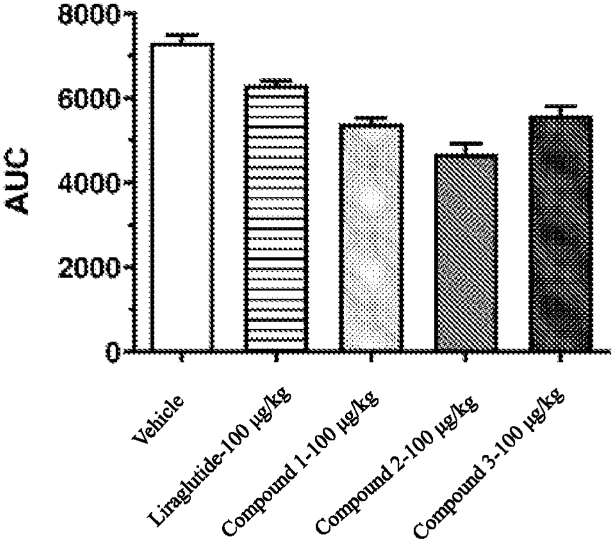
FIG. 1*b* shows, in correspondence with FIG. 1*a*, the AUC of the hypoglycemic effect of the title compounds of Examples 1-3 according to the present invention, liraglutide and vehicle on db/db mice.
Figure 2A:
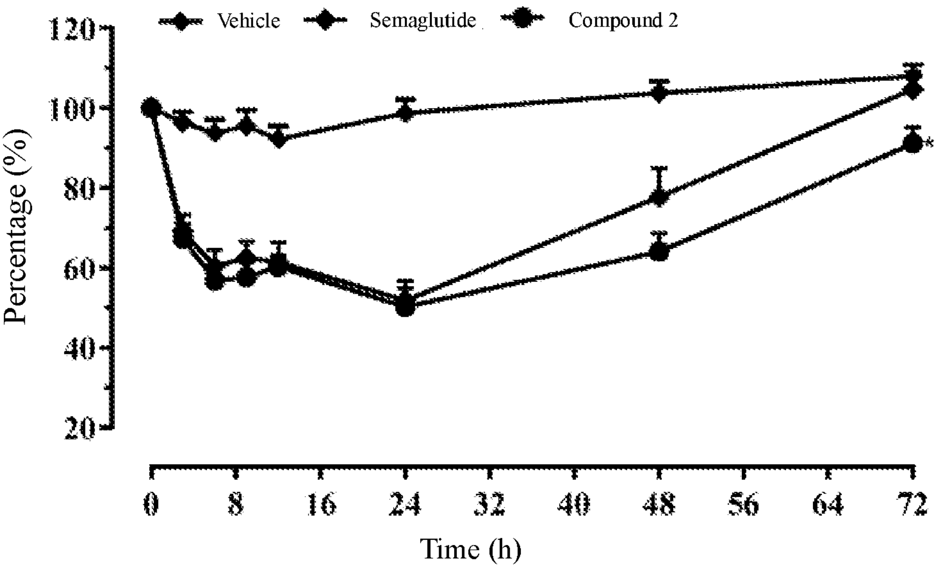
FIG. 2*a* shows the hypoglycemic effect and duration of action of the title compound of Example 2 according to the present invention, semaglutide and vehicle on db/db mice.
Figure 2B:
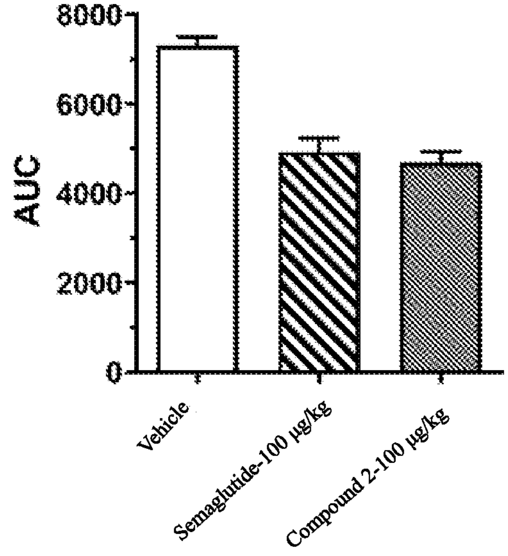
FIG. 2*b* shows, in correspondence with FIG. 2*a*, the AUC of the hypoglycemic effect of the title compound of Example 2 according to the present invention, semaglutide and vehicle on db/db mice.
Figure 3A:
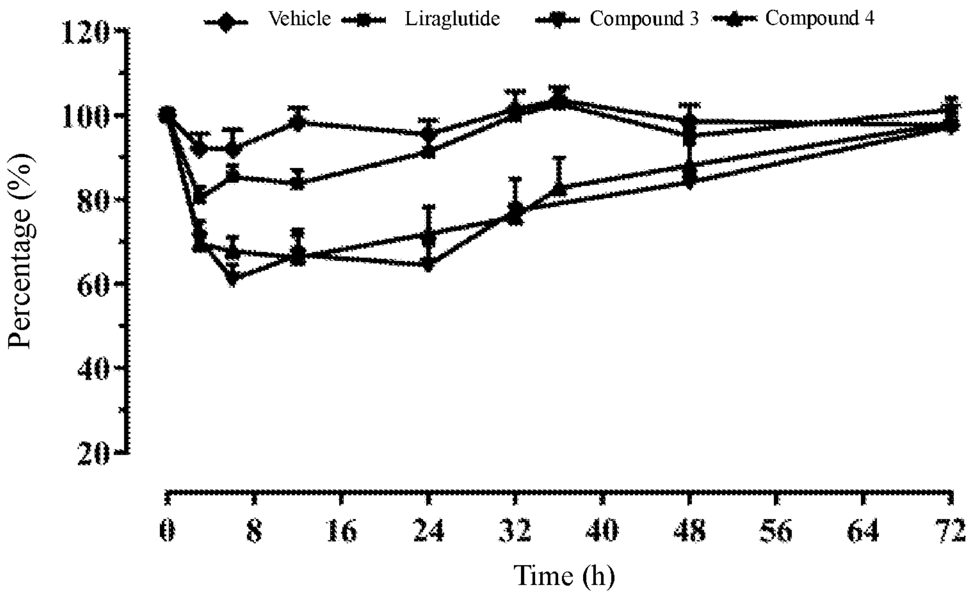
FIG. 3*a* shows the hypoglycemic effect and duration of action of the title compounds of Examples 3-4 according to the present invention, liraglutide and vehicle on db/db mice.
Figure 3B:
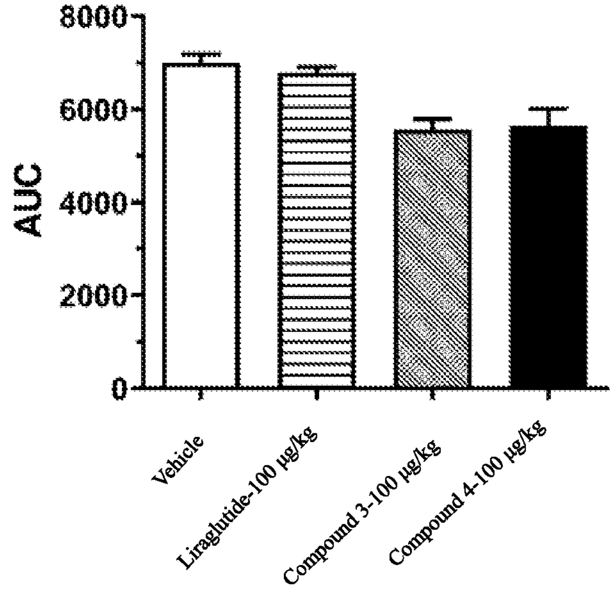
FIG. 3*b* shows, in correspondence with FIG. 3*a*, the AUC of the hypoglycemic effect of the title compounds of Examples 3-4 according to the present invention, liraglutide and vehicle on db/db mice.
Figure 4A:
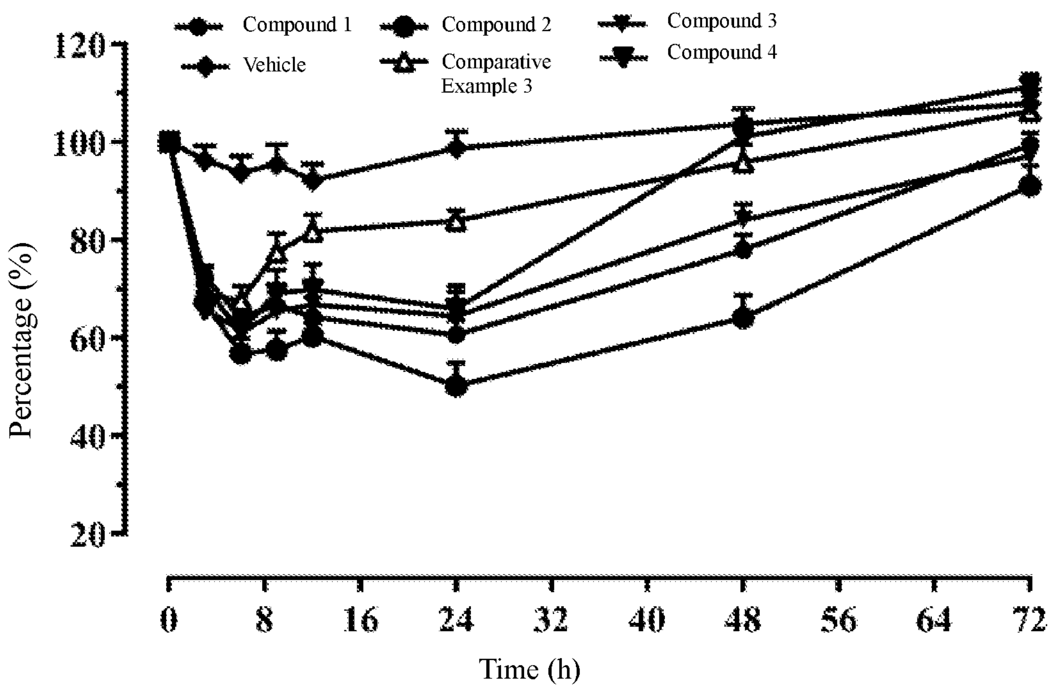
FIG. 4*a* shows the hypoglycemic effect and duration of action of the title compounds of Examples 1-3 and Comparative Examples 3-4 according to the present invention, and vehicle on db/db mice.
Figure 4B:
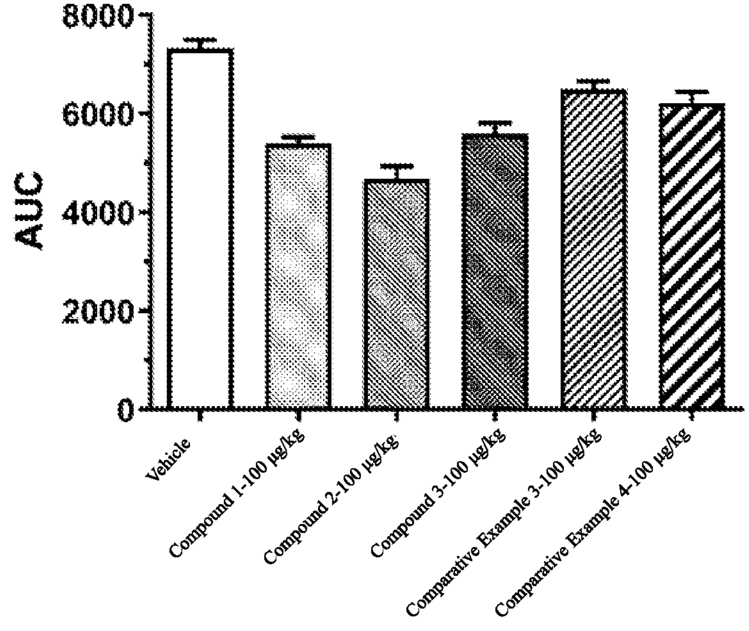
FIG. 4*b* shows, in correspondence with FIG. 4*a*, the AUC of the hypoglycemic effect of the title compounds of Examples 1-3 and Comparative Examples 3-4 according to the present invention, and vehicle on db/db mice.

As used herein, the term "GLP-1 analogue" or "analogue of GLP-1" refers to a peptide or compound that is a variant of human glucagon-like peptide-1 (GLP-1(7-37)), wherein one or more amino acid residues of GLP-1(7-37) are replaced, and/or one or more amino acid residues are deleted, and/or one or more amino acid residues are added. Specifically, the sequence of GLP-1(7-37) is set forth in SEQ ID NO: 1 in the sequence listing. A peptide having the sequence set forth in SEQ ID NO: 1 may also be referred to as "natural" GLP-1 or "natural" GLP-1(7-37).

In the sequence listing, the first amino acid residue (His) in SEQ ID NO: 1 is numbered 1. However, in the following, according to established practice in the art, the histidine residue is numbered 7 and the following amino acid residues are numbered sequentially, ending with glycine as No. 37. Thus, in general, based on the numbering for amino acid residues or positions, the GLP-1(7-37) sequence referred to herein is a sequence starting with His at position 7 and ending with Gly at position 37.

[Gly8, Arg34]GLP-1-(7-37) peptide is a GLP-1 analogue having Gly and Arg at positions corresponding to position 8 and position 34, respectively, of GLP-1(7-37) (SEQ ID NO: 1), and [Arg34]GLP-1-(7-37) peptide is a GLP-1 analogue having Arg at a position corresponding to position 34 of GLP-1(7-37) (SEQ ID NO: 1). Specifically, the amino acid sequences of [Gly8, Arg34]GLP-1-(7-37) peptide and [Arg34]GLP-1-(7-37) peptide are set forth in SEQ ID NO: 2 and SEQ ID NO: 3 in the sequence listing, respectively.

In the case of a GLP-1 peptide or an analogue thereof, the term "derivative" as used herein refers to a chemically modified GLP-1 peptide or analogue, wherein one or more substituents have been covalently linked to the peptide. Substituents may also be referred to as side chains.

Unless otherwise stated, when reference is made to acylation with a lysine residue, it is understood to be performed with an ε-amino group of the lysine residue.

The GLP-1 derivative of formula (B) disclosed herein may exist in different stereoisomeric forms, which have the same molecular formula and sequence of linked atoms, but differ only in the three-dimensional direction of their atomic space. Unless otherwise stated, the present invention relates to all stereoisomeric forms of the claimed derivatives.

The term "peptide", when used, for example, for the GLP-1 analogue disclosed herein, refers to a compound comprising a series of amino acids linked to one another by amido (or peptide) bonds.

In a specific embodiment, the peptide consists largely or mainly of amino acids linked to one another by amide bonds (e.g., at least 50%, 60%, 70%, 80% or 90% of the molar mass). In another specific embodiment, the peptide consists of amino acids linked to one another by peptide bonds.

Amino acids are molecules containing amino and carboxyl groups, and optionally containing one or more additional groups commonly referred to as side chains.

The term "amino acid" encompasses proteinogenic amino acids (encoded by the genetic code, including natural amino acids and standard amino acids), non-proteinogenic amino acids (not found in proteins and/or not encoded by the standard genetic code), and synthetic amino acids. Non-proteinogenic amino acids are moieties that can be incorporated into a peptide by peptide bonds, but are not proteinogenic amino acids. Synthetic non-proteinogenic amino acids include amino acids produced by chemical synthesis, i.e., D-isomers of amino acids encoded by the genetic code such as D-alanine and D-leucine, Aib (α-aminoisobutyric acid), Abu (α-aminobutyric acid), 3-aminomethylbenzoic acid, o-aminobenzoic acid, deamino-histidine, β analogues of amino acids (e.g., β-alanine), D-histidine, deamino-histidine, 2-amino-histidine, β-hydroxy-histidine and homohistidine.

Non-limiting examples of amino acids not encoded by the genetic code are γ-carboxyglutamic acid, ornithine, D-alanine, D-glutamine and phosphoserine. Non-limiting examples of synthetic amino acids are D-isomers of the amino acids, such as D-alanine and D-leucine, Aib (α-aminoisobutyric acid), β-alanine and des-amino-histidine (desH, with the alternative name of imidazole propionic acid, abbreviated as Imp).

In the following, all amino acids for which optical isomers are not indicated are understood to refer to L-isomers (unless stated otherwise).

Pharmaceutically Acceptable Salts, Amides or Esters

The GLP-1 derivatives, analogues and intermediates disclosed herein may be in the form of pharmaceutically acceptable salts, amides or esters. The salts may be basic, acidic, or neutral salts. Basic salts produce hydroxide ions and acidic salts produce hydronium ions in water. The salts of the derivatives disclosed herein may be formed by the reactions of added cations or anions with anionic groups or cationic groups, respectively. Those groups may be located in the peptide moiety and/or in the side chains of the derivatives disclosed herein.

Non-limiting examples of anionic groups of the derivatives disclosed herein include side chains (if any) and free carboxyl groups in the peptide moiety. The peptide moiety typically comprises anionic groups including a free carboxylic acid at the C-terminus as well as free carboxyl groups on internal acidic amino acid residues such as Asp and Glu.

Non-limiting examples of cationic groups of the peptide moiety include a free amino group (if any) at the N-terminus and any free amino groups on internal basic amino acid residues such as His, Arg and Lys.

Esters of the derivatives disclosed herein may be formed, for example, by the reaction of free carboxylic acid groups with alcohols or phenols, which results in the substitution of at least one hydroxyl group by an alkoxy or aryloxy group. The formation of the esters may involve a free carboxyl group at the C-terminus of the peptide and/or any free carboxyl groups in the side chain.

Amides of the derivatives disclosed herein may be formed, for example, by the reaction of free carboxylic acid groups with amines or substituted amines, or by the reaction of free or substituted amino groups with carboxylic acids. The formation of amides may involve a free carboxyl group at the C-terminus of the peptide, any free carboxyl groups in the side chain, a free amino group at the N-terminus of the peptide, and/or any free or substituted peptidic amino groups in the peptide and/or side chain.

In a specific embodiment, the GLP-1 compounds or GLP-1 derivatives disclosed herein are in the form of pharmaceutically acceptable salts. In another specific embodiment, they are in the form of pharmaceutically acceptable amides, preferably have an amide group at the C-terminus of the peptide. In yet another specific embodiment, the peptides or derivatives are in the form of pharmaceutically acceptable esters.

The method for preparing the peptides of GLP-1(7-37) and the GLP-1 analogues of the present invention is well known in the art. For example, the GLP-1 peptide moiety (or a fragment thereof) of the derivatives disclosed herein and the GLP-1 analogues disclosed herein can be produced by classical peptide synthesis, such as solid phase peptide synthesis using t-Boc or Fmoc chemistry or other well-established techniques, see, e.g., Greene and Wuts, "Protective Groups in Organic Synthesis", John Wiley & Sons, 1999, Florencio Zaragoza "Organic Synthesis on Solid Phase", Wiley-VCH Verlag GmbH, 2000, and W. C. Chan and P. D. White, Ed., "Fmoc Solid Phase Peptide Synthesis", Oxford University Press, 2000.

In one embodiment, the intact GLP-1 analogues disclosed herein, e.g., [Gly8, Arg34]GLP-1-(7-37) peptide, can be produced by recombination, i.e., by culturing a host cell containing a DNA sequence encoding the analogue and capable of expressing the peptide in a suitable nutrient medium under conditions that allow the expression of the peptide. Non-limiting examples of host cells suitable for expressing those peptides are *Escherichia coli, Saccharomyces cerevisiae* and mammalian BHK or CHO cell lines. In some embodiments, this fully recombinant fermentation step of the production process is desirable, for example, for production economy considerations.

The fusion protein inclusion body containing the main chain of the GPL-1 compound is denatured and renatured to obtain the fusion protein of correct conformation, which is then subjected to a series of treatments such as enzyme digestion, precipitation regulation and centrifugation to obtain the main chain of the GLP-1 compound with relatively high content. After purifying by ion exchange chromatograph, the main chain of the GLP-1 compound with relatively high purity is obtained.

The term "excipient" broadly refers to any ingredient other than the active therapeutic ingredient.

The excipient may be inert substances, inactive substances and/or non-pharmaceutically active substances.

The excipient may be used for a variety of purposes, for example as carriers, vehicles, diluents, tablet aids, and/or for improving administration and/or absorption of the active substances.

The formulation of pharmaceutically active ingredients with different excipients is known in the art, see, e.g., Remington: The Science and Practice of Pharmacy (e.g., 19th edition (1995), and any later versions).

Non-limiting examples of excipients are solvents, diluents, buffers, preservatives, isotonic agents, chelating agents and stabilizers.

The GLP-1 derivatives and analogues disclosed herein have GLP-1 activity. "Having GLP-1 activity" refers to the ability to bind to the GLP-1 receptor and trigger a signal transduction pathway to produce insulinotropic action or other physiological effects.

In a specific embodiment, potency, efficacy and/or activity refers to in vitro efficacy, i.e., performance in a functional GLP-1 receptor assay, particularly the ability to stimulate cAMP to form in a cell line expressing a cloned human GLP-1 receptor.

In another specific embodiment, the derivatives disclosed herein are potent in vivo, and can be determined in any suitable animal model and in clinical trials according to the method known in the art. For example, diabetic db/db mice are one example of suitable animal models in which the hypoglycemic effect can be determined, for example, as described in the section "Examples" of the present invention.

The term "insulin" encompasses natural insulins, such as human insulin and insulin analogues and insulin derivatives thereof.

The term "insulin analogue" encompasses polypeptides having a molecular structure which may be formally derived from the structure of a natural insulin, e.g., human insulin, by deletion and/or replacement of one or more amino acid residues present in the natural insulin and/or by addition of at least one amino acid residue. Preferably, the amino acid residue for substitution is an encodable amino acid residue.

Herein, the term "insulin derivative" refers to a natural insulin or insulin analogue which has been chemically modified, and the modification may be, for example, introducing a side chain at one or more positions of the insulin backbone, oxidizing or reducing groups of amino acid residues on the insulin, converting a free carboxyl group into an ester group, or acylating a free amino group or a hydroxyl group. The acylated insulin of the present invention is an insulin derivative.

The term "insulin parent" refers to an insulin moiety of an insulin derivative or an acylated insulin (also referred to herein as parent insulin), and for example, refers to a moiety of an acylated insulin without an added acyl group in the present invention. The insulin parent may be a natural insulin, such as human insulin or porcine insulin. In another aspect, the parent insulin may be an insulin analogue.

Herein, the term "amino acid residue" encompasses amino acids from which a hydrogen atom has been removed from an amino group and/or a hydroxyl group has been removed from a carboxyl group and/or a hydrogen atom has been removed from a mercapto group. Imprecisely, an amino acid residue may be referred to as an amino acid.

Unless otherwise stated, all amino acids referred to herein are L-amino acids.

Herein, the term "alkylene glycol" comprises oligo- and poly-alkylene glycol moieties and monoalkylene glycol moieties. Monoalkylene glycols and polyalkylene glycols include, for example, chains based on monoethylene and polyethylene glycols, monopropylene and polypropylene glycols, and monotetramethylene and polytetramethylene glycols, i.e., chains based on the repeating unit $—CH_2CH_2O—$, $—CH_2CH_2CH_2O—$ or $—CH_2CH_2CH_2CH_2O—$. The alkylene glycol moiety can be monodisperse (with well-defined length/molecular weight) and polydisperse (with less well-defined length/average molecular weight). The monoalkylene glycol moiety includes $—OCH_2CH_2O—$, $—OCH_2CH_2CH_2O—$ or $—OCH_2CH_2CH_2CH_2O—$ comprising different groups at each end.

The term "fatty acid" includes linear or branched fatty carboxylic acids having at least two carbon atoms and being saturated or unsaturated. Non-limiting examples of fatty acids are, for example, myristic acid, palmitic acid, stearic acid, and eicosanoic acid.

Herein, the term "fatty diacid" includes linear or branched fatty dicarboxylic acids having at least two carbon atoms and being saturated or unsaturated. Non-limiting examples of fatty diacids are hexanedioic acid, octanedioic acid, decanedioic acid, dodecanedioic acid, tetradecanedioic acid, hexadecanedioic acid, heptadecanedioic acid, octadecanedioic acid, eicosanedioic acid, docosanedioic acid and tetracosanedioic acid.

As used herein, the naming of insulin or GLP-1 compounds follows the following principle: the names are given according to mutations and modifications (e.g., acylation) relative to human insulin, or mutations and modifications (e.g., acylation) of natural GLP-1(7-37). The naming of the acyl moieties is based on the IUPAC nomenclature and, in other cases, the peptide nomenclature. For example, the following acyl moiety:

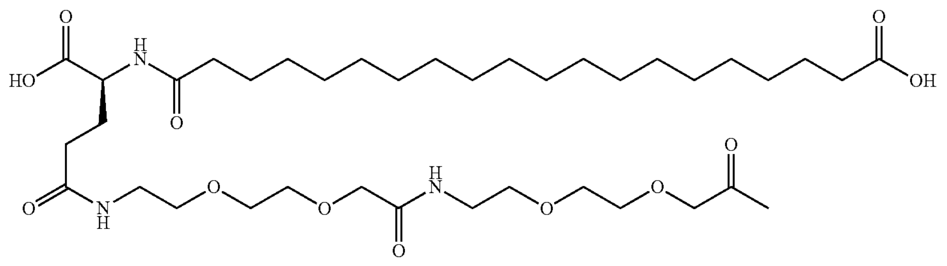 [SMILES: CC(=O)COCCOCCNC(=O)COCCOCCNC(=O)CC[C@H](NC(=O)CCCCCCCCCCCCCCCCCCC(=O)O)C(=O)O]

can be named, for example, as "eicosanedioyl-γGlu-OEG-OEG", "eicosanedioyl-γGlu-2×OEG" or "eicosanedioyl-gGlu-2×OEG", "19-carboxynonadecanoyl-γGlu-2×OEG" or "19-carboxynonadecanoyl-γGlu-OEG-OEG", wherein OEG is the shorthand for the group $—NH(CH_2)_2O(CH_2)_2OCH_2CO—$ (i.e., 2-[2-(2-aminoethoxy)ethoxy]acetyl) and γGlu (or gGlu) is the shorthand for the amino acid γ-glutamic acid in the L configuration. Alternatively, the acyl moieties may be named according to IUPAC nomenclature (OpenEye, IUPAC format). According to this nomenclature, the above acyl moiety of the present invention is referred to as the following name: "[2-[2-[2-[2-[2-[2-[(4S)-4-carboxy-4-(19-carboxynonadecanoylamino)butanoyl]-amino]-ethoxy]-ethoxy]acetyl]amino]ethoxy]ethoxy]acetyl]" or "[2-(2-[2-(2-[2-(2-[4-(19-carboxynonadecanoylamino)-4(S)-carboxybutanoylamino]ethoxy)ethoxy]acetylamino)ethoxy]ethoxy)acetyl]".

For example, the insulin of Example 6 of the present invention (having the sequence/structure given below) is referred to as "B29K(N(ε)-eicosanedioyl-γGlu-5×OEG), desB30 human insulin", "B29K(Nε-eicosanedioyl-γGlu-5×OEG), desB30 human insulin", or "B29K(Nε-eicosanedioyl-gGlu-5×OEG), desB30 human insulin", which indicates that the amino acid K at position B29 in human insulin has been modified by acylation with the residue eicosanedioyl-gGlu-2×OEG on the ε nitrogen (referred to as Nε or (N(ε)) of the lysine residue at position B29, and that the amino acid T at position B30 in human insulin has been deleted. For another example, the insulin of Comparative Example 5 (having the sequence/structure given below) is referred to as "A14E, B16H, B25H, B29K(Nε-eicosanedioyl-gGlu-2×OEG), desB30 human insulin" or "A14E, B16H, B25H, B29K(N(ε)-eicosanedioyl-γGlu-2×OEG), desB30 human insulin", which indicates that amino acid Y at position A14 in human insulin has been mutated to E, amino acid Y at position B16 in human insulin has been mutated to H, amino acid F at position B25 in human insulin has been mutated to H, amino acid K at position B29 in human insulin has been modified by acylation with the residue eicosanedioyl-gGlu-2×OEG on the ε nitrogen (referred to as Nε) of the lysine residue at position B29, and that the amino acid T at position B30 in human insulin has been deleted.

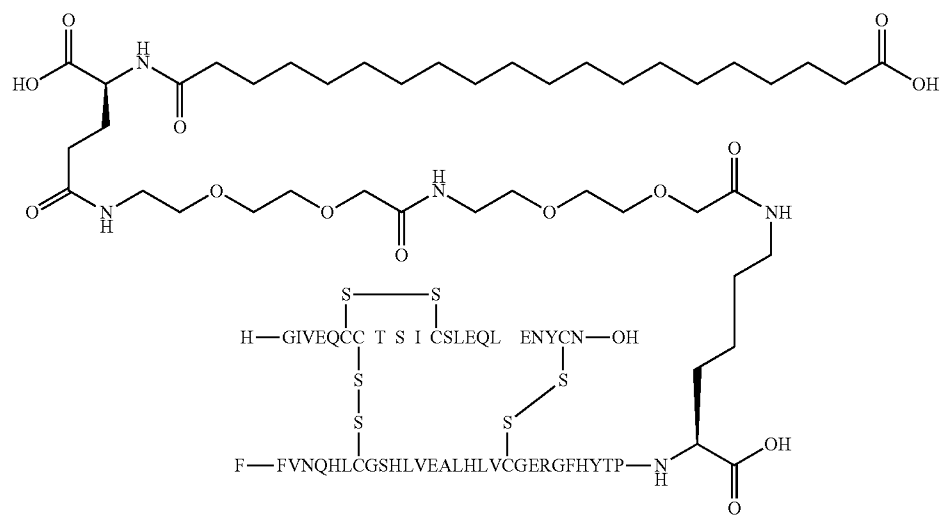

As used herein, "n×PEG" refers to —$NH(CH_2CH_2O)_nCH_2CO$—, where n is an integer. For example, "12×PEG" refers to the group —$NH(CH_2CH_2O)_{12}CH_2CO$—.

Insulin is a polypeptide hormone secreted by β cells in the pancreas and is composed of two polypeptide chains, namely A chain and B chain, linked by two inter-chain disulfide bonds. In addition, the A chain is characterized by having an intra-chain disulfide bond.

There are three main methods for preparing human insulin in microorganisms. Two of those methods involve *E. coli*, one by expressing fusion proteins in the cytoplasm (Frank et al. (1981) in Peptides: Proceedings of the 7th American Peptide Chemistry Symposium (Rich & Gross, eds.), Pierce Chemical Co., Rockford, III, pp. 729-739), and the other by enabling the secretion of a signal peptide into the periplasmic space (Chan et al. (1981) *PNAS* 78:5401-5404). The third method involves enabling the secretion of an insulin precursor into the medium by means of *Saccharomyces cerevisiae* (Thim et al. (1986) *PNAS* 83:6766-6770). A number of methods for the expression of insulin precursors in *E.coli* or *Saccharomyces cerevisiae* have been disclosed in the prior art. See, e.g., U.S. Pat. No. 5,962,267, WO95/16708, EP0055945, EP0163529, EP0347845 and EP0741188.

Construction of a vector, expression, processing and purification of an insulin analogue can be carried out using techniques well known to those skilled in the art. For example, the insulin analogue can be prepared by expressing a DNA sequence encoding the insulin analogue of interest in a suitable host cell by well-known techniques disclosed in U.S. Pat. No. 6,500,645. For example, insulin analogues can also be prepared by methods reported in the following paper: Glendorf T, Sørensen A R, Nishimura E, Pettersson I, & Kjeldsen T: Importance of the Solvent-Exposed Residues of the Insulin B Chain a-Helix for Receptor Binding; *Biochemistry,* 2008, 47:4743-4751. In this paper, mutations are introduced into an insulin-encoding vector using overlap extension PCR. Insulin analogues are expressed in *Saccharomyces cerevisiae* strain MT663 as proinsulin-like fusion proteins with an Ala-Ala-Lys mini C-peptide. The single-chain precursors are enzymatically converted into two-chain desB30 analogues using *A. lyticus* endoprotease.

Isolated insulin analogues can be acylated at the desired position by acylation methods well known in the art, and examples of such insulin analogues are described in, for example, Chinese Patent Application Publication Nos. CN1029977C, CN1043719A and CN1148984A.

Nucleic acid sequences encoding polypeptides of the insulin analogues can be prepared synthetically by established standard methods, for example, by the method described in Beaucage et al. (1981) *Tetrahedron Letters* 22:1859-1869 or Matthes et al. (1984) *EMBO Journal* 3:801-805.

The present invention will be further illustrated by the following examples. It should be noted that the examples are not intended to limit the scope of the present invention.

EXAMPLES

Abbreviation

CAMP: cyclic adenosine monophosphate;
BHK: baby hamster kidney cells;
DNA: deoxyribonucleic acid;
$NazHPO_4$: disodium hydrogen phosphate;
NaOH: sodium hydroxide;
OEG: the amino acid residue —$NH(CH_2)_2O(CH_2)_2OCH_2CO$—;
OSu: succinimidyl-1-yloxy-2,5-dioxo-pyrrolidin-1-yloxy;
OtBu: oxy-tert-butyl;
HCl: hydrogen chloride;
γGlu or gGlu: γL-glutamoyl;
NHS: N-hydroxysuccinimide;
DCC: dicyclohexylcarbodiimide;
AEEA: 2-(2-(2-aminoethoxy)ethoxy)acetic acid;
OH: hydroxyl;
Gly: glycine;
Arg: arginine;
TFA: trifluoroacetic acid;
HbA1c: glycated hemoglobin.

Example 1

Title Compound: N-$\varepsilon^{26}$-[2-(2-[2-(2-[2-(2-[4-(19-carboxynonadecanoylamino)-4(S)-carboxybutanoylamino]ethoxy)ethoxy]acetylamino)ethoxy]ethoxy)acetyl][Gly8, Arg34]GLP-1-(7-37) peptide (Compound 1)

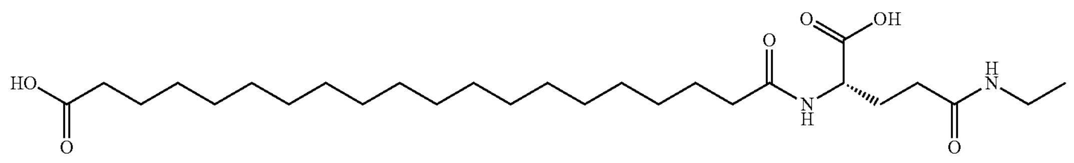

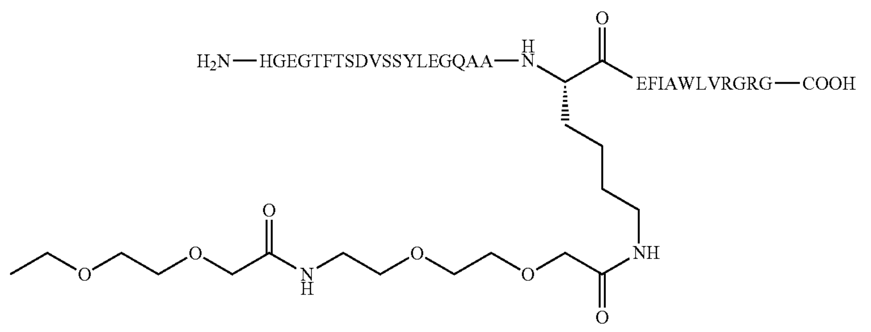

1. Preparation of N-$\varepsilon^{26}$-[2-(2-[2-(2-[2-(2-[4-(19-carboxynonadecanoylamino)-4(S)-carboxybutanoylamino]ethoxy)ethoxy]acetylamino)ethoxy]ethoxy)acetyl][Gly8, Arg34]GLP-1-(7-37) Peptide

[Gly8, Arg34]GLP-1-(7-37) peptide was prepared by a general protein recombinant expression method (for details, see Molecular Cloning: A Laboratory Manual (Fourth Edition), Michael R. Green, Cold Spring Harbor Press, 2012). [Gly8, Arg34]GLP-1-(7-37) peptide (5 g, 1.48 mmol) was dissolved in 100 mM aqueous $Na_2HPO_4$ solution (150 mL) and acetonitrile (100 mL) was added. The pH was adjusted to 10-12.5 with 1 N NaOH. Tert-butyl eicosanedioyl-γGlu (2×OEG-OSu)-OtBu (1.59 g, 1.63 mmol) was dissolved in acetonitrile (50 mL), and the solution was slowly added to a [Gly8, Arg34]GLP-1-(7-37) peptide solution. The pH value was maintained at 10-12.5. After 120 min, the reaction mixture was added to water (150 mL), and the pH value was adjusted to 5.0 with 1 N aqueous HCl. The precipitate was separated out by centrifugation and lyophilized. The crude product was added to a mixed solution of trifluoroacetic acid (60 mL) and dichloromethane (60 mL), and the mixture was stirred at room temperature for 30 min. The mixture was then concentrated to about 30 mL and poured into ice-cold n-heptane (300 mL), and the precipitated product was isolated by filtration and washed twice with n-heptane. The resulting precipitate was dried in vacuum and purified by ion exchange chromatography (Resource Q, 0.25%-1.25% ammonium acetate gradient in 42.5% ethanol, pH 7.5) and reverse phase chromatography (acetonitrile, water, TFA). The purified fractions were combined, adjusted to pH value 5.2 with 1 N HCl, and separated to obtain the precipitate, which was lyophilized to obtain the title compound.

LC-MS (ESI): m/z=1028.79$[M+4H]^{4+}$

2. Preparation of Intermediate Tert-Butyl Eicosanedioyl-γGlu-(2×OEG-OSu)-OtBu 2.1 Tert-Butyl Eicosanedioyl-OSu Eicosanedioic acid mono-tert-butyl ester (20 g, 50.17 mmol) and NHS (5.77 g, 50.17 mmol) were mixed in dichloromethane (400 mL) under nitrogen atmosphere, and triethylamine (13.95 mL) was added. The resulting turbid mixture was stirred at room temperature, added with DCC (11.39 g, 55.19 mmol) and further stirred overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-OSu (24.12 g, yield 97%).

LC-MS (Scie×100 API): m/z=496.36$(M+1)^+$ 2.2 Tert-Butyl Eicosanedioyl-γGlu-OtBu Tert-butyl eicosanedioyl-OSu (24.12 g, 48.66 mmol) was dissolved in dichloromethane (250 mL), and the solution was stirred and added with H-Glu-OtBu (10.88 g, 53.53 mmol), triethylamine (12.49 mL) and water (25 mL) sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-OtBu (27.27 g, yield 96%).

LC-MS (Sciex100 API): m/z=584.44$(M+1)^+$ 2.3 Tert-Butyl Eicosanedioyl-γGlu-(OSu)-OtBu Tert-butyl eicosanedioyl-γGlu-OtBu (27.27 g, 46.71 mmol) was dissolved in dichloromethane (300 mL) under nitrogen atmosphere, and triethylamine (11.99 mL) was added. The mixture was stirred for 10 min, and NHS (5.38 g, 50.17 mmol) was added, followed by the addition of DCC (10.60 g, 51.38 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure. Tert-butyl methyl ether was added, and the mixture was stirred for 30 min and filtered in vacuum. The filter cake was dried in vacuum overnight to obtain tert-butyl eicosanedioyl-γGlu-(OSu)-OtBu (25.76 g, yield 81%).

LC-MS (Sciex100 API): m/z=681.46$(M+1)^+$ 2.4 Tert-Butyl Eicosanedioyl-γGlu-(2×OEG-OH)-OtBu Tert-butyl eicosanedioyl-γGlu-(OSu)-OtBu (25.76 g, 37.83 mmol) was dissolved in dichloromethane (250 mL), and the solution was stirred and added with 2×AEEA (11.66 g, 37.83 mmol), triethylamine (9.71 mL) and water (25 mL) sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-(2×OEG-OH)-OtBu (30.75 g, yield 93%).

LC-MS (Sciex100 API): m/z=874.59$(M+1)^+$ 2.5 Tert-Butyl Eicosanedioyl-γGlu-(2×OEG-OSu)-OtBu Tert-butyl eicosanedioyl-γGlu-(2×OEG-OH)-OtBu (30.75 g, 35.18 mmol) was dissolved in dichloromethane (300 mL) under nitrogen atmosphere, and triethylamine (9.03 mL) was added. The mixture was stirred for 10 min, and NHS (4.05 g, 35.18 mmol) was added, followed by the addition of DCC (7.98 g, 38.70 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-γGlu-(2×OEG-OSu)-OtBu (31.09 g, yield 91%).

LC-MS (Sciex100 API): m/z=971.61$(M+1)^+$

Example 2

Title Compound: N-$\varepsilon^{26}$-[2-(2-[2-(4-[19-carboxynonadecanoylamino]-4(S)-carboxybutanoylamino)ethoxy]ethoxy)acetyl][Gly8, Arg34]GLP-1-(7-37) Peptide (Compound 2)

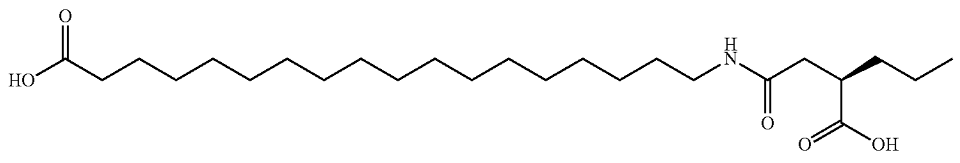

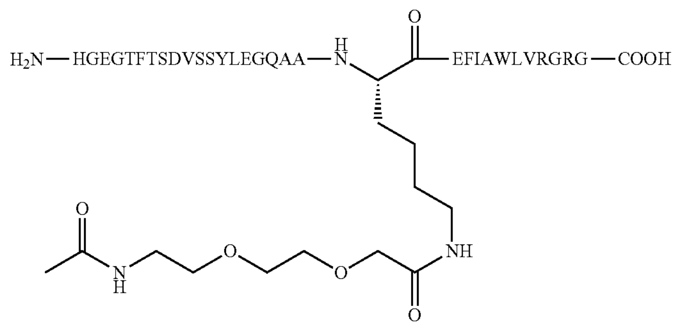

N -$\varepsilon^{26}$-[2-(2-[2-(4-[19-carboxynonadecanoylamino]-4(S)-carboxybutanoylamino)ethoxy]ethoxy)acetyl][Gly8, Arg34]GLP-1-(7-37) peptide was prepared by procedures similar to those described in section 1 of Example 1.

LC-MS (ESI): m/z=992.52$[M+4H]^{4+}$

The intermediate tert-butyl eicosanedioyl-γGlu-(OEG-OSu)-OtBu was prepared by procedures similar to those described in section 2 of Example 1.

LC-MS (Sciex100API): m/z=826.54(M+1)+

Example 3

Title Compound: N-$\varepsilon^{26}$-(19-carboxynonadecanoylamino)-4(S)-carboxybutanoyl-[Gly8, Arg34]GLP-1-(7-37) Peptide (Compound 3)

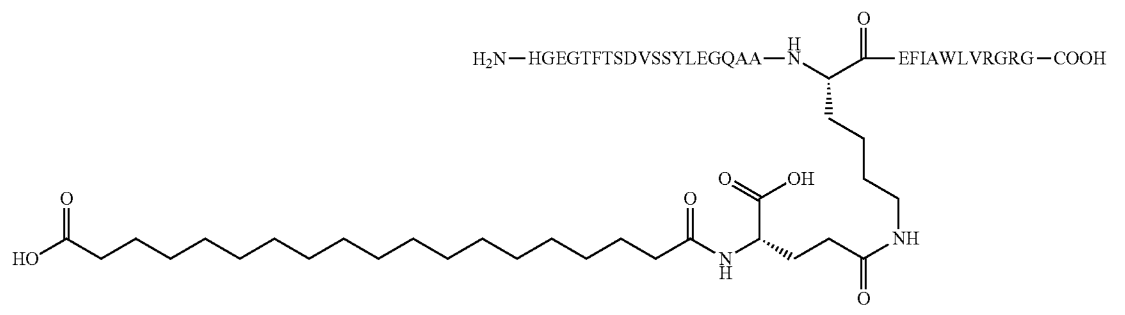

N-$\varepsilon^{26}$-(19-carboxynonadecanoylamino)-4(S)-carboxybutanoyl-[Gly8, Arg34]GLP-1-(7-37) peptide was prepared by procedures similar to those described in section 1 of Example 1.

LC-MS (ESI): m/z=956.25$[M+4H]^{4+}$

The intermediate tert-butyl eicosanedioyl-γGlu-(OSu)-OtBu was prepared by procedures similar to those described in section 2 of Example 1.

LC-MS (Sciex100 API): m/z=681.46$(M+1)^{+}$

Example 4

Title Compound: N-$\varepsilon^{26}$-(19-carboxynonadecanoylamino)-4(S)-carboxybutanoyl-[Arg34]GLP-1-(7-37) Peptide (Compound 4)

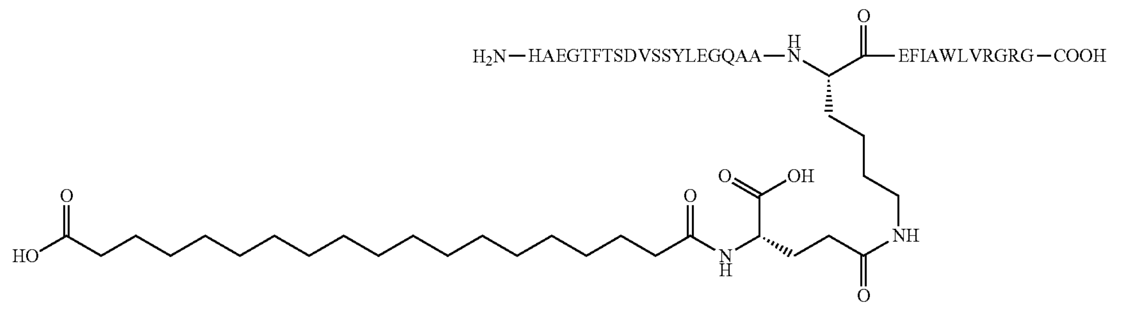

N-$\varepsilon^{26}$-(19-carboxynonadecanoylamino)-4(S)-carboxybutanoyl-[Arg34]GLP-1-(7-37) peptide was prepared by procedures similar to those described in section 1 of Example 1.

LC-MS (ESI): m/z=959.75$[M+4H]^{4+}$

The intermediate tert-butyl eicosanedioyl-γGlu-(OSu)-OtBu was prepared by procedures similar to those described in section 2 of Example 1.

LC-MS (Sciex100 API): m/z=681.46(M+1)$^+$

Comparative Example 1

The control compound liraglutide was prepared according to Example 37 of patent CN1232470A.

Comparative Example 2

The control compound semaglutide was prepared according to Example 4 of patent CN101133082A.

Comparative Example 3

Title Compound: N -ε$^{26}$-[2-(2-[2-(2-[2-(2-[4-(17-carboxyheptadecanoylamino)-4(S)-carboxybutanoylamino] ethoxy)ethoxy]acetylamino)ethoxy]ethoxy) acetyl][Gly8, Arg34]GLP-1-(7-37) Peptide

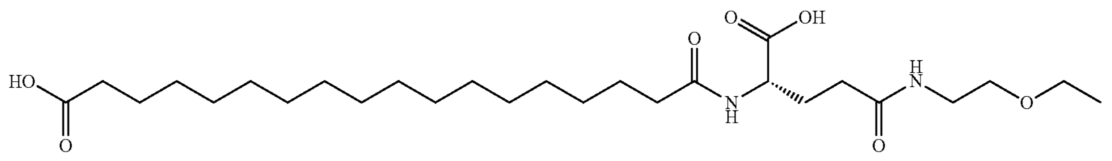

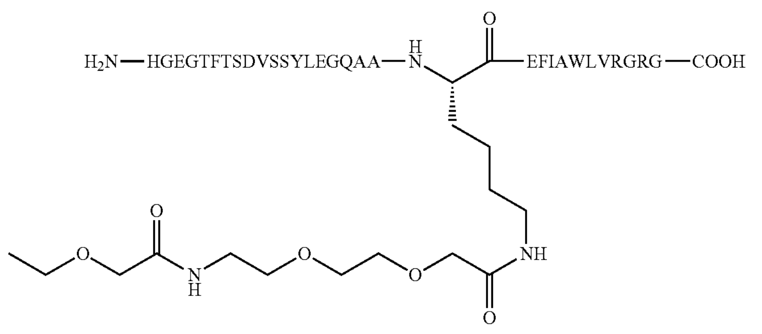

N-ε$^{26}$-[2-(2-[2-(2-[2-(2-[4-(17-carboxyheptadecanoylamino)-4(S)-carboxybutanoylamino]ethoxy)ethoxy]acetylamino)ethoxy]ethoxy)acetyl][Gly8, Arg34]GLP-1-(7-37) peptide was prepared by procedures similar to those described in section 1 of Example 1.

LC-MS (ESI): m/z=1021.78[M+4H]$^{4+}$

Comparative Example 4

Title Compound: N -ε$^{26}$-(17-carboxyheptadecanoylamino)-4(S)-carboxybutanoyl-[Gly8, Arg34]GLP-1-(7-37) Peptide

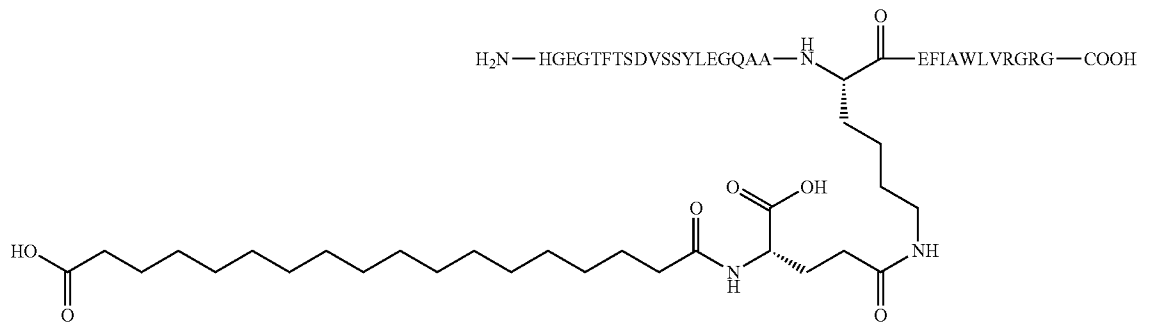

N-ε[26]-(17-carboxyheptadecanoylamino)-4(S)-carboxybutanoyl-[Gly8, Arg34]GLP-1-(7-37) peptide was prepared by procedures similar to those described in section 1 of Example 1.

LC-MS (ESI): m/z=949.24$[M+4H]^{4+}$

The intermediate tert-butyl octadecanedioyl-γGlu-(OSu)-OtBu was prepared by procedures similar to those described in section 2 of Example 1.

LC-MS (Sciex100 API): m/z=653.43$(M+1)^+$

Example 5. Pharmacodynamic Study on db/db Mice

This study was intended to demonstrate the regulatory effect of the GLP-1 derivatives disclosed herein on hyperglycemia (BG) in the case of diabetes.

The title compounds of Examples 1-4 and Comparative Examples 1-4 (also known as GLP-1 derivatives) were tested in a single dose study on an obese mouse model (db/db mice) with type 2 diabetes (T2DM). The hypoglycemic drug effect of the GLP-1 derivatives was tested at a dose of 100 μg/kg.

Male db/db (BKS/Lepr) mice aged 8-9 weeks were housed in appropriately sized feeding cages in a barrier environment and had free access to standard food and purified water, with environmental conditions controlled at 40%-60% relative humidity (RH) and 22-24° C. After an adaptation period of 1-2 weeks, the mice were used in the experiment.

Before the start of the experiment on the day, the mice were evaluated for baseline blood glucose at about 9:30 a.m. and weighed. Mice were each distributed to either the vehicle group or the treatment group based on random blood glucose and body weight, and subjected to the following treatments: subcutaneous injection of the vehicle or the GLP-1 derivatives (100 μg/kg), wherein the vehicle contained 14 mg/mL propylene glycol, 5.5 mg/mL phenol and 1.133 mg/mL disodium hydrogen phosphate, with a pH value of 8.12.

The GLP-1 derivatives were dissolved in the vehicle to an administration concentration of 20 μg/mL, and the administration volume was 5 mL/kg (i.e., 50 μL/10 g body weight). The administration was performed once by subcutaneous injection (s.c.) at back of the neck. The corresponding GLP-1 derivatives were administered at about 10:30 a.m. (time 0), and during the treatment, the animals had free access to food and water. The blood glucose of the mice was evaluated 2 h, 4 h, 6 h, 8 h, 10 h, 12 h, 24 h, 48 h and 72 h after the administration. The tail of each mouse was cleaned with an alcohol cotton ball, and blood drops were collected from the tail using a disposable blood collection needle and measured with a glucometer and accompanying testing strips (Roche). Food intake and body weight of each mouse were measured at 24 h, 48 h and 72 h after the administration.

The percentage of blood glucose at each monitoring point was obtained by dividing the blood glucose at the corresponding time point after the administration by the baseline blood glucose before the administration; the dose-response curve of percentage of blood glucose versus time was plotted for each single dose of GLP-1 derivative; in order to quantify the effect of GLP-1 derivatives on blood glucose, the area under the curve of the percentage of blood glucose versus time from 0 h to 72 h ($AUC_{0\text{-}72h}$) was calculated for each individual dose-response curve. AUC is the area under the curve of time versus the percentage of blood glucose, and the smaller the AUC value, the better the hypoglycemic effect, and the better the drug effect.

FIGS. 1*a*-4*b* show that the GLP-1 derivatives disclosed herein have a surprisingly improved drug effect, for example, the title compounds of Examples 1-4 have a significantly superior hypoglycemic effect on db/db mice to liraglutide and the compounds of Comparative Examples 3-4. In particular, the compound of Example 2 of the present invention has a superior hypoglycemic effect to semaglutide. Furthermore, the effective duration of action of the GLP-1 derivatives disclosed herein, e.g., the compounds of Examples 1-4, on db/db mice is significantly longer than that of liraglutide and the compounds of Comparative Examples 3-4, in particular, the effective duration of action of hypoglycemic effect of the compound of Example 2 on db/db mice is longer than that of semaglutide.

Example 6

B29K(N(ε)-eicosanedioyl-γGlu-5×OEG), desB30 human insulin (Compound 5)

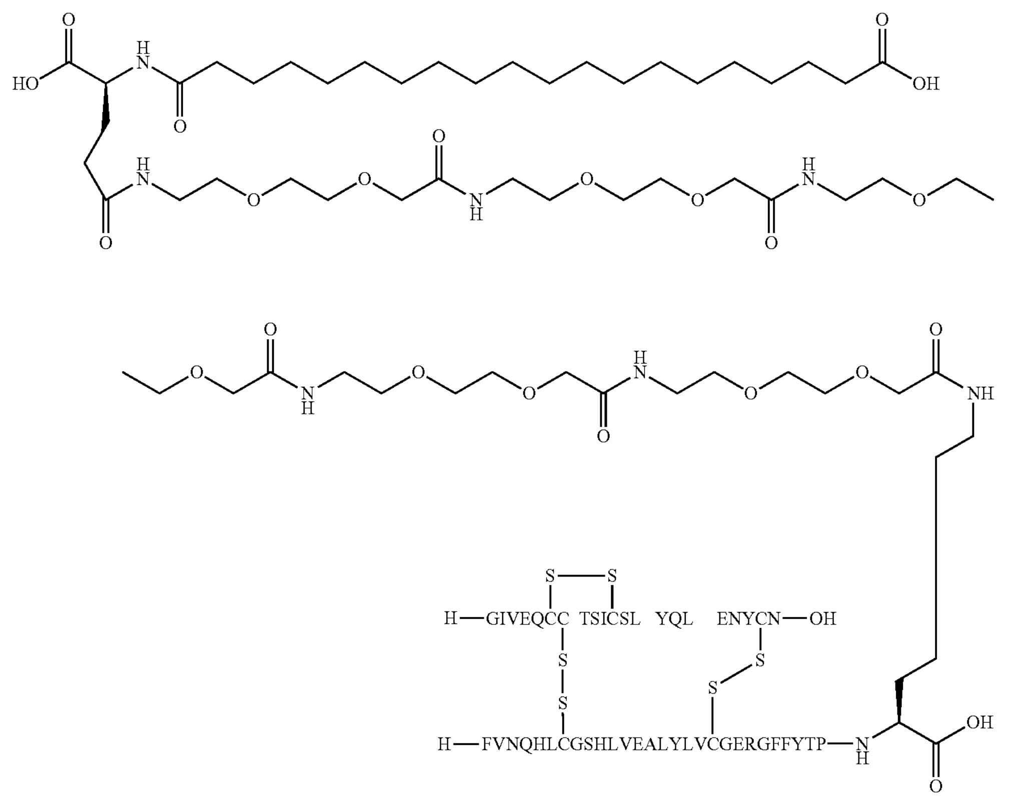

1. Synthesis of des(B30) Human Insulin

Des(B30) human insulin was prepared according to the method described in Example 101 of Chinese Patent CN1056618C.

2. Preparation of Insulin of Interest

DesB30 human insulin (5 g, 0.876 mmol) was dissolved in 100 mM aqueous Na2HPO$_4$ solution (150 mL) and acetonitrile (100 mL) was added. The pH value was adjusted to 10-12.5 with 1 N NaOH. Tert-butyl eicosanedioyl-γGlu-(5×OEG-OSu)-OtBu (1.36 g, 0.964 mmol) was dissolved in acetonitrile (50 mL), and the solution was slowly added to the insulin solution. The pH value was maintained at 10-12.5. After 120 min, the reaction mixture was added to water (150 mL), and the pH value was adjusted to 5.0 with 1 N aqueous HCl. The precipitate was separated out by centrifugation and lyophilized. The crude product was added to a mixed solution of trifluoroacetic acid (60 mL) and dichloromethane (60 mL), and the mixture was stirred at room temperature for 30 min. The mixture was then concentrated to about 30 mL and poured into ice-cold n-heptane (300 mL), and the precipitated product was isolated by filtration and washed twice with n-heptane. The resulting precipitate was dried in vacuum, and purified by ion exchange chromatography (Resource Q, 0.25%-1.25% ammonium acetate gradient in 42.5% ethanol, pH 7.5), and reverse phase chromatography (acetonitrile, water, TFA). The purified fractions were combined, adjusted to pH 5.2 with 1 N HCl, and separated to obtain the precipitate, which was lyophilized to obtain the title compound 5.

LC-MS (ESI): m/z=1377.53$[M+5H]^{5+}$

3. Preparation of Intermediate Tert-Butyl Eicosanedioyl-γGlu-(5×OEG-OSu)-OtBu

3.1 Tert-Butyl Eicosanedioyl-OSu

Eicosanedioic acid mono-tert-butyl ester (20 g, 50.17 mmol) and NHS (5.77 g, 50.17 mmol) were mixed in dichloromethane under nitrogen atmosphere, and triethylamine (13.95 mL) was added. The resulting turbid mixture was stirred at room temperature, added with DCC (11.39 g, 55.19 mmol) and further stirred overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure, and dried in vacuum overnight to obtain tert-butyl eicosanedioyl-OSu (24.12 g, yield 97%).

LC-MS (Sciex100 API): m/z=496.36$(M+1)^+$

3.2 Tert-Butyl Eicosanedioyl-γGlu-OtBu

Tert-butyl eicosanedioyl-OSu (24.12 g, 48.66 mmol) was dissolved in dichloromethane (250 mL), and the solution was stirred and added with H-Glu-OtBu (10.88 g, 53.53 mmol), triethylamine (12.49 mL) and water sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-OtBu (27.27 g, yield 96%).

LC-MS (Sciex100 API): m/z=584.44$(M+1)^+$

3.3 Tert-Butyl Eicosanedioyl-γGlu-(OSu)-OtBu

Tert-butyl eicosanedioyl-γGlu-OtBu (27.27 g, 46.71 mmol) was dissolved in dichloromethane (300 mL) under nitrogen atmosphere, and triethylamine (11.99 mL) was added. The mixture was stirred for 10 min, and NHS (5.38 g, 50.17 mmol) was added, followed by the addition of DCC (10.60 g, 51.38 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure. Tert-butyl methyl ether was added, and the mixture was stirred for 30 min and filtered in vacuum. The filter cake was dried in vacuum overnight to obtain tert-butyl eicosanedioyl-γGlu-(OSu)-OtBu (25.76 g, yield 81%).

LC-MS (Sciex100 API): m/z=681.46$(M+1)^+$

3.4 Tert-Butyl Eicosanedioyl-γGlu-(2×OEG-OH)-OtBu

Tert-butyl eicosanedioyl-γGlu-(OSu)-OtBu (25.76 g, 37.83 mmol) was dissolved in dichloromethane (250 mL), and the solution was stirred and added with 2×AEEA (11.66 g, 37.83 mmol), triethylamine (9.71 mL) and water (25 mL) sequentially. The mixture was heated to obtain a clarified solution, which was then stirred at room temperature for 4 h. Then, the reaction solution was added with 10% aqueous citric acid solution (200 mL), and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain-tert-butyl eicosanedioyl-γGlu-(2×OEG-OH)-OtBu (30.75 g, yield 93%).

LC-MS (Sciex100 API): m/z=874.59$(M+1)^+$

3.5 Tert-Butyl Eicosanedioyl-γGlu-(2×OEG-OSu)-OtBu

Tert-butyl eicosanedioyl-γGlu-(2×OEG-OH)-OtBu (30.75 g, 35.18 mmol) was dissolved in dichloromethane (300 mL) under nitrogen atmosphere, and triethylamine (9.03 mL) was added. The mixture was stirred for 10 min, and NHS (4.05 g, 35.18 mmol) was added, followed by the addition of DCC (7.98 g, 38.70 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-γGlu-(2×OEG-OSu)-OtBu (31.09 g, yield 91%).

LC-MS (Sciex100 API): m/z=971.61$(M+1)^+$

3.6 Tert-Butyl Eicosanedioyl-γGlu-(5×OEG-OH)-OtBu

Tert-butyl eicosanedioyl-γGlu-(2×OEG-OSu)-OtBu (31.09 g, 32.01 mmol) was dissolved in dichloromethane (350 mL), and the solution was stirred and added with 3×AEEA (14.52 g, 32.01 mmol), triethylamine (8.90 mL) and water (25 mL) sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-(5×OEG-OH)-OtBu (38.99 g, yield 93%).

LC-MS (Sciex100 API): m/z=1309.81$(M+1)^+$

3.7 Tert-Butyl Eicosanedioyl-γGlu-(5×OEG-OSu)-OtBu

Tert-butyl eicosanedioyl-γGlu-(5×OEG-OH)-OtBu (38.99 g, 29.77 mmol) was dissolved in dichloromethane (400 mL) under nitrogen atmosphere, and triethylamine (8.28 mL) was added. The mixture was stirred for 10 min, and NHS (3.43 g, 29.77 mmol) was added, followed by the addition of DCC (6.76 g, 32.75 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-γGlu-(5×OEG-OSu)-OtBu (38.11 g, yield 91%).

LC-MS (Sciex100 API): m/z=1406.83$(M+1)^+$

Example 7

B29K(N(ε)-eicosanedioyl-γGlu-6×OEG), desB30 Human Insulin (Compound 6)

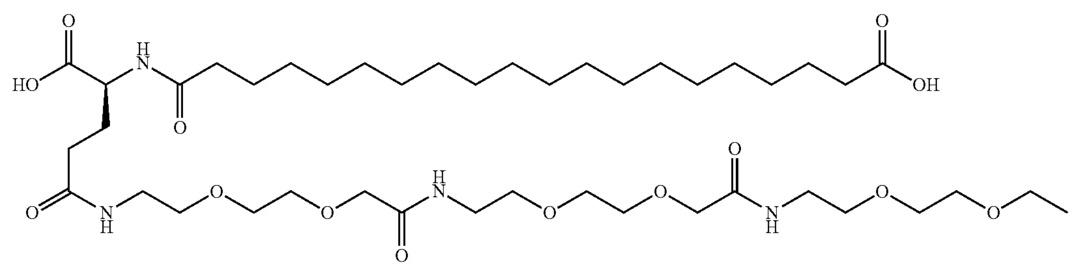
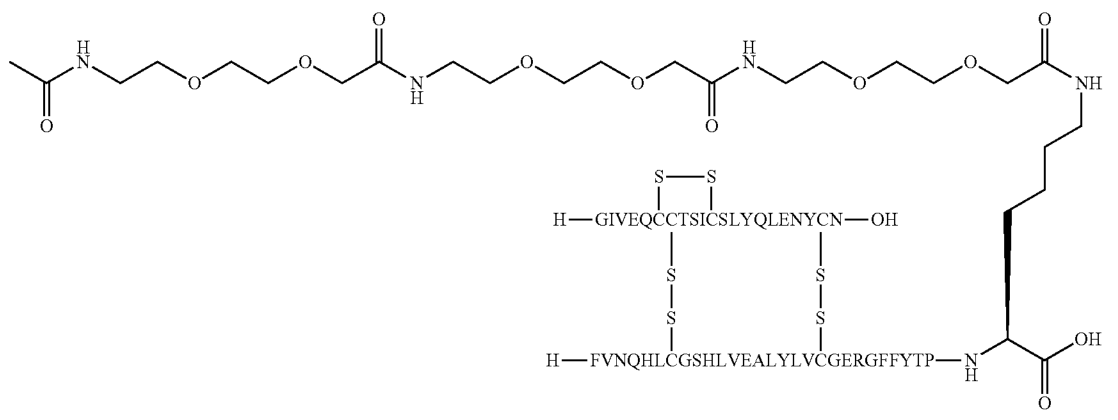
Compound 6 was prepared by procedures similar to those described in section 2 of Example 6.
LC-MS (ESI): m/z=1406.28[M+5H]$^{5+}$
The intermediate tert-butyl eicosanedioyl-γGlu-(6×OEG-OSu)-OtBu was prepared by procedures similar to those described in section 3 of Example 6.
LC-MS (Sciex100 API): m/z=1551.90(M+1)$^{+}$
Example 8
B29K(N(ε)-eicosanedioyl-γGlu-8×OEG), desB30 Human Insulin (Compound 7)
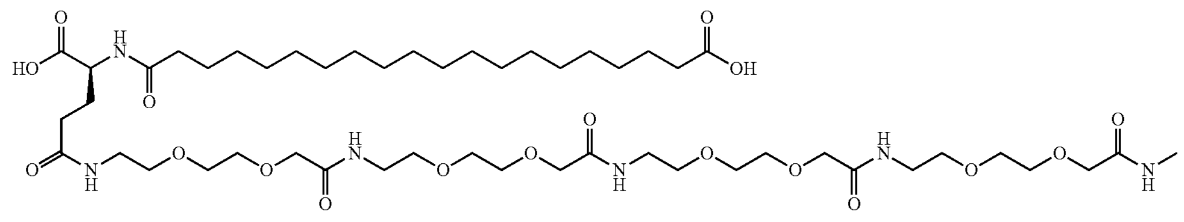

-continued

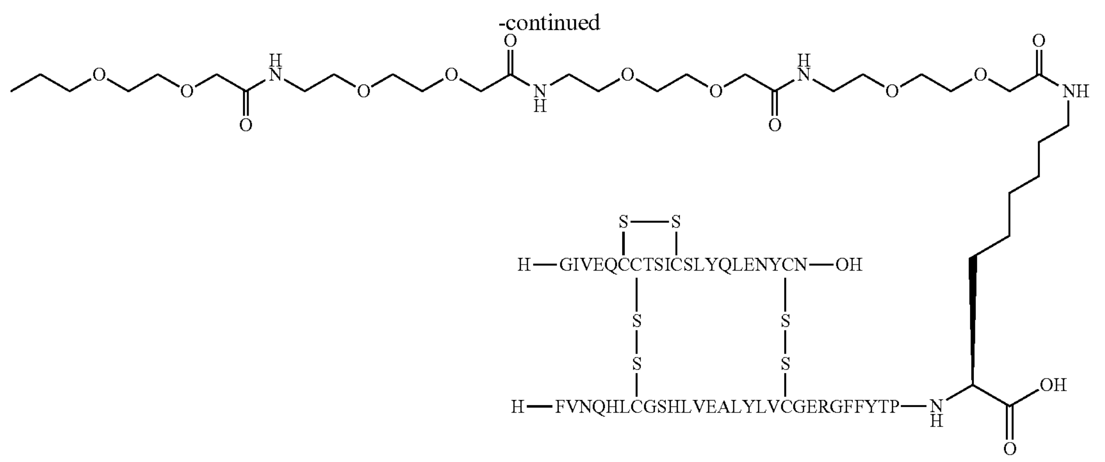

Compound 7 was prepared by procedures similar to those described in section 2 of Example 6.

LC-MS (ESI): m/z=1464.30[M+5H]$^{5+}$

The intermediate tert-butyl eicosanedioyl-γGlu-(8×OEG-OSu)-OtBu was prepared by procedures similar to those described in section 3 of Example 6.

LC-MS (Sciex100 API): m/z=1814.02(M+1)$^{+\cdot}$

Example 9

B29K(N(ε)-docosanedioyl-γGlu-6×OEG), desB30 Human Insulin (Compound 8)

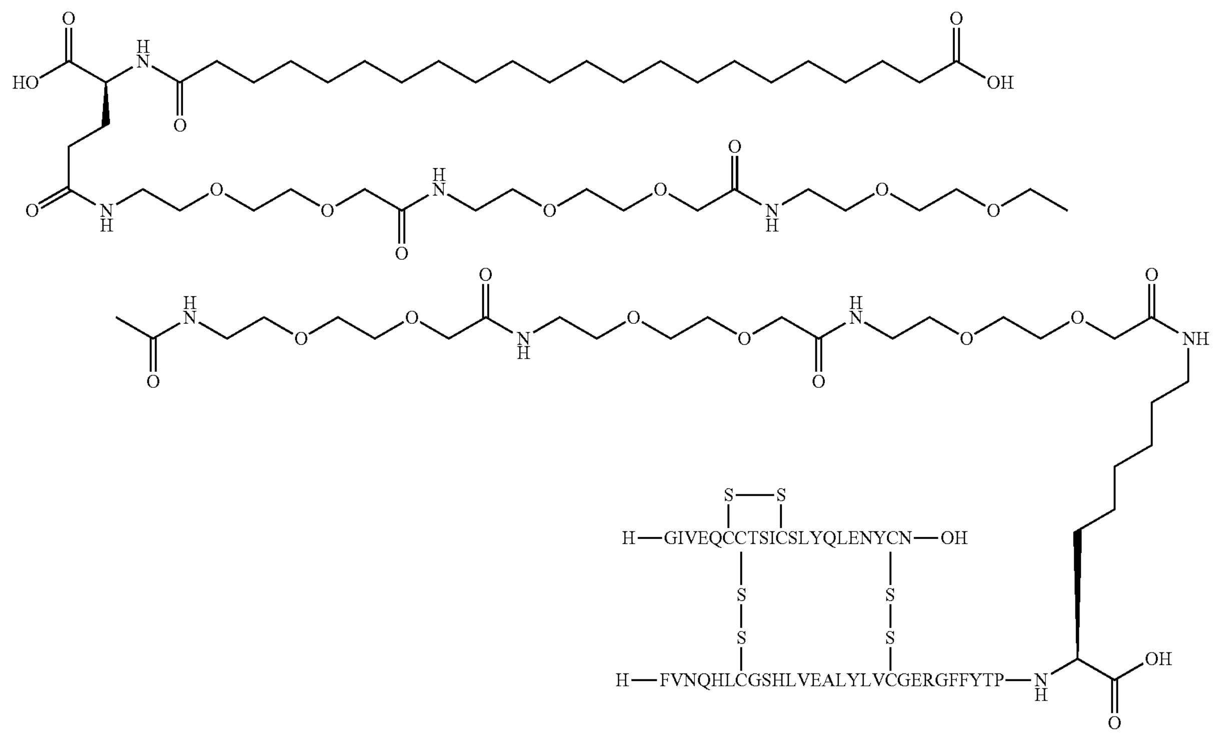

Compound 8 was prepared by procedures similar to those described in section 2 of Example 6.

LC-MS (ESI): m/z=1411.88[M+5H]$^{5+}$

The intermediate tert-butyl docosanedioyl-γGlu-(6×OEG-OSu)-OtBu was prepared by procedures similar to those described in section 3 of Example 6.

LC-MS (Sciex100 API): m/z=1579.94(M+1)$^{+}$

Example 10

B29K(N(ε)-docosanedioyl-γGlu-8×OEG), desB30 Human Insulin (Compound 9)

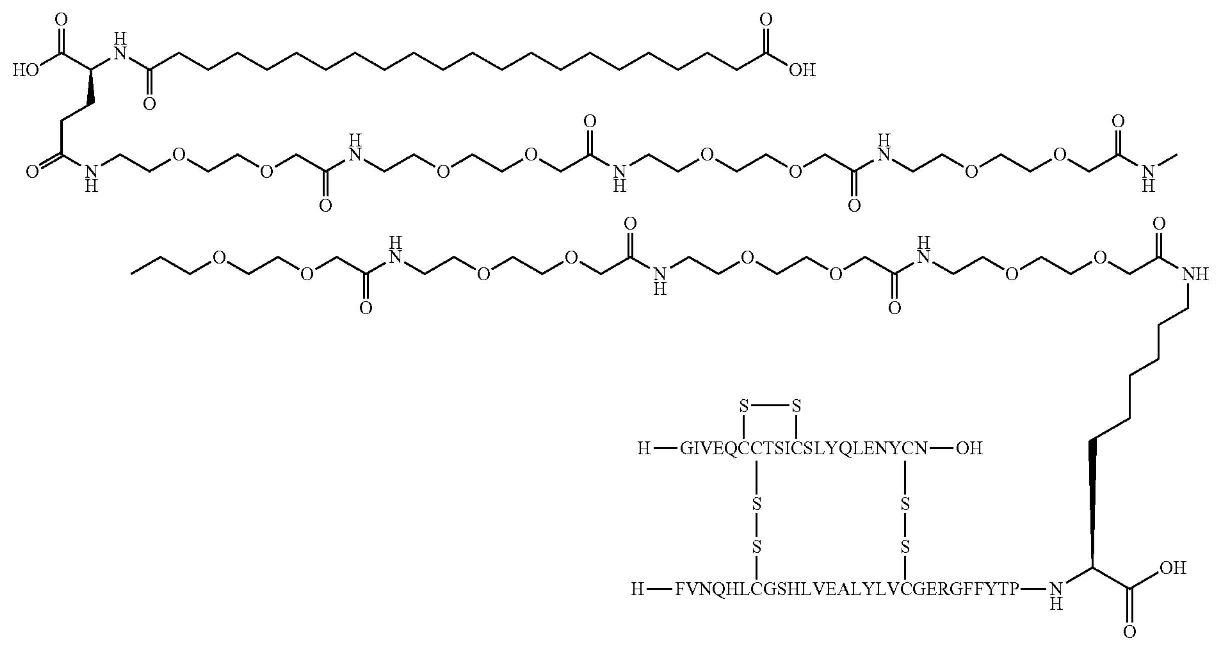

Compound 9 was prepared by procedures similar to those described in section 2 of Example 6.

LC-MS (ESI): m/z=1469.91$[M+5H]^{5+}$

The intermediate tert-butyl docosanedioyl-γGlu-(8×OEG-OSu)-OtBu was prepared by procedures similar to those described in section 3 of Example 6.

LC-MS (Sciex100 API): m/z=1870.08$(M+1)^+$

Example 11

Title Compound: N-$\varepsilon^{26}$-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) Peptide (Compound 10)

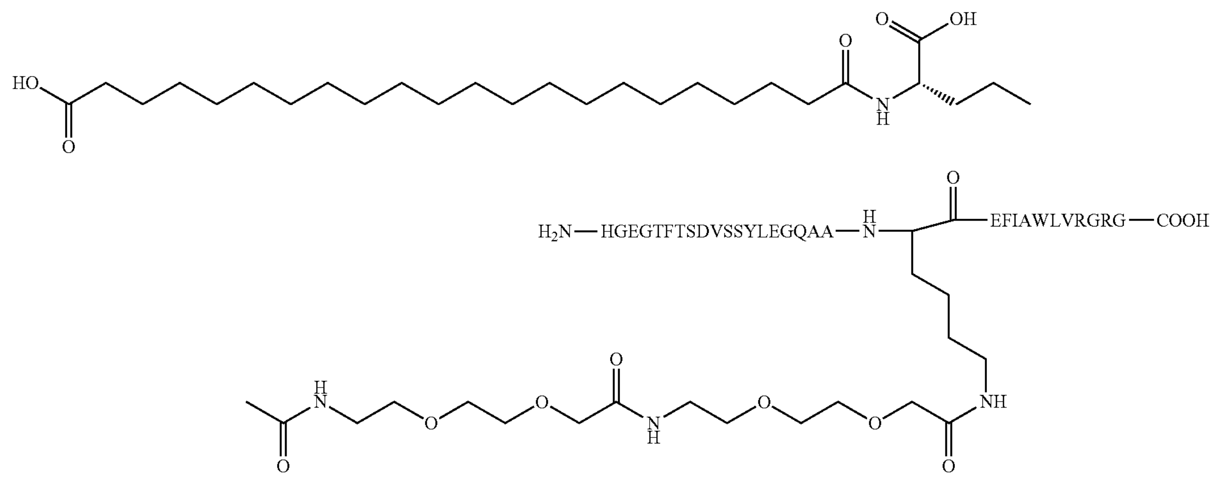

N-ε[26]-[2-(2-[2-(2-[2-(2-[4-(21-carboxyheneicosanoylamino)-4(S)-carboxybutanoylamino]ethoxy)ethoxy]acetylamino)ethoxy]ethoxy)acetyl][Gly8, Arg34]GLP-1-(7-37) peptide was prepared by procedures similar to those described in section 1 of Example 1.

LC-MS (ESI): m/z=1035.80$[M+4H]^{4+}$

The intermediate tert-butyl docosanedioyl-γGlu-(2×OEG-OSu)-OtBu was prepared by procedures similar to those described in section 2 of Example 1.

LC-MS (Sciex100 API): m/z=999.64$(M+1)^+$

Example 12. In Vitro Potency or Activity

This example was intended to test the in vitro potency or activity of the GLP-1 derivatives disclosed herein Cells expressing GLP-1R were thawed, seeded into ham's-F12 medium in a 25 mL cell culture flask, and cultured overnight at 37° C. in 5% $CO_2$. On the day of the experiment, the title compound of Example 11 of the present invention (compound 10) and liraglutide were formulated to 150 μg/mL, and then samples were diluted in a gradient to 750 ng/ml, 150 ng/mL, 30 ng/mL, 6 ng/mL, 1.2 ng/mL, 0.24 ng/mL, 0.048 ng/mL, 0.0096 ng/ml and 0.00192 ng/mL. The cell density was adjusted to $1\times10^5$ cells/mL, and 200 μL of cells and 200 μL of diluted samples were added into each well and mixed well. 100 μL of the mixed sample from each well was pipetted into a new 96-well plate, with 3 replicate wells set for each sample. The cells were cultured for 4 h in a cell incubator, added with a luciferase reagent and shaken to mix well, and the mixture was transferred from the 96-well plate to a new 96-well white flat bottom plate. The signal values were read by a microplate reader, and the data were processed by GraphPad Prism 6 to calculate $EC_{50}$. The in vitro potency experiment was repeated 4 times on different days.

TABLE 1

In vitro potency

| Sample name | $EC_{50}$(nM) |
|---|---|
| liraglutide | 0.439 |
| Compound 10 | 0.677 |

It can be seen from the experimental results that the GLP-1 derivatives disclosed herein have desirable in vitro efficacy, and their in vitro activity is close to that of liraglutide, suggesting that they have agonistic activity of GLP-1 receptors.

Example 13. Pharmacodynamic Study on High Fat Diet-Induced Obese C57BL Mice

This study was intended to demonstrate the blood glucose regulating effect and weight loss effect of the GLP-1 derivatives disclosed herein in high fat diet-induced obese C57BL mice.

C57BL mice (half male and half female) aged 5 weeks and weighing 17-22 g were housed in appropriately sized feeding cages (3-5 mice/box) in a barrier environment. The high fat diet-induction group had free access to high fat feed and purified water, and the normal control group had free access to standard food and purified water, with environmental conditions controlled at 40%-60% RH and 22-24° C. After 10 weeks of feeding, the mice weighing more than 30%-50% of the body weight of the mice in the normal control group were selected for drug effect evaluation.

Before the start of the experiment on the day, the mice were evaluated for baseline blood glucose at time −1/1 h (9:30 a.m.) and weighed. Mice in the high fat diet-induction group were each distributed to either the vehicle group (i.e., the model control group) or the treatment group based on random blood glucose and body weight, and subjected to the following treatments: subcutaneous injection of the vehicle, subcutaneous injection of the control compound semaglutide at 100 μg/kg, or subcutaneous injection of the title compound of Example 11 of the present invention at 100 μg/kg and 300 μg/kg. The vehicle contained 14 mg/mL propylene glycol, 5.5 mg/mL phenol and 1.133 mg/mL disodium hydrogen phosphate, with a pH value of 7.4.

The administration was performed once by subcutaneous administration (s.c., 5 μL/g body weight) at back of the neck. The GLP-1 derivatives were administered at about 10:30 a.m. (time 0), and the blood glucose of the mice was evaluated 3 h, 6 h, 24 h, 48 h and 72 h after the administration. Meanwhile, the body weight of the mice was monitored every day.

The Δ blood glucose-time curve was plotted for each single dose of GLP-1 derivative. Δ refers to the actual blood glucose at a given time minus the baseline, where the baseline is the blood glucose at time 0. Therefore, in those curves, y=0 represents the baseline. For each individual dose-response curve, the difference in area under the blood glucose-time curve (ΔAUC) from time 0 to the monitoring endpoint was calculated. The smaller the ΔAUC value, the better the blood hypoglycemic effect, and the better the drug effect.

An intraperitoneal glucose tolerance test (ipGTT) was performed 48 h after the first administration, and the steps were as follows: blood was collected from the tail tip at the indicated time points to determine fasting blood glucose (0 min), followed by intraperitoneal administration of glucose solutions (200 mg/mL, 10 mL/kg), and then the blood glucose was determined 30 min, 60 min and 120 min after glycemic load.

The tail of each mouse was cleaned with an alcohol cotton ball, and blood drops were collected from the tail using a disposable blood collection needle and measured with a glucometer (Roche) and accompanying testing strips.

The dose-response curve of blood glucose versus time and the dose-response curve of daily body weight change versus time were plotted for each single dose of GLP-1 derivative. In order to more intuitively and quantitatively illustrate the effect of the GLP-1 derivatives disclosed herein on blood glucose, the difference in area under the relative blood glucose-time curve (ΔAUC) from time 0 to the monitoring endpoint was calculated for each individual dose-response curve. The smaller the ΔAUC value, the better the hypoglycemic effect, and the better the drug effect.

Figure 5A:
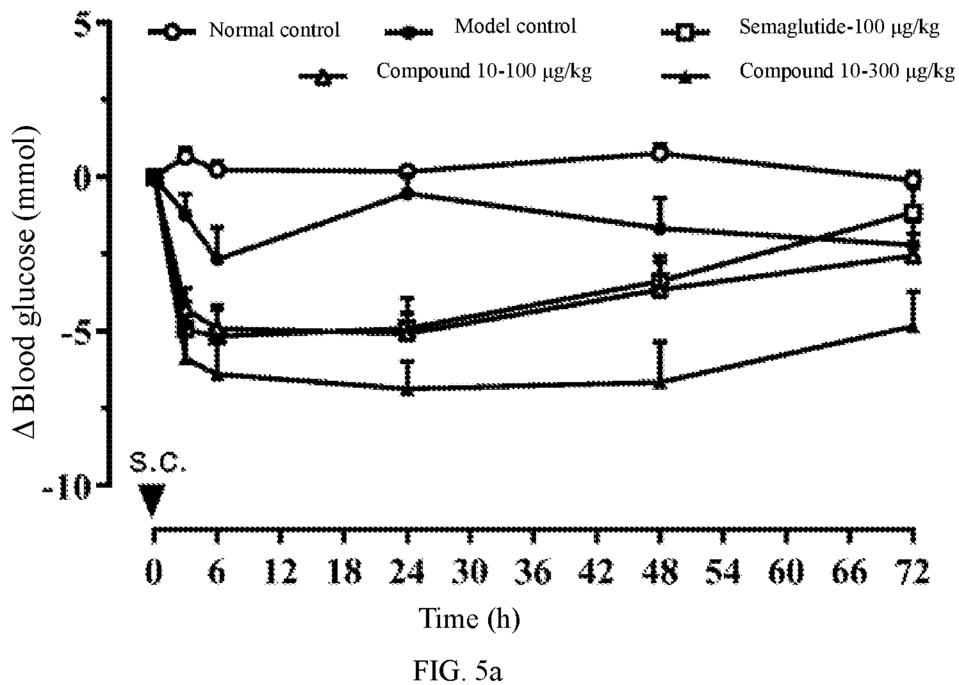
FIG. 5*a* shows the hypoglycemic effect and duration of action of the title compound of Example 11 at doses of 100 μg/kg and 300 μg/kg, the title compound of Comparative Example 2 and vehicle (model control group) on high fat diet-induced obese C57BL mice or normal mice (normal control group) according to the present invention.
Figure 5B:
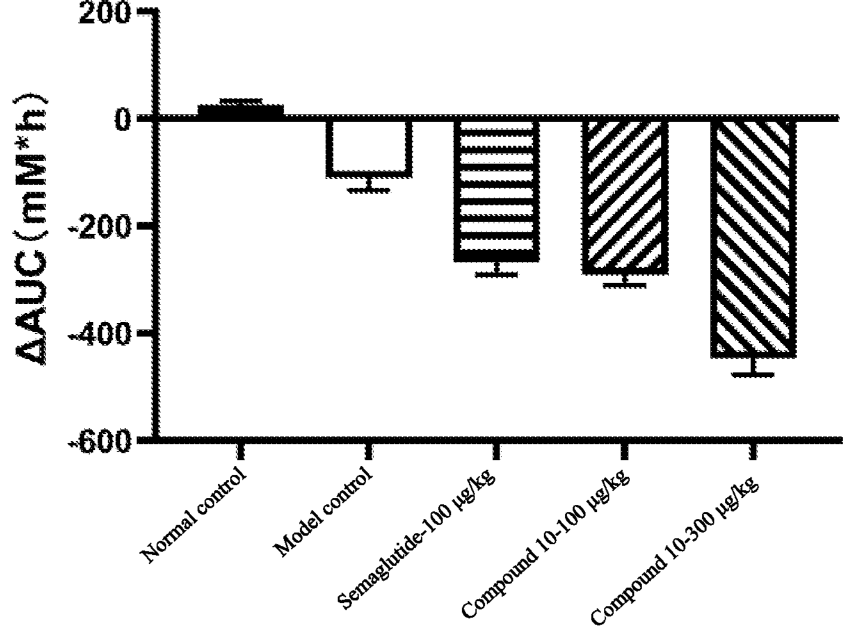
FIG. 5*b* shows, in correspondence with FIG. 5*a*, the AUC of the hypoglycemic effect of the title compound of Example 11, the title compound of Comparative Example 2 and vehicle (model control group) on high fat diet-induced obese C57BL mice or normal mice (normal control group) according to the present invention.
Figure 5C:
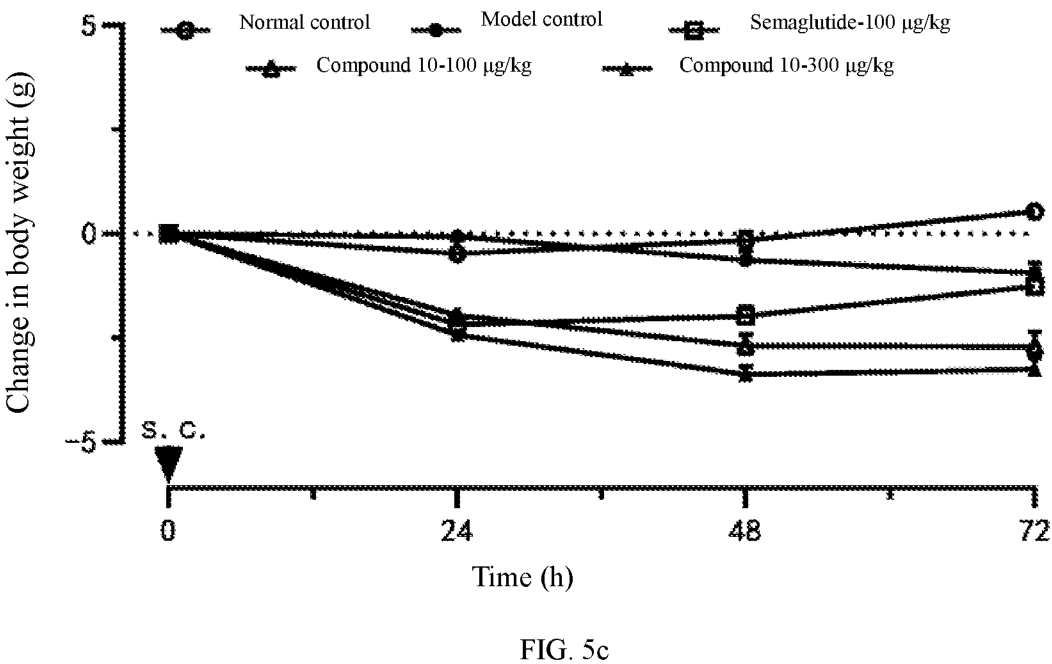
FIG. 5*c* shows the weight loss effect of the title compound of Example 11, the title compound of Comparative Example 2 and vehicle (model control group) on high fat diet-induced obese C57BL mice or normal mice (normal control group) according to the present invention.
Figure 6A:
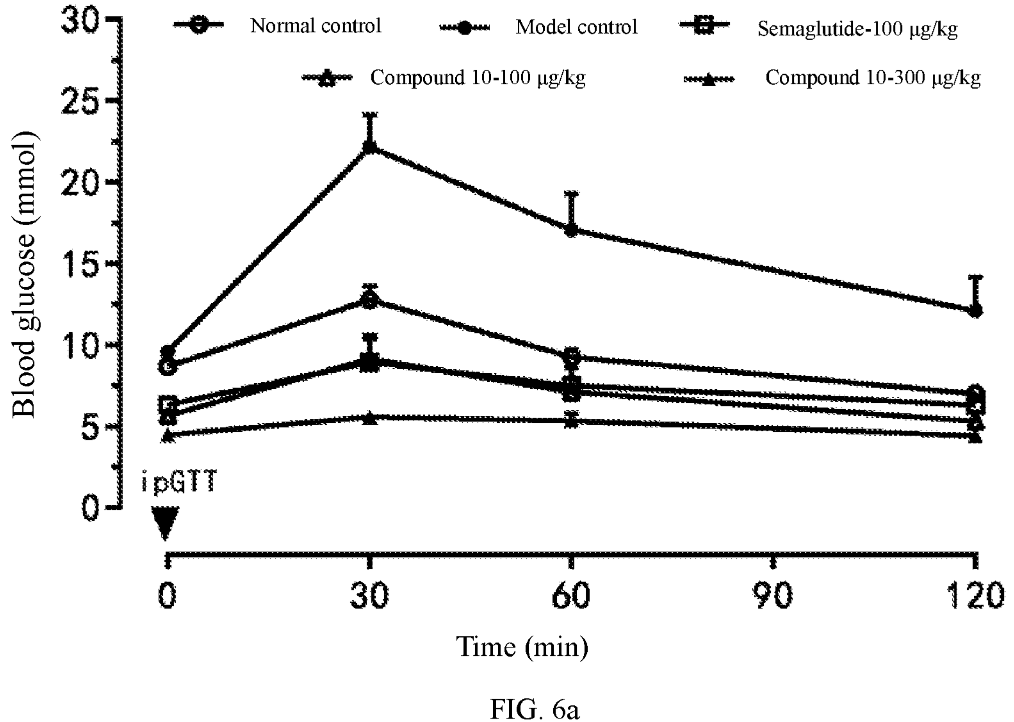
FIG. 6*a* shows the hypoglycemic effect of the title compound of Example 11, the title compound of Comparative Example 2 and vehicle (model control group) on high fat diet-induced obese C57BL mice or normal mice (normal control group) when ipGTT is performed 48 h after the first administration according to the present invention.
Figure 6B:
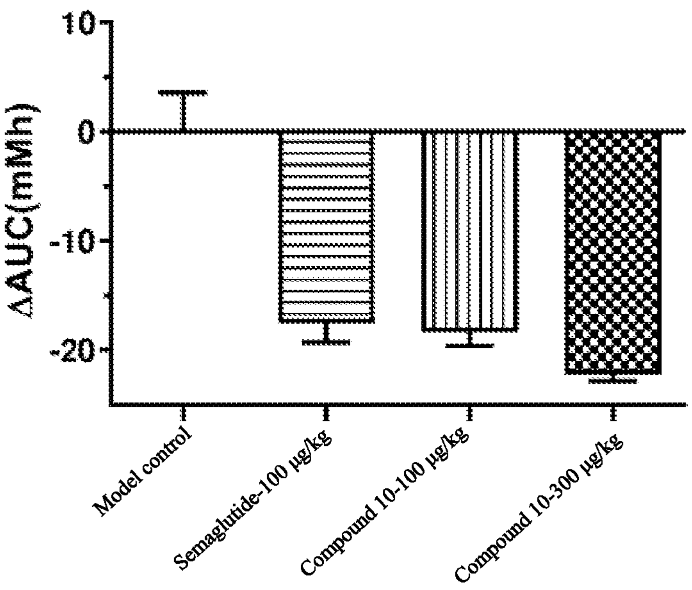
FIG. 6*b* shows, in correspondence with FIG. 6*a*, the ΔAUC of the hypoglycemic effect of the title compound of Example 11, the title compound of Comparative Example 2 and vehicle (model control group) on high fat diet-induced obese C57BL mice or normal mice (normal control group) when ipGTT is performed 48 h after the first administration according to the present invention.
Figure 7A:
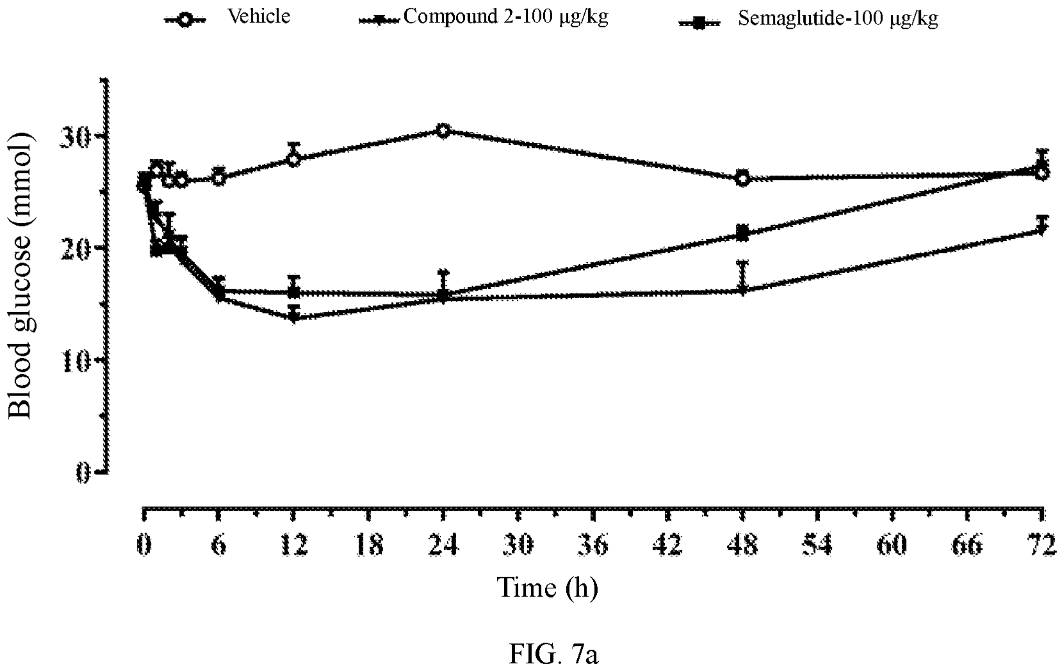
FIG. 7*a* shows the hypoglycemic effect of the title compound of Example 2, the title compound of Comparative Example 2 and vehicle on db/db mice according to the present invention.
Figure 7B:
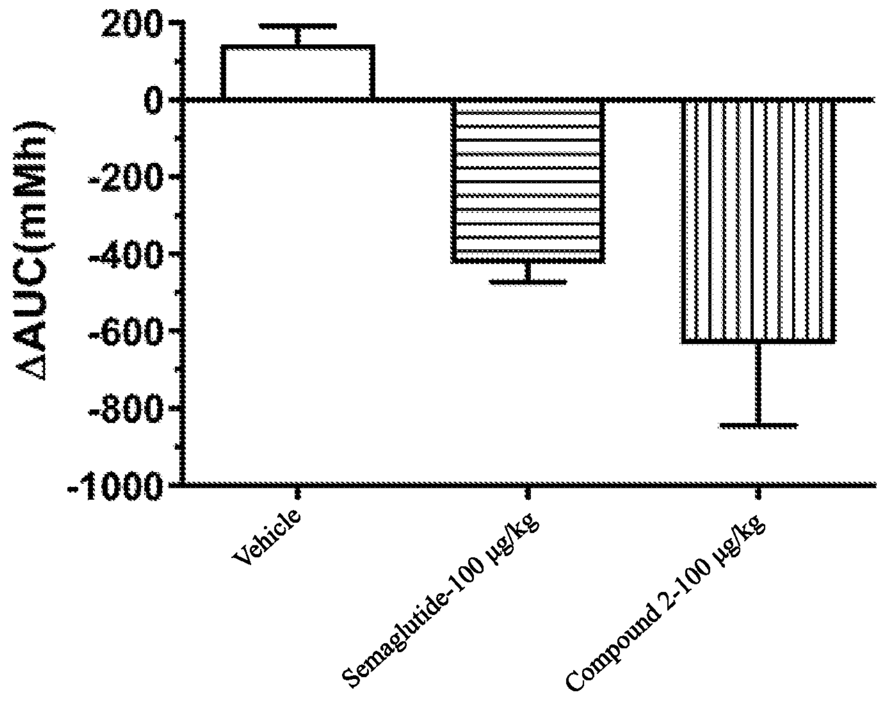
FIG. 7*b* shows, in correspondence with FIG. 7*a*, the ΔAUC of the hypoglycemic effect of the title compound of Example 2, the title compound of Comparative Example 2 and vehicle on db/db mice according to the present invention.
Figure 7C:
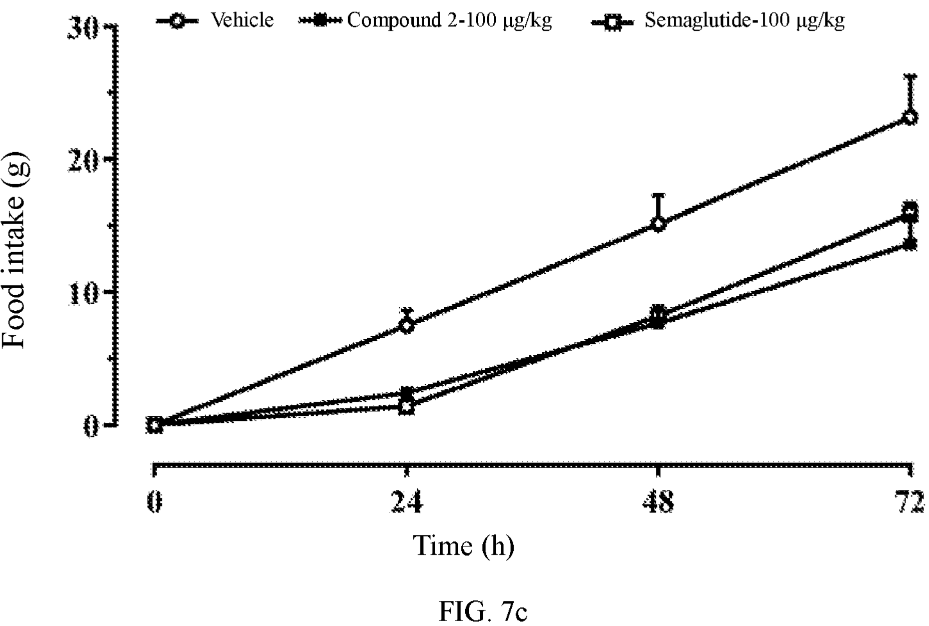
FIG. 7*c* shows the control effect of the title compound of Example 2, the title compound of Comparative Example 2 and vehicle on the food intake in db/db mice according to the present invention.
Figure 7D:
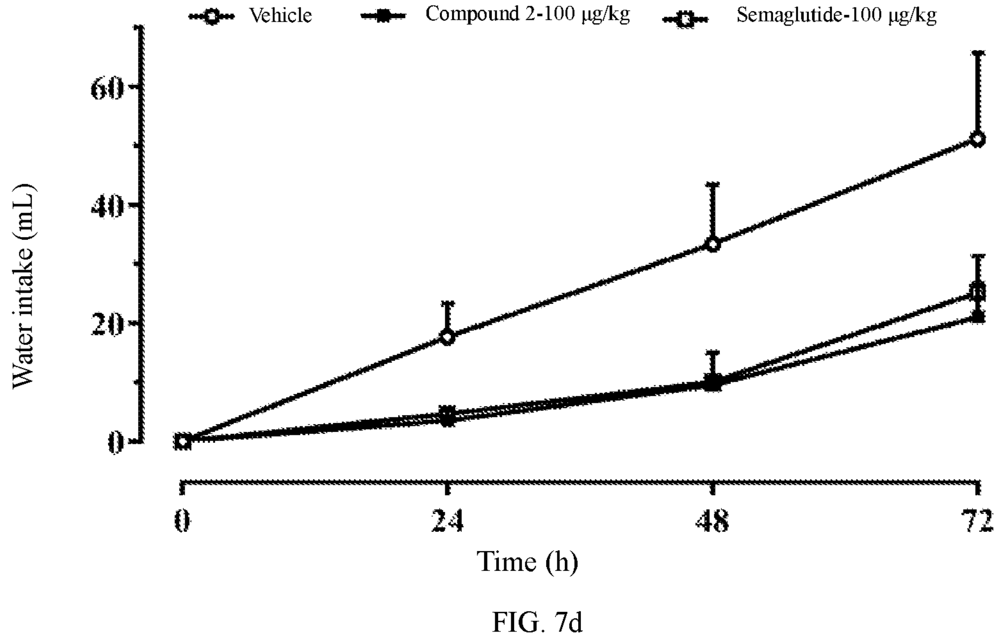
FIG. 7*d* shows the control effect of the title compound of Example 2, the title compound of Comparative Example 2 and vehicle on the water intake in db/db mice according to the present invention.

FIGS. 5*a*-6*b* show that the GLP-1 derivatives disclosed herein have a surprisingly improved drug effect, for example, the hypoglycemic effect of compound 10 of Example 11 on high fat diet-induced obese C57BL mice is not significantly different from the marketed control compound semaglutide at the same dose, and even the hypoglycemic effect of the GLP-1 derivatives disclosed herein is slightly superior to that of semaglutide, as can be seen in FIGS. 5*b* and 6*b* for the quantification. In particular, at 72 h after the administration, the mean blood glucose of compound 10 group at the same dose is lower than that of the semaglutide group at the same dose. In addition, the hypoglycemic effect of the GLP-1 derivatives disclosed herein is dose-dependent, which is significantly improved as the dose of GLP-1 disclosed herein increases.

FIGS. 6*a*-6*b* show that compound 10 of Example 11 has a significant inhibitory effect on blood glucose compared to vehicle, and has a slightly superior hypoglycemic effect to semaglutide at the same dose after the ipGTT test 48 h after the first administration of high fat diet-induced obese C57BL mice in the ipGTT test.

FIG. 5*c* shows that the GLP-1 derivatives disclosed herein, e.g., compound 10 of Example 11, have an excellent weight loss effect, which is superior to that of semaglutide.

Example 14. Pharmacodynamic Study on db/db Mice with Type 2 Diabetes

This study was intended to demonstrate the blood glucose regulating effect of the GLP-1 derivatives disclosed herein in the case of diabetes.

The hypoglycemic effect of the title compound of Example 11 and the control compound liraglutide was tested at different doses of 0.3 nmol/kg, 1 nmol/kg, 3 nmol/kg, 10 nmol/kg, 30 nmol/kg and 100 nmol/kg in db/db mice, and the $ED_{50}$ was calculated.

Male db/db (BKS/Lepr) mice aged 8-9 weeks were housed in appropriately sized feeding cages in a barrier environment and had free access to standard food and purified water, with environmental conditions controlled at 40%-60% RH and 22-24° C. After an adaptation period of 1-2 weeks, the mice were used in the experiment.

Before the start of the experiment on the day, the mice were evaluated for baseline blood glucose at 9:00 a.m. and weighed. Diabetic mice were each distributed to either the vehicle group or the treatment group based on random blood glucose and body weight, and subjected to the following treatments: subcutaneous injection of the vehicle, or subcutaneous injection of the compound of Example 11 or the control compound liraglutide at 0.3 nmol/kg, 1 nmol/kg, 3 nmol/kg, 10 nmol/kg, 30 nmol/kg and 100 nmol/kg, wherein the vehicle contained 14 mg/mL propylene glycol, 5.5 mg/mL phenol and 1.133 mg/mL disodium hydrogen phosphate, with a pH value of 7.4.

The administration was performed once by subcutaneous injection (s.c., 50 μL/10 g body weight) at back of the neck. The compound of Example 11 was administered at about 10:00 a.m. (time 0), and the blood glucose of the mice was evaluated 1 h, 2 h, 3 h, 6 h, 12 h, 24 h, 48 h and 72 h after the administration.

The tail of each mouse was cleaned with an alcohol cotton ball, and blood drops were collected from the tail using a disposable blood collection needle and measured with a glucometer (Roche) and accompanying testing strips.

The dose-response curve of Δ blood glucose versus time was plotted for each single dose of GLP-1 derivative. Δ refers to the actual blood glucose at a given time minus the baseline, where the baseline is the blood glucose at time 0. In order to illustrate the effect of the GLP-1 derivatives on blood glucose, the area under the curve of Δ blood glucose (ΔAUC) from 0 h to 72 h for each individual dose-response curve was calculated, and the effective dose 50% ($ED_{50}$, the dose of the GLP-1 derivatives that produces half of the response between baseline and maximal effect) was calculated for the ΔAUC. The $ED_{50}$ values obtained are shown in Table 2 below.

TABLE 2

$ED_{50}$ values of the effect on blood glucose in db/db mice

| Sample name | $ED_{50}$(nmol/kg) |
|---|---|
| Liraglutide | 9.68 |
| Compound 10 | 8.42 |

It can be seen from the test results that the in vivo hypoglycemic effect of the compound 10 is significantly superior to that of liraglutide.

Example 15. Pharmacodynamic Study on db/db Mice with Type 2 Diabetes

This study was intended to demonstrate the control effect of the GLP-1 derivatives disclosed herein on blood glucose, food intake and water intake.

The title compound of Example 2 and the control compound semaglutide were tested in a single dose study on db/db mice with type 2 diabetes.

Male db/db (BKS/Lepr) mice aged 8-9 weeks were housed in appropriately sized feeding cages in a barrier environment and had free access to standard food and purified water, with environmental conditions controlled at 40%-60% RH and 22-24° C. After an adaptation period of 1-2 weeks, the mice were used in the experiment.

Before the start of the experiment on the day, the mice were evaluated for baseline blood glucose at about 9:00 a.m. and weighed. Diabetic mice were each distributed to either the vehicle group or the treatment group based on random blood glucose and body weight, and subjected to the following treatments: subcutaneous injection of the vehicle, or subcutaneous injection of the compound of Example 2 or the control compound semaglutide at 100 μg/kg, wherein the vehicle contained 14 mg/mL propylene glycol, 5.5 mg/mL phenol and 1.133 mg/mL disodium hydrogen phosphate, with a pH value of 7.4.

The GLP-1 derivatives were dissolved in the vehicle to an administration concentration of 20 μg/mL, and the administration was performed once by subcutaneous injection (s.c., 50 μL/10 g body weight) at back of the neck. The compound of Example 2 was administered at about 10:00 a.m. (time 0), and the blood glucose of the mice was evaluated 1 h, 2 h, 3 h, 6 h, 12 h, 24 h, 48 h and 72 h after the administration. The tail of each mouse was cleaned with an alcohol cotton ball, and blood drops were collected from the tail using a disposable blood collection needle and measured with a glucometer (Roche) and accompanying testing strips. Meanwhile, the food intake and water intake of the mice were monitored every day.

The dose-response curve of blood glucose versus time, the dose-response curve of food intake versus time, and the dose-response curve of water intake versus time were plotted for each single dose of GLP-1 derivative. In order to illustrate the effect of the GLP-1 derivatives disclosed herein on blood glucose, the difference in area under the blood glucose-time curve (ΔAUC) from time 0 to the monitoring endpoint was calculated for each individual dose-response curve. The smaller the ΔAUC value, the better the hypoglycemic effect, and the better the drug effect.

FIGS. 7*a*-7*d* show that the GLP-1 derivatives disclosed herein have a surprisingly improved hypoglycemic effect and an improved inhibitory effect on food intake and water intake after the administration. This further demonstrates that the title compound of Example 2 has a superior hypoglycemic effect on db/db mice after the administration to semaglutide at the same dose. Furthermore, the title compound of Example 2 can effectively control the food intake and water intake, and its effect is superior to semaglutide, suggesting that the GLP-1 derivatives disclosed herein have better weight loss effect.

Example 16. Long-Term Pharmacodynamic Study on db/db Mice with Type 2 Diabetes

This study was intended to demonstrate the long-term hypoglycemic, weight loss, and diet control effects of the GLP-1 derivatives disclosed herein on db/db mice with type 2 diabetes.

The GLP-1 derivative of Example 11 and the control compound semaglutide were tested on diabetic db/db mice with type 2 diabetes. The GLP-1 derivatives at different doses of 100 μg/kg and 300 μg/kg and semaglutide at a dose of 100 μg/kg were administered to mice to determine the effects of the GLP-1 derivatives and the control compound semaglutide on lowering blood glucose, lowering body weight and reducing food intake and water intake.

Male db/db (BKS/Lepr) mice aged 8-9 weeks were housed in appropriately sized feeding cages in a barrier environment and had free access to standard food and purified water, with environmental conditions controlled at 40%-60% RH and 22-24° C. After an adaptation period of 1-2 weeks, the mice were used in the experiment.

Before the start of the experiment on the day, the mice were evaluated for baseline blood glucose at about 9:00 a.m. and weighed. Diabetic mice were each distributed to either the vehicle group or the treatment group based on random blood glucose and body weight, and subjected to the following treatments: subcutaneous injection of the vehicle, or subcutaneous injection of the GLP-1 derivatives at 100 μg/kg and 300 μg/kg or the control compound semaglutide at 100 μg/kg. The vehicle contained 14 mg/mL propylene glycol, 5.5 mg/mL phenol and 1.133 mg/ml disodium hydrogen phosphate, with a pH value of 7.4.

The GLP-1 derivatives were administered by subcutaneous injection (s.c., 50 μL/10 g body weight) at back of the neck at about 10:00 a.m. (time 0) on days 0, 3, 7, 10, 13, 16, 19, 22, 25 and 28, and the blood glucose of the mice was evaluated before each administration and 72 h after the last administration. The weight, food intake and water intake of the mice were measured daily on days 0-17, and the weight, food intake and water intake of the mice were monitored every 3 days after day 17.

Figure 8A:
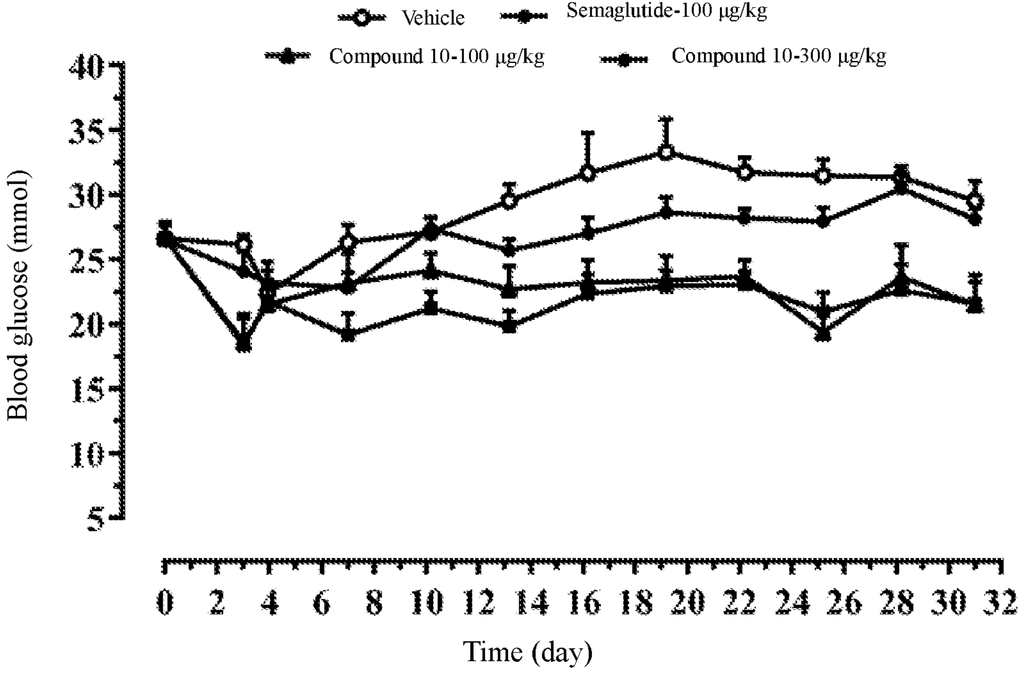
FIG. 8*a* shows the long-term hypoglycemic effect of the title compound of Example 11, the title compound of Comparative Example 2 and vehicle on db/db mice according to the present invention.
Figure 8B:
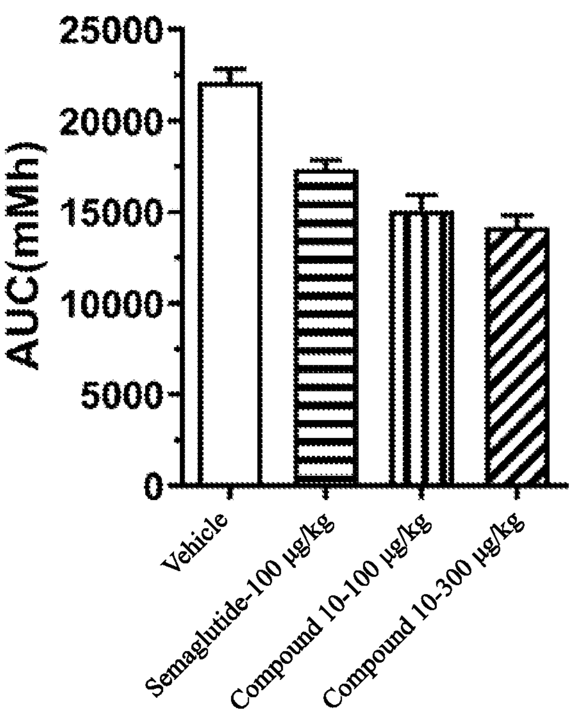
FIG. 8*b* shows, in correspondence with FIG. 8*a*, the AUC of the long-term hypoglycemic effect of the title compound of Example 11, the title compound of Comparative Example 2 and vehicle on db/db mice according to the present invention.
Figure 8C:
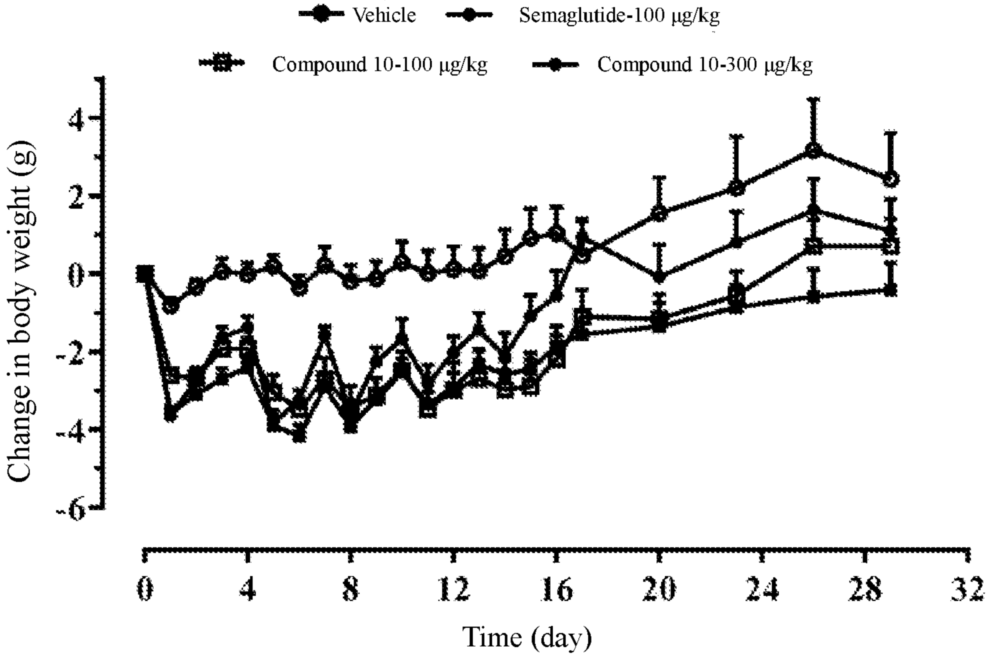
FIG. 8*c* shows the long-term weight loss effect of the title compound of Example 11, the title compound of Comparative Example 2 and vehicle on db/db mice according to the present invention.
Figures 8D, 8E:
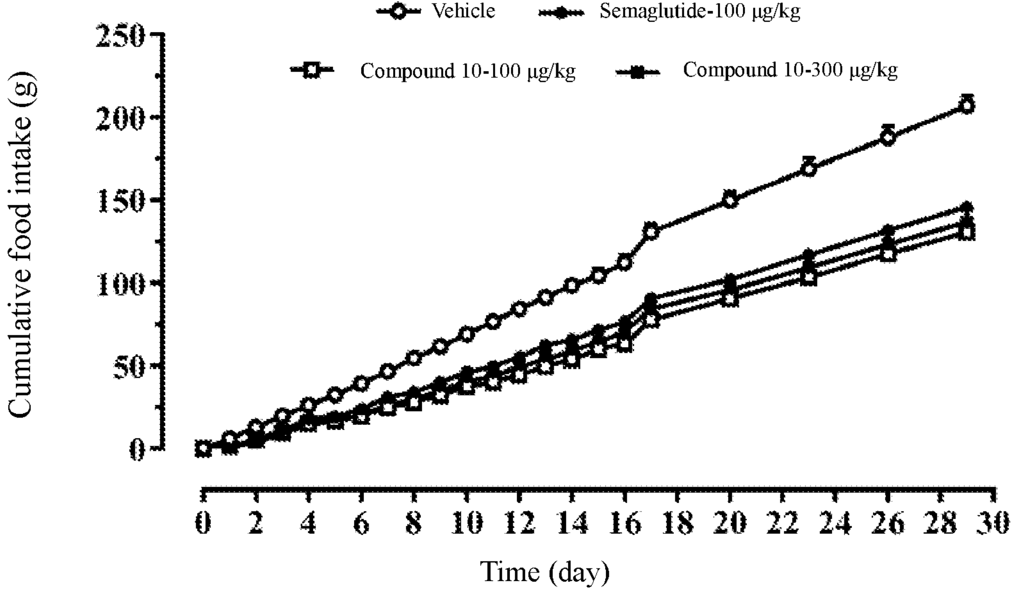
FIG. 8*d* shows the control effect of the title compound of Example 11, the title compound of Comparative Example 2 and vehicle on the long-term food intake in db/db mice according to the present invention.
FIG. 8*e* shows the control effect of the title compound of Example 11, the title compound of Comparative Example 2 and vehicle on the long-term water intake in db/db mice according to the present invention.

FIGS. 8a-8f show that the GLP-1 derivatives disclosed herein still have a surprisingly improved hypoglycemic effect, an improved weight loss effect, and an inhibitory effect on food intake and water intake after the long-term administration. As shown in FIGS. 8a and 8b, compound 10 of Example 11 has a superior hypoglycemic effect on db/db mice after the long-term administration compared to semaglutide at the same dose. FIGS. 8c-8d show that the GLP-1 derivatives disclosed herein, e.g., the title compound of Example 11, have a better weight loss effect and an inhibitory effect on food intake and water intake than semaglutide at the same dose.

Example 17. Long-Term Pharmacodynamic Study on Kkay Mice with Type 2 Diabetes

This study was intended to demonstrate the hypoglycemic effect of the GLP-1 derivatives disclosed herein on Kkay mice with type 2 diabetes.

Compound 10 of Example 11, compound 2 of Example 2, and the control compound dulaglutide were tested on Kkay mice with type 2 diabetes. Compound 10 and compound 2 at different doses of 100 μg/kg and 300 μg/kg, and dulaglutide at a dose of 600 μg/kg were administered to mice to determine the hypoglycemic and HbA1c-reducing effects of the GLP-1 derivatives disclosed herein and the control compound dulaglutide.

Male Kkay mice aged 12-14 weeks were housed in appropriately sized feeding cages in a barrier environment and had free access to standard food and purified water, with environmental conditions controlled at 40%-60% RH and 22-24° C. After an adaptation period of 1-2 weeks, the mice were used in the experiment.

Before the start of the experiment on the day, the mice were evaluated for baseline blood glucose at about 9:00 a.m. and weighed. Diabetic mice were each distributed to either the vehicle group or the treatment group based on random blood glucose and body weight, and subjected to the following treatments: subcutaneous injection of the vehicle, or subcutaneous injection of the GLP-1 derivatives disclosed herein at 100 μg/kg and 300 μg/kg or the control compound dulaglutide at 600 μg/kg. The vehicle contained 14 mg/mL propylene glycol, 5.5 mg/mL phenol and 1.133 mg/mL disodium hydrogen phosphate, with a pH value of 7.4.

The GLP-1 derivatives disclosed herein, dulaglutide or vehicle was administered by subcutaneous injection (s.c., 50 μL/10 g body weight) at about 10:00 a.m. (time 0) at back of the neck once every 2 days for 16 consecutive times, the blood glucose of the mice was evaluated 3 h, 6 h, 1 day and 2 days after the first administration, and HbA1c was detected in an EDTA anticoagulation tube 48 h after the last administration.

Figure 9A:
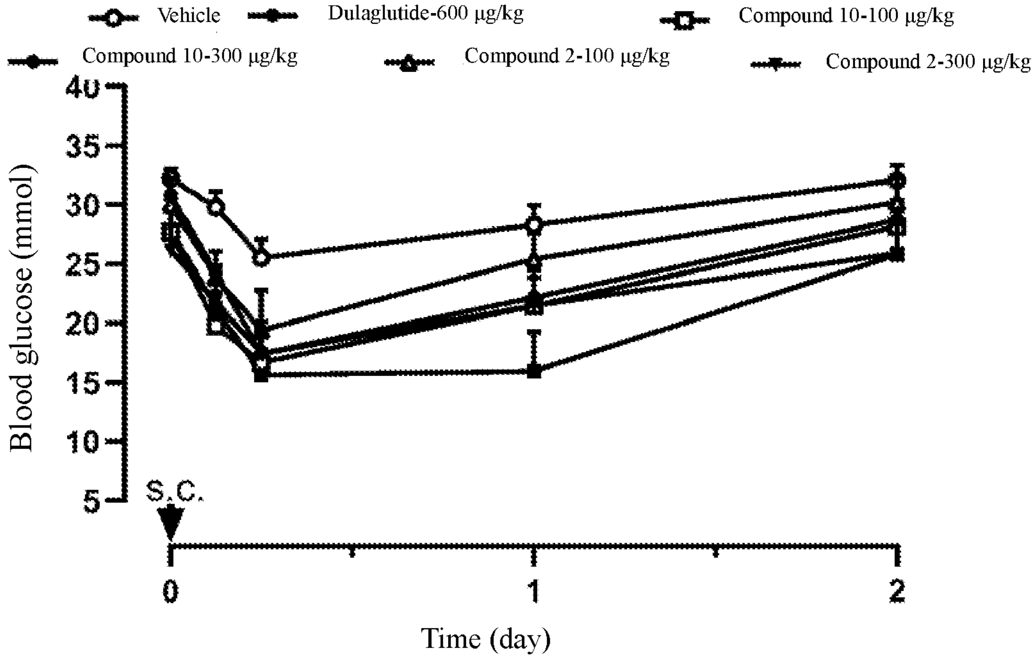
FIG. 9*a* shows the hypoglycemic effect of the title compounds of Example 11 and Example 2 according to the present invention, dulaglutide and vehicle on Kkay mice.
Figure 9B:
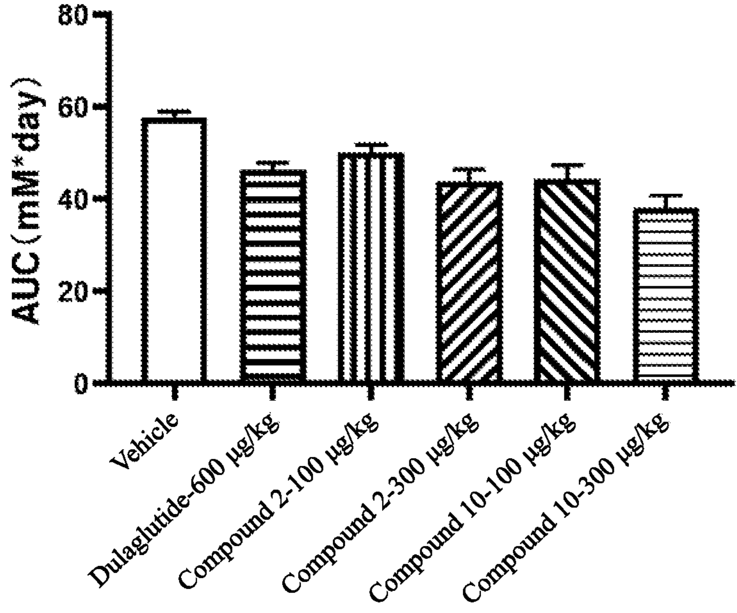
FIG. 9*b* shows, in correspondence with FIG. 9*a*, the AUC of the hypoglycemic effect of the title compounds of Example 11 and Example 2 according to the present invention, dulaglutide and vehicle on Kkay mice.
Figure 9C:
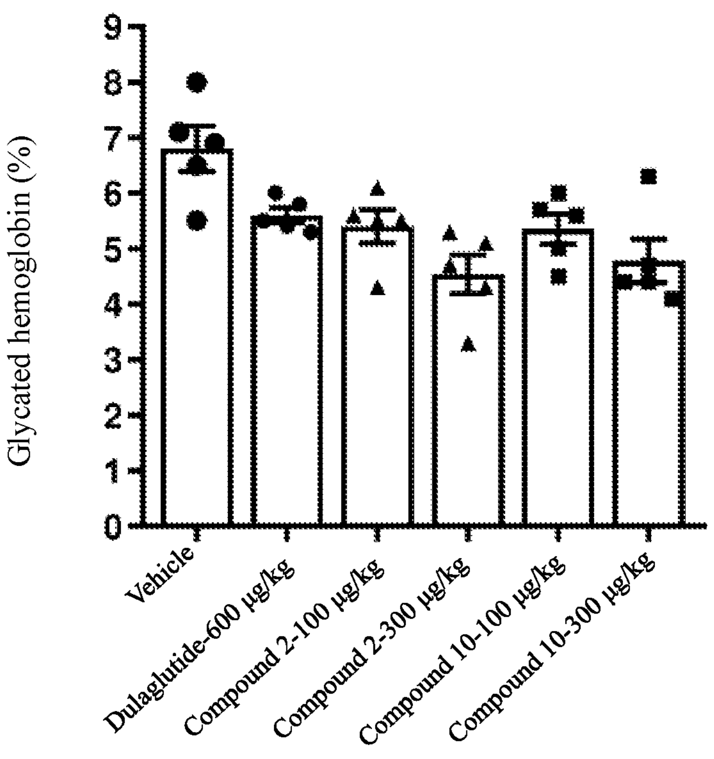
FIG. 9*c* shows the HbA1c-reducing effect of the title compounds of Example 11 and Example 2 according to the present invention, dulaglutide and vehicle on Kkay mice.

FIGS. 9a-9b show that the GLP-1 derivatives disclosed herein have a surprisingly improved hypoglycemic effect after the administration, and the title compounds of Examples 11 and 2 have a significantly superior hypoglycemic effect on Kkay mice to dulaglutide. FIG. 9c shows that the GLP-1 derivatives disclosed herein have a significantly superior HbA1c-reducing effect on Kkay mice with type 2 diabetes to dulaglutide.

Example 18. Pharmacokinetics

This example was intended to illustrate the in vivo pharmacokinetic profile of the compounds disclosed herein.

Pharmacokinetics in SD Rats

A total of 32 SD rats were divided into compound 10 low-dose group, compound 10 medium-dose group, compound 10 high-dose group (subcutaneous administrations at 15 μg/kg, 90 μg/kg and 540 μg/kg, respectively), and compound 10 intravenous injection group (intravenous injection at 90 μg/kg), with 8 rats (half male and half female) for each group. The mice in the compound 10 low-dose, medium-dose and high-dose groups were subjected to blood sampling before the administration (0 min), 1 h, 3 h, 5 h, 8 h, 12 h, 16 h, 24 h, 36 h, 48 h, 72 h, 96 h and 120 h after the administration to determine the plasma concentration, and the mice in the compound 10 intravenous injection group were subjected to blood sampling before the administration (0 min), 1 min, 10 min, 1 h, 3 h, 5 h, 8 h, 12 h, 24 h, 48 h, 72 h, 96 h and 120 h after the administration to determine the plasma concentration. The pharmacological parameters $C_{max}$, $T_{max}$, $T_{1/2}$, $AUC_{0-t}$ and MRT were calculated using a non-compartmental model of WinNonLin v6.4 software. The results are shown in Table 3.

TABLE 3

| Pharmacokinetic parameters of compound 10 after subcutaneous injection in SD rats | | | | | |
|---|---|---|---|---|---|
| Dose (μg/kg) | $C_{max}$(ng/ml) | $T_{max}$(hr) | $T_{1/2}$(hr) | $AUC_{0-t}$ (hr*ng/ml) | MRT(hr) |
| 15 | 48.6 | 12 | 12.5 | 1489.9 | 21.2 |
| 90 | 296 | 14 | 13.0 | 9952.3 | 25.2 |
| 540 | 1490 | 16 | 13.3 | 61497.1 | 30.4 |
| 90(i.v.) | 2540 | — | 13.0 | 23800 | 12.9 |

$C_{max}$=measured maximum plasma concentration, $T_{max}$=time corresponding to measured maximum plasma concentration, $T_{1/2}$=terminal elimination half-life, $AUC_{0-t}$=area under the time plasma concentration curve from time 0 to time t, MRT=mean residence time Pharmacokinetics in Cynomolgus Monkeys A total of 24 cynomolgus monkeys were divided into compound 10 low-dose group, compound 10 medium-dose group, compound 10 high-dose group (subcutaneous administrations at 10 μg/kg, 60 μg/kg and 360 μg/kg, respectively), and compound 10 intravenous injection group (intravenous injection at 60 μg/kg), with 6 cynomolgus monkeys (half male and half female) for each group. The mice in the compound 10 low-dose, medium-dose and high-dose groups were subjected to blood sampling before the administration (0 min), 1 h, 3 h, 6 h, 8 h, 10 h, 12 h, 16 h, 24 h, 48 h, 72 h, 120 h, 168 h and 240 h after the administration to determine the plasma concentration, and the mice in the compound 10 intravenous injection group were subjected to blood sampling before the administration (0 min), 1 min, 10 min, 1 h, 3 h, 6 h, 8 h, 10 h, 12 h, 24 h, 48 h, 72 h, 120 h, 168 h and 240 h after the administration to determine the plasma concentration. The pharmacological parameters $C_{max}$, $T_{max}$, $T_{1/2}$, $AUC_{0-t}$ and MRT were calculated using a non-compartmental model of WinNonLin v6.4 software. The results are shown in Table 4.

TABLE 4

| Pharmacokinetic parameters of compound 10 after subcutaneous injection in cynomolgus monkeys | | | | | |
|---|---|---|---|---|---|
| Dose (μg/kg) | $C_{max}$(ng/ml) | $T_{max}$(hr) | $T_{1/2}$(hr) | $AUC_{0-t}$ (hr*ng/ml) | MRT(hr) |
| 10 | 80.7 | 9 | 58.4 | 7387 | 73.6 |
| 60 | 455 | 11 | 59.2 | 42256 | 76.0 |
| 360 | 2895 | 14 | 62.9 | 278528 | 74.5 |
| 60(i.v.) | 1720 | — | 65.6 | 74200 | 63.5 |

It can be seen from the above experimental results that the GLP-1 derivative compound 10 of the present invention exhibits comparatively long half-life, comparatively large $AUC_{0-t}$, and comparatively long MRT in both rats and cynomolgus monkeys. In addition, the GLP-1 derivatives disclosed herein are dose-dependent, the drug effect of which is improved as the dose increases.

Example 19

This experiment was intended to determine the chemical stability of GLP-1 derivative formulations disclosed herein.

GLP-1 Derivative Formulations

Compound 10 was dissolved in 5.68 mg/mL disodium hydrogen phosphate solution to a final concentration of 8 mg/mL, and an auxiliary solution containing propylene glycol and an auxiliary solution containing phenol were added sequentially, according to the amount of each component specified in the table below, to adjust the pH to the values in the table below, to obtain the GLP-1 compound solution at a final concentration of 2 mg/mL.

The chemical stability of the formulations in this example can be shown by the changes in the amount of high molecular weight protein (HMWP) after 27 days of storage at 37° C. relative to day 0, and can also be shown by the changes in the amount of related substances measured after 28 days of storage at 37° C.

Determination of High Molecular Weight Protein (HMWP)

The content of high molecular weight protein (HMWP) was determined on a Waters TSKgel G2000SWXL (7.8×300 mm, 5 μm) column by high performance liquid chromatography (HPLC) (column temperature: 30° C.; sample cell temperature: 5° C.; mobile phase: 300 mL of isopropanol, 400 mL of glacial acetic acid and 300 mL of purified water; flow rate: 0.5 mL/min). The detection wavelength was 276 nm, and the sample volume was 25 μL. Table 5 shows the increase in the amount of HMWP on day 27 relative to day 0 of storage at 37° C.

Determination of the Amount of Related Substances

The content of related impurities in the GLP-1 derivatives was determined on a Waters Kromasil 100-3.5-C8 (4.6×250 mm) column by high performance liquid chromatography (HPLC) (column temperature: 35° C.; sample cell temperature: 5° C.; flow rate of elution phase: 1.0 mL/min). Elution was performed with a mobile phase consisting of: phase A: 90 mM potassium dihydrogen phosphate and 10% acetonitrile (v/v), pH 2.4; and phase B: 75% (v/v) acetonitrile.

Gradient: a linear change from 75%/25% A/B to 55%/45% A/B from 0 min to 5 min, a linear change to 50%/50% A/B from 5 min to 12 min, a linear change to 40%/60% A/B from 12 min to 42 min, a linear change to 10%/90% A/B from 42 min to 60 min, a linear change to 75%/25% A/B from 60 min to 61 min, and an isocratic gradient of 85%/15% A/B from 61 min to 70 min.

The detection wavelength was 214 nm, the flow rate was 1.0 mL/min, and the sample volume was 15 μL. Table 5 shows the increase in the amount of related substances on day 0 relative to day 28 of storage at 37° C.

TABLE 5

| 2 mg/mL compound 10<br>14 mg/mL propylene glycol<br>5.65 mg/mL phenol<br>1.42 mg/mL anhydrous sodium dihydrogen phosphate | 37° C. Increase in the amount of HMWP on day 27 relative to day 0 (%) | 37° C. Increase in the amount of the related substances on day 28 relative to day 0 (%) |
|---|---|---|
| pH 6.5 | 0.822 | 4.35 |
| pH 7.0 | 0.956 | 3.74 |
| pH 7.7 | 1.808 | 2.92 |
| pH 8.0 | 2.572 | 3.63 |
| pH 8.4 | 4.048 | 4.62 |

It can be seen from the above table that the formulations all have good chemical stability at pH 6.5-8.4, and have the best chemical stability at pH 7.0-8.0.

Example 20

This experiment was intended to determine the chemical stability of GLP-1 derivative formulations disclosed herein.

The GLP-1 derivative formulations in Tables 6 and 7 were formulated, according to the amount of each component specified in Tables 6 and 7 below, by procedures similar to those described in Example 19. Besides, changes in HMWP and related substances were determined by procedures similar to those described in Example 19. Tables 6 and 7 below show the changes in the amount of HMWP and related substances in the GLP-1 derivative formulations of different formulas.

TABLE 6

| 2 mg/mL compound 10 14 mg/mL propylene glycol pH 7.3 | 25° C. Increase in the amount of HMWP on day 14 relative to day 0 (%) | 25° C. Increase in the amount of HMWP on day 21 relative to day 0 (%) | 37° C. Increase in the amount of HMWP on day 14 relative to day 0 (%) | 37° C. Increase in the amount of HMWP on day 21 relative to day 0 (%) |
|---|---|---|---|---|
| 5.5 mg/mL phenol + 1.42 mg/mL anhydrous disodium hydrogen phosphate | 0.16 | 0.21 | 0.41 | 0.62 |
| 5.65 mg/mL phenol + 1.42 mg/mL anhydrous disodium hydrogen phosphate | 0.13 | 0.17 | 0.36 | 0.58 |
| 6.2 mg/mL phenol + 1.42 mg/mL anhydrous disodium hydrogen phosphate | 0.12 | 0.18 | 0.41 | 0.60 |
| 5.5 mg/mL phenol + 1.133 mg/mL anhydrous disodium hydrogen phosphate | 0.16 | 0.2 | 0.67 | 1.00 |

TABLE 7

| 2 mg/mL compound 10 14 mg/mL propylene glycol pH 7.3 | 25° C. Increase in the amount of the related substances on day 14 relative to day 0 (%) | 25° C. Increase in the amount of the related substances on day 21 relative to day 0 (%) | 37° C. Increase in the amount of the related substances on day 14 relative to day 0 (%) | 37° C. Increase in the amount of the related substances on day 35 relative to day 0 (%) |
|---|---|---|---|---|
| 5.5 mg/mL phenol + 1.42 mg/mL anhydrous disodium hydrogen phosphate | 0.64 | 1.04 | 2.06 | 4.00 |
| 5.65 mg/mL phenol + 1.42 mg/mL anhydrous disodium hydrogen phosphate | 0.50 | 1.15 | 2.15 | 4.08 |
| 6.2 mg/mL phenol + 1.42 mg/mL anhydrous disodium hydrogen phosphate | 0.94 | 1.16 | 1.73 | 4.07 |
| 5.5 mg/mL phenol + 1.133 mg/mL anhydrous disodium hydrogen phosphate | 0.71 | 1.15 | 1.90 | 4.27 |

It can be seen from the above table that the amount of HMWP and the amount of related substances in the GLP-1 derivative formulations increase very slowly with time, suggesting that the GLP-1 derivative formulations have excellent chemical stability.

Comparative Example 5

A14E, B16H, B25H, B29K(N(ε)-eicosanedioyl-γGlu-2×OEG), desB30 Human Insulin (Control Compound 5)

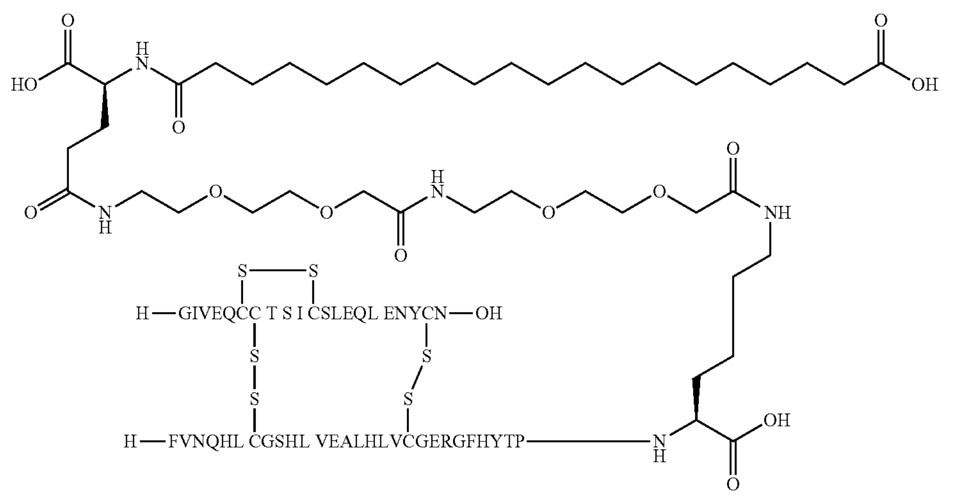

1. Preparation of A14E, B16H, B25H, B29K(N(ε)-eicosanedioyl-γGlu-2×OEG), desB30 Human Insulin A14E, B16H, B25H, desB30 human insulin was prepared using a conventional method for preparing insulin analogues (for details, see Glendorf T, Sørensen A R, Nishimura E, Pettersson I, & Kjeldsen T: Importance of the Solvent-Exposed Residues of the Insulin B Chain α-Helix for Receptor Binding; *Biochemistry,* 2008, 47:4743-4751). A14E, B16H, B25H, desB30 human insulin (5 g, 0.888 mmol) was dissolved in 100 mM aqueous $Na_2HPO_4$ solution (150 mL) and acetonitrile (100 mL) was added. The pH was adjusted to 10-12.5 with 1 N NaOH. Tert-butyl eicosanedioyl-γGlu-(2×OEG-OSu)-OtBu (0.948 g, 0.976 mmol) was dissolved in acetonitrile (50 mL), and the solution was slowly added to the insulin solution. The pH value was maintained at 10-12.5. After 120 min, the reaction mixture was added to water (150 mL), and the pH value was adjusted to 5.0 with 1 N aqueous HCl. The precipitate was separated out by centrifugation and lyophilized. The lyophilized crude product was added to a mixed solution of trifluoroacetic acid (60 mL) and dichloromethane (60 mL), and the mixture was stirred at room temperature for 30 min. The mixture was then concentrated to about 30 mL and poured into ice-cold n-heptane (300 mL), and the precipitated product was isolated by filtration and washed twice with n-heptane. The resulting precipitate was dried in vacuum and purified by ion exchange chromatography (Resource Q, 0.25%-1.25% ammonium acetate gradient in 42.5% ethanol, pH 7.5) and reverse phase chromatography (acetonitrile, water, TFA). The purified fractions were combined, adjusted to pH value 5.2 with 1 N HCl, and separated to obtain the precipitate, which was lyophilized to obtain the control compound 5.

LC-MS (ESI): m/z=1063.6852$[M+6H]^{6+}$

2. Preparation of Intermediate Tert-Butyl Eicosanedioyl-γGlu-(2×OEG-OSu)-OtBu: by Procedures Similar to Those Described in Section 3 of Example 1

2.1 Tert-Butyl Eicosanedioyl-OSu

Eicosanedioic acid mono-tert-butyl ester (20 g, 50.17 mmol) and NHS (5.77 g, 50.17 mmol) were mixed in dichloromethane under nitrogen atmosphere, and triethylamine (13.95 mL) was added. The resulting turbid mixture was stirred at room temperature, added with DCC (11.39 g, 55.19 mmol) and further stirred overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-OSu (24.12 g, yield 97%).

LC-MS (Sciex100 API): m/z=496.36$(M+1)^+$

2.2 Tert-Butyl Eicosanedioyl-γGlu-OtBu

Tert-butyl eicosanedioyl-OSu (24.12 g, 48.66 mmol) was dissolved in dichloromethane (250 mL), and the solution was stirred and added with H-Glu-OtBu (10.88 g, 53.53 mmol), triethylamine (12.49 mL) and water sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight to obtain tert-butyl eicosanedioyl-γGlu-OtBu (27.27 g, yield 96%).

LC-MS (Sciex100 API): m/z=584.44$(M+1)^+$

2.3 Tert-Butyl Eicosanedioyl-γGlu-(OSu)-OtBu

Tert-butyl eicosanedioyl-γGlu-OtBu (27.27 g, 46.71 mmol) was dissolved in dichloromethane (300 mL) under nitrogen atmosphere, and triethylamine (11.99 mL) was added. The mixture was stirred for 10 min, and NHS (5.38 g, 50.17 mmol) was added, followed by the addition of DCC (10.60 g, 51.38 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure. Tert-butyl methyl ether was added, and the mixture was stirred for 30 min and filtered in vacuum. The filter cake was dried in vacuum overnight to obtain tert-butyl eicosanedioyl-γGlu-(OSu)-OtBu (25.76 g, yield 81%).

LC-MS (Sciex100 API): m/z=681.46$(M+1)^+$

2.4 Tert-Butyl Eicosanedioyl-γGlu-(2×OEG-OH)-OtBu

Tert-butyl eicosanedioyl-γGlu-(OSu)-OtBu (25.76 g, 37.83 mmol) was dissolved in dichloromethane (250 mL), and the solution was stirred and added with 2×AEEA (11.66 g, 37.83 mmol), triethylamine (9.71 mL) and water (25 mL) sequentially. The mixture was heated to obtain a clarified solution, which was then stirred at room temperature for 4 h. Then, the reaction solution was added with 10% aqueous citric acid solution (200 mL) and subjected to liquid separation. The lower organic phase was washed with saturated brine, and after liquid separation, the lower organic phase was dried over anhydrous sodium sulfate and filtered, and the filtrate was concentrated to almost dryness under reduced pressure and dried in vacuum overnight. Tert-butyl eicosanedioyl-γGlu-(2×OEG-OH)-OtBu (30.75 g, yield 93%) was obtained.

LC-MS (Sciex100 API): m/z=874.59$(M+1)^+$

2.5 Tert-Butyl Eicosanedioyl-γGlu-(2×OEG-OSu)-OtBu

Tert-butyl eicosanedioyl-γGlu-(2×OEG-OH)-OtBu (30.75 g, 35.18 mmol) was dissolved in dichloromethane (300 mL) under nitrogen atmosphere, and triethylamine (9.03 mL) was added. The mixture was stirred for 10 min, and NHS (4.05 g, 35.18 mmol) was added, followed by the addition of DCC (7.98 g, 38.70 mmol). The reaction mixture was stirred at room temperature overnight. The reaction mixture was filtered, and the resulting filtrate was concentrated to almost dryness. The residue was mixed with cold water and ethyl acetate, and the mixture was stirred for 20 min and subjected to liquid separation. The upper organic phase was washed with saturated brine, and after liquid separation, the upper organic phase was dried over anhydrous sodium sulfate and filtered, and the filtrate was concentrated to almost dryness under reduced pressure and dried in vacuum overnight to obtain tert-butyl eicosanedioyl-γGlu-(2×OEG-OSu)-OtBu (31.09 g, yield 91%).

LC-MS (Sciex100 API): m/z=971.61(M+1)$^+$

Example 21

A14E, B16H, B25H, B29K(N(ε)-eicosanedioyl-γGlu-6×OEG), desB30 Human Insulin (Compound 11)

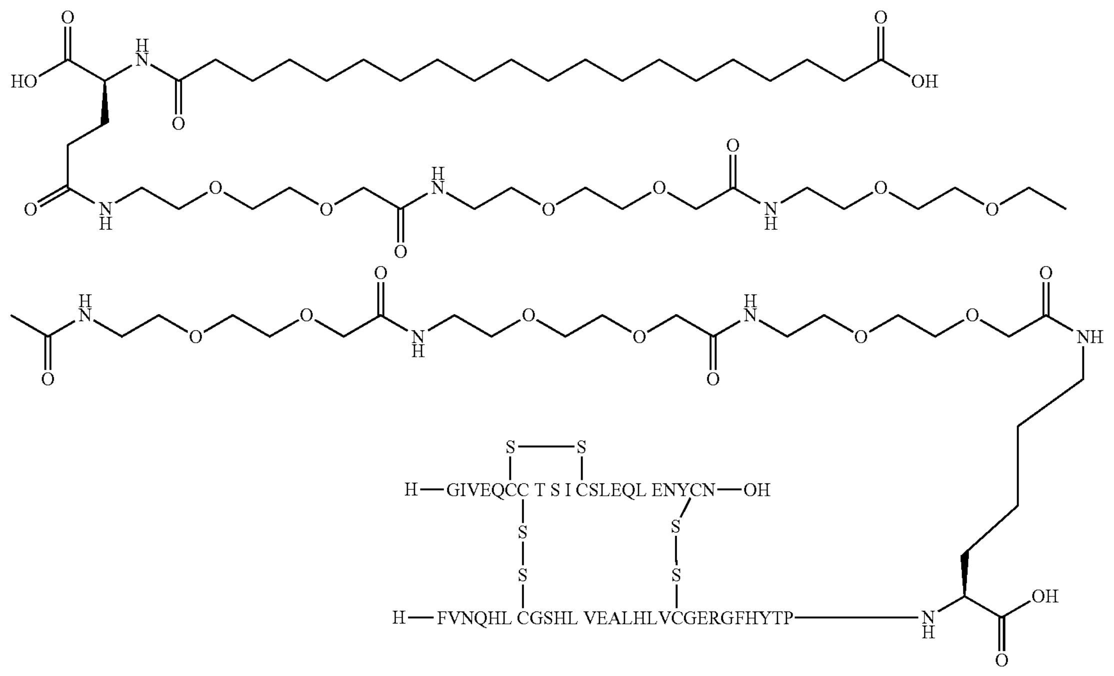

Compound A14E, B16H, B25H, B29K(N(ε)-eicosanedioyl-γGlu-6×OEG), desB30 human insulin was prepared by procedures similar to those described in section 1 of Comparative Example 5.

LC-MS (ESI): m/z=1160.3997[M+6H]$^{6+}$

The intermediate tert-butyl eicosanedioyl-γGlu-(6×OEG-OSu)-OtBu was prepared by procedures similar to those described in section 2 of Comparative Example 5.

LC-MS (Sciex100 API): m/z=1551.90(M+1)$^+$

Example 22

A14E, B16H, B25H, B29K(N(ε)-docosanedioyl-γGlu-6×OEG), desB30 Human Insulin (Compound 12)

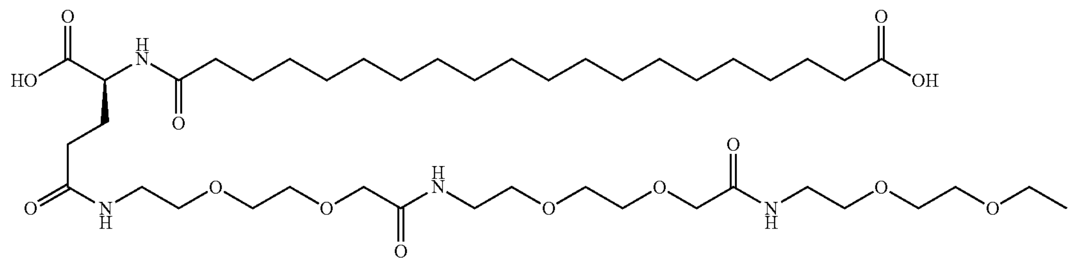

-continued

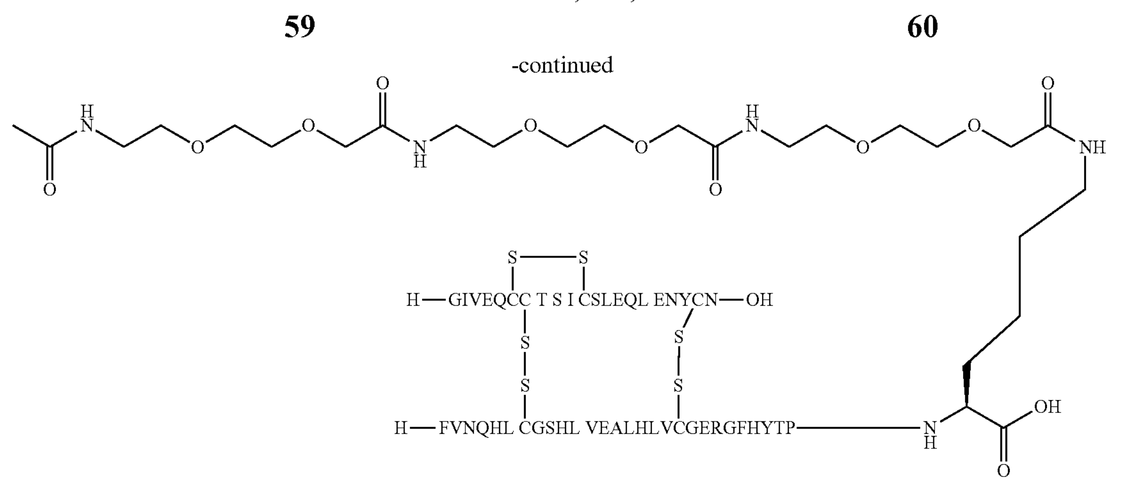

Compound A14E, B16H, B25H, B29K(N(ε)-docosanedioyl-γGlu-6×OEG), desB30 human insulin was prepared by procedures similar to those described in section 1 of Comparative Example 5.

LC-MS (ESI): m/z=1165.0674[M+6H]$^{6+}$

The intermediate tert-butyl docosanedioyl-γGlu-(6×OEG-OSu)-OtBu was prepared by procedures similar to those described in section 2 of Comparative Example 5.

LC-MS (Sciex100 API): m/z=1579.94(M+1)$^+$

Example 23

A14E, B16H, B25H, B29K(N(ε)-eicosanedioyl-γGlu-12×OEG), desB30 Human Insulin (Compound 13)

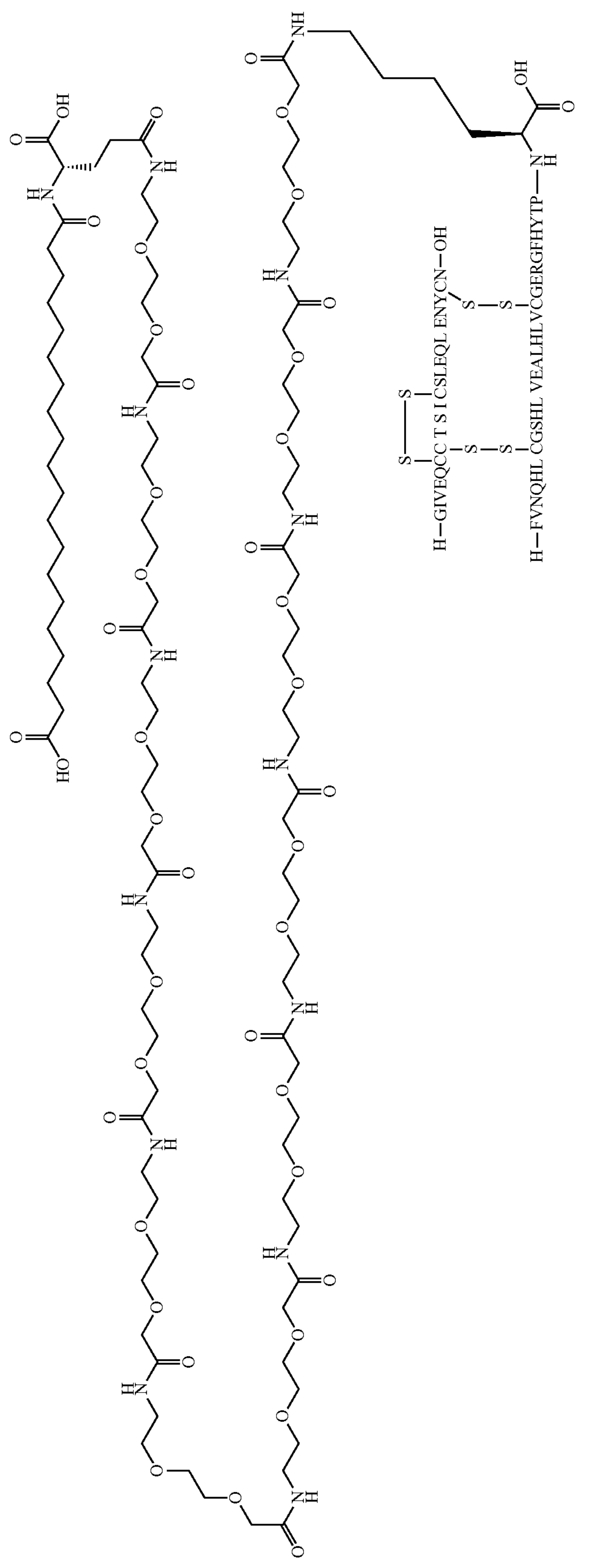

Compound A14E, B16H, B25H, B29K(N(ε)-eicosanedioyl-γGlu-12×OEG), desB30 human insulin was prepared by procedures similar to those described in section 1 of Comparative Example 5.

LC-MS (ESI): m/z=1305.4716$[M+6H]^{6+}$

The intermediate tert-butyl eicosanedioyl-γGlu-(12×OEG-OSu)-OtBu was prepared by procedures similar to those described in section 2 of Comparative Example 5.

LC-MS (Sciex100 API): m/z=2423.35$(M+1)^{+}$

Example 24

A14E, B16H, B25H, B29K(N(ε)-docosanedioyl-γGlu-12×OEG), desB30 Human Insulin (Compound 14)

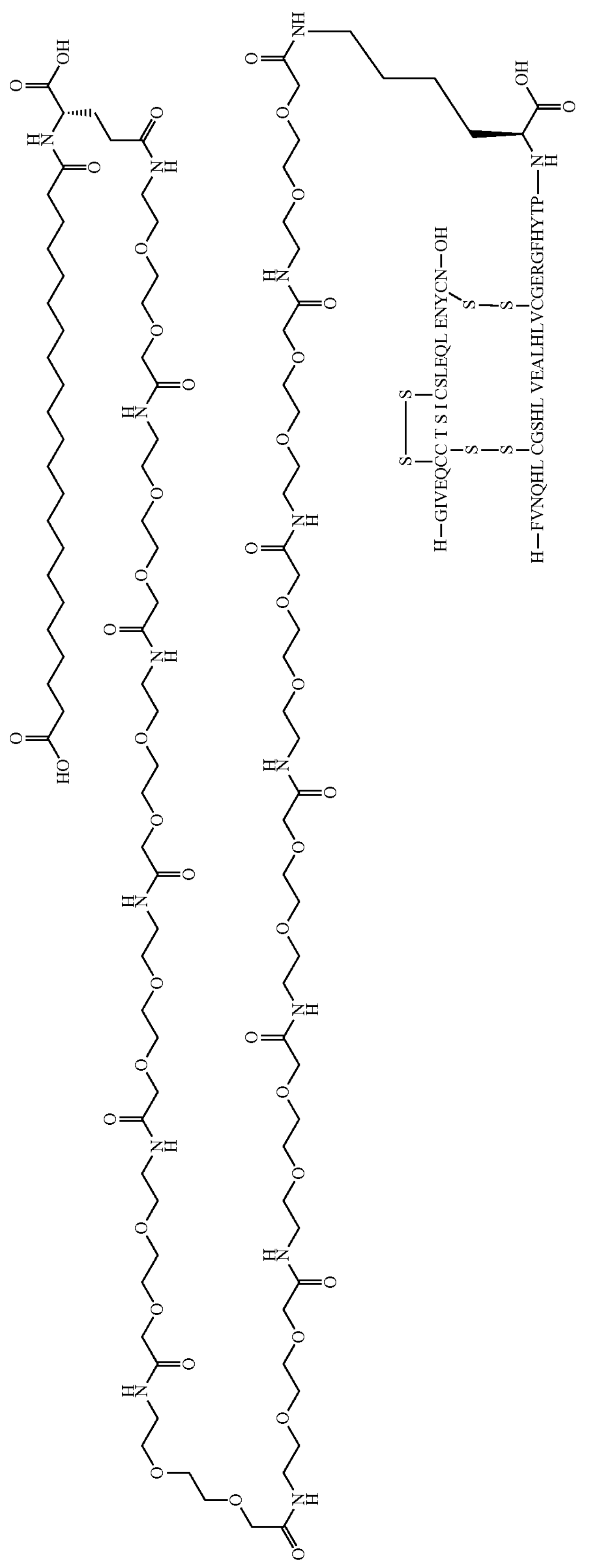
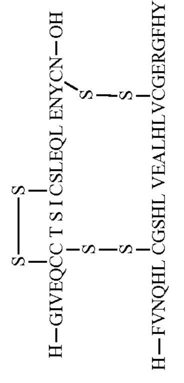

Compound A14E, B16H, B25H, B29K(N(ε)-docosanedioyl-γGlu-12×OEG), desB30 human insulin was prepared by procedures similar to those described in section 1 of Comparative Example 5.

LC-MS (ESI): m/z=1310.1425[M+6H]$^{6+}$

The intermediate tert-butyl docosanedioyl-γGlu-(12×OEG-OSu)-OtBu was prepared by procedures similar to those described in section 2 of Comparative Example 5.

LC-MS (Sciex100 API): m/z=2451.38(M+1)$^+$

Example 25. GLP-1 Receptor Binding

This example was intended to test the binding affinity of the GLP-1 derivatives disclosed herein for receptors in vitro, and how the presence of albumin potentially affected the binding. Receptor binding is a measure of the affinity of the GLP-1 derivatives for the human GLP-1 receptor.

The binding affinity of the GLP-1 derivatives disclosed herein and control compounds for the human GLP-1 receptor was determined as follows: determining their ability to substitute $^{125}$I-GLP-1 in the receptor. For determining the binding of the GLP-1 derivatives to albumin (HSA), low-concentration albumin (0.005% (w/v)) and high-concentration albumin (2% (w/v)) were used. The change in the binding affinity $IC_{50}$ shows that the GLP-1 derivatives bind to albumin, thereby predicting a potentially prolonged pharmacokinetic profile of the GLP-1 derivatives in animal models.

For a receptor binding test in the presence of low-concentration HSA (0.005% (w/v)), 50 μL of assay buffer was added to each well of the assay plate. For a receptor binding test in the presence of high-concentration HSA (2% (w/v)), 50 μL of 8% (w/v) albumin stock solution was added to each well of the assay plate. The test compounds were formulated with 10 mM $Na_2HPO_4$ at pH value 7.3, and the reference control GLP-1(7-37) was prepared as a 1 mM stock solution with ultrapure water. In the presence of 0.005% HSA, all test compounds and the reference control were diluted to 2 μM with assay buffer, and then all samples were diluted in 4-fold serial gradient dilutions for a total of 10 concentration gradients. In the presence of 2% HSA, the reference control GLP-1(7-37) was diluted to 2 μM, liraglutide was diluted to 20 μM, compound 10 and semaglutide were diluted to 800 μM, and then all samples were diluted in 4-fold serial gradients for a total of 10 concentration gradients. 25 μL of test compounds or reference control at different concentrations were added to the appropriate wells of the assay plate, respectively. Cell membrane protein aliquots were thawed and diluted to their working concentration (40 μg/mL), and 50 μL of the cell membrane-containing solution was added to each well of the assay plate. The incubation was started by adding 25 μL of 600 pM [$^{125}$I]-GLP-1 to each well of the assay plate. The assay plate was incubated at room temperature for 1 h. After the incubation, the reaction solution was collected on a GF/C filter plate using a cell collector, washed 6 times with a washing buffer, and dried in a drying oven at 50° C. for 1 h. 50 μL of scintillation solution was added and blocked, and the values were read using Microbeta2. $IC_{50}$ values were calculated by the nonlinear regression analysis in the GraphPad Prism software and reported in nM. This was performed at least three times for each test compound. The values reported are the mean of all measurements for each test compound.

TABLE 8

Binding affinity for GLP-1 receptor

| Sample name | 0.005% HSA $IC_{50}$(nM)(SD) | 2% HSA $IC_{50}$(nM)(SD) | Ratio |
|---|---|---|---|
| Compound 10 | 3.67 (1.95) | 5552.33 (378.83) | 1513 |
| Liraglutide | 0.52 (0.34) | 29.44 (13.01) | 57 |
| Semaglutide | 0.75 (0.29) | 609.57 (51.33) | 813 |
| GLP-1(7-37) | 2.82 (1.07) | 1.50 (0.24) | 0.53 |

"Ratio" refers to [($IC_{50}$/nM) high-concentration HSA]/[($IC_{50}$/nM) low-concentration HSA].

In general, binding to the GLP-1 receptor should be as good as possible at a low albumin concentration, which corresponds to a low $IC_{50}$ value. The $IC_{50}$ value at a high albumin concentration is a measure of the effect of albumin on the binding of the GLP-1 derivatives to the GLP-1 receptor. As is known, the GLP-1 derivatives also bind to albumin, which is often a desired effect that will prolong their plasma lifetime. Therefore, the $IC_{50}$ value is generally higher at a high albumin concentration than the $IC_{50}$ value at a low albumin concentration, which corresponds to a reduced binding to the GLP-1 receptor due to the albumin binding competing with the GLP-1 receptor binding.

Therefore, a high ratio ($IC_{50}$ value (high-concentration albumin)/$IC_{50}$ value (low-concentration albumin)) may be used as an indication that the derivative of interest binds well to albumin (and thus can be determined to have a long half-life) and also binds well to the GLP-1 receptor (high $IC_{50}$ value (high-concentration albumin), low $IC_{50}$ value (low-concentration albumin)).

It can be seen from the above table that the ratio of the GLP-1 derivatives disclosed herein are higher than that of the control compounds semaglutide, liraglutide and GLP-1 (7-37), suggesting that the compounds disclosed herein have a longer half-life and bind well to the GLP-1 receptor.

Example 26. Long-Term Pharmacodynamic Study on db/db Mice with Type 2 Diabetes A long-term pharmacodynamic study was performed on db/db mice with type 2 diabetes by experimental procedures similar to those described in Example 16, except that the control compound used was dulaglutide administered at a dose of 300 μg/kg. The GLP-1 derivatives were administered by subcutaneous injection (s.c., 50 μL/10 g body weight) at back of the neck at about 10:00 a.m. (time 0) on days 0, 3, 6, 9, 12, 15, 18, 21, 24, 27 and 30. The blood glucose of the mice was evaluated 3 h, 6 h, 9 h, 12 h, 24 h, 48 h and 72 h after the first administration, and the change in area under the blood glucose-time curve (ΔAUC) was calculated. The mice were fasted for 6 h with the fasting blood glucose monitored before the administration and 48 h after the third, fifth and eleventh administrations. An intraperitoneal glucose tolerance test (ipGTT) was performed 48 h after the first administration, and the steps were as follows: blood was collected from the tail tip at the indicated time points to determine fasting blood glucose (0 min), followed by intraperitoneal administration of glucose solutions (200 mg/mL, 10 mL/kg), and then the blood glucose was determined 30 min, 60 min and 120 min after glycemic load. The tail of each mouse was cleaned with an alcohol cotton ball, and blood drops were collected from the tail using a disposable blood collection needle and measured with a glucometer (Roche) and accompanying testing strips. The blood glucose-time curve was plotted, and area under the curve (AUC) was calculated.

Figure 10A:
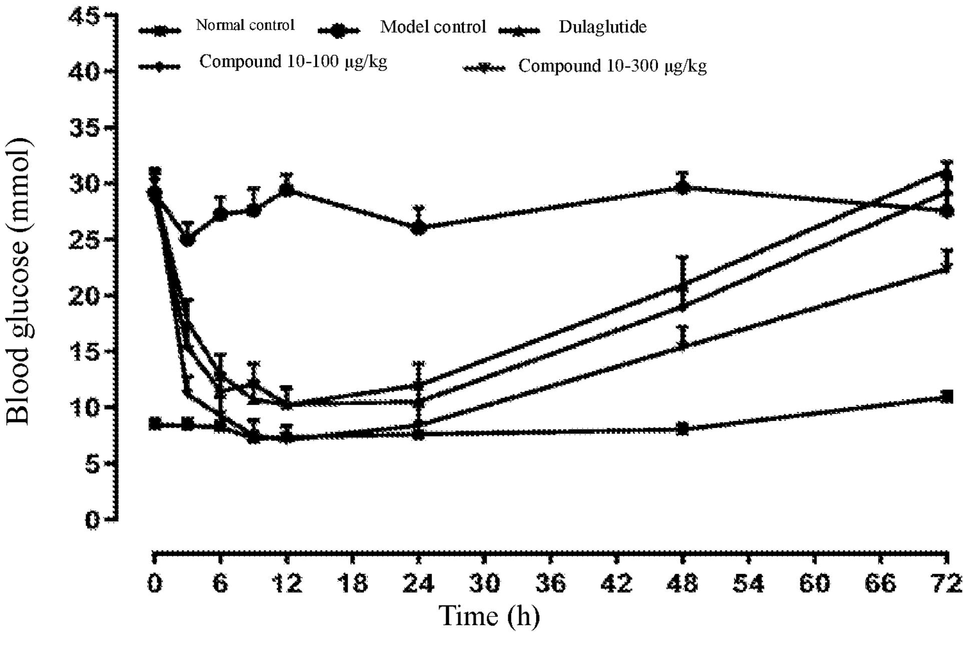
FIG. 10*a* shows the long-term hypoglycemic effect of the title compound of Example 11 according to the present invention, dulaglutide and vehicle (model control group) on db/db mice or normal mice (normal control group).
Figure 10B:
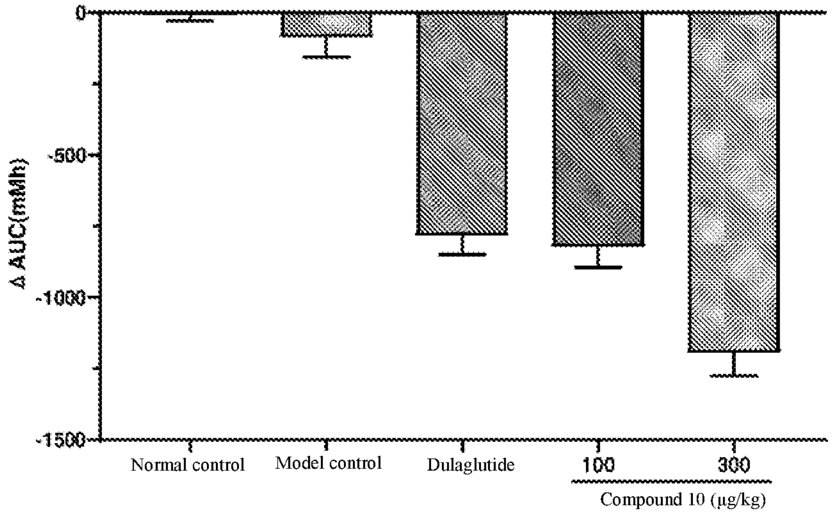
FIG. 10*b*, in correspondence with FIG. 10*a*, shows the ΔAUC of the long-term hypoglycemic effect of the title compound of Example 11 according to the present invention, dulaglutide and vehicle (model control group) on db/db mice or normal mice (normal control group).
Figure 10C:
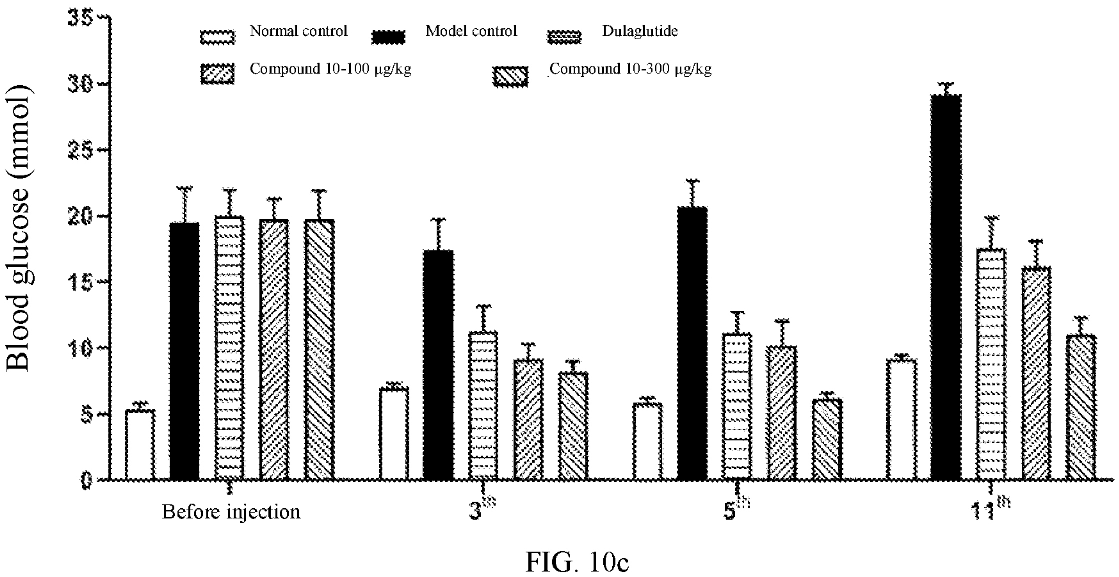
FIG. 10*c* shows the random blood glucose values of db/db mice or normal mice (normal control group) before the injection and after the third, fifth and eleventh injections of the title compound of Example 11 according to the present invention, dulaglutide and vehicle (model control group).
Figure 10D:
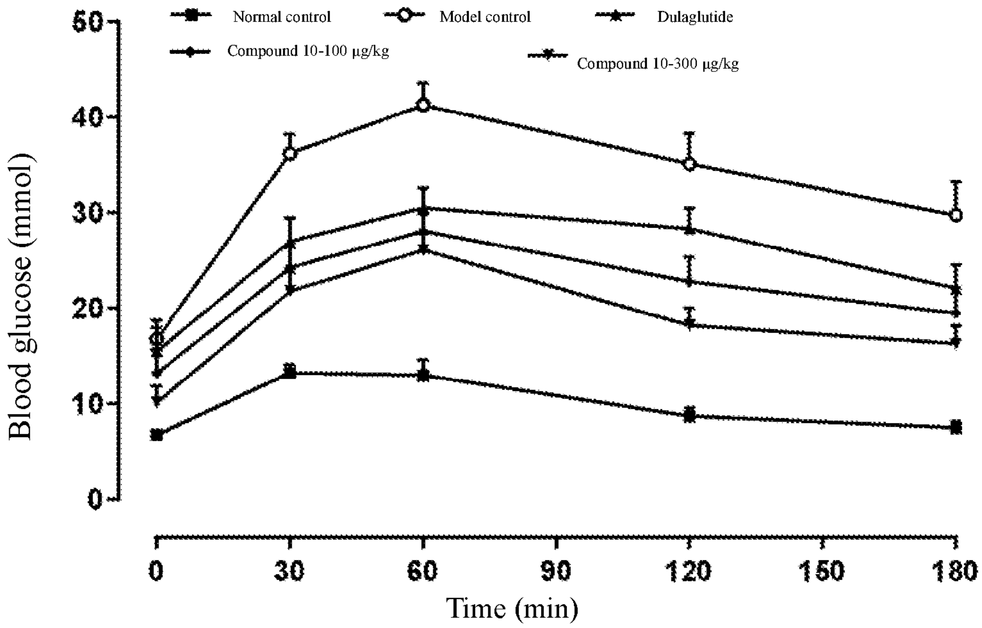
FIG. 10*d* shows the hypoglycemic effect of the title compound of Example 11 according to the present invention, dulaglutide and vehicle (model control group) on db/db mice or normal mice (normal control group) when ipGTT is performed 48 h after the first administration.
Figure 10E:
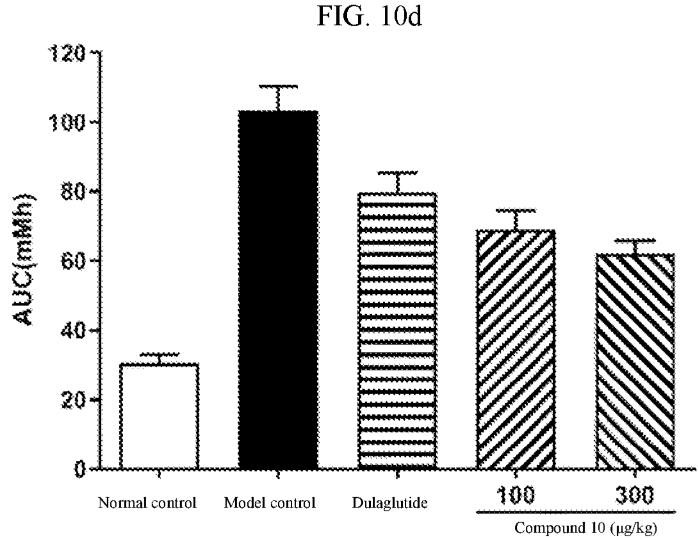
FIG. 10*e*, in correspondence with FIG. 10*d*, shows the AUC of the hypoglycemic effect of the title compound of Example 11 according to the present invention, dulaglutide and vehicle (model control group) on db/db mice or normal mice (normal control group) when ipGTT is performed 48 h after the first administration.
Figure 11A:
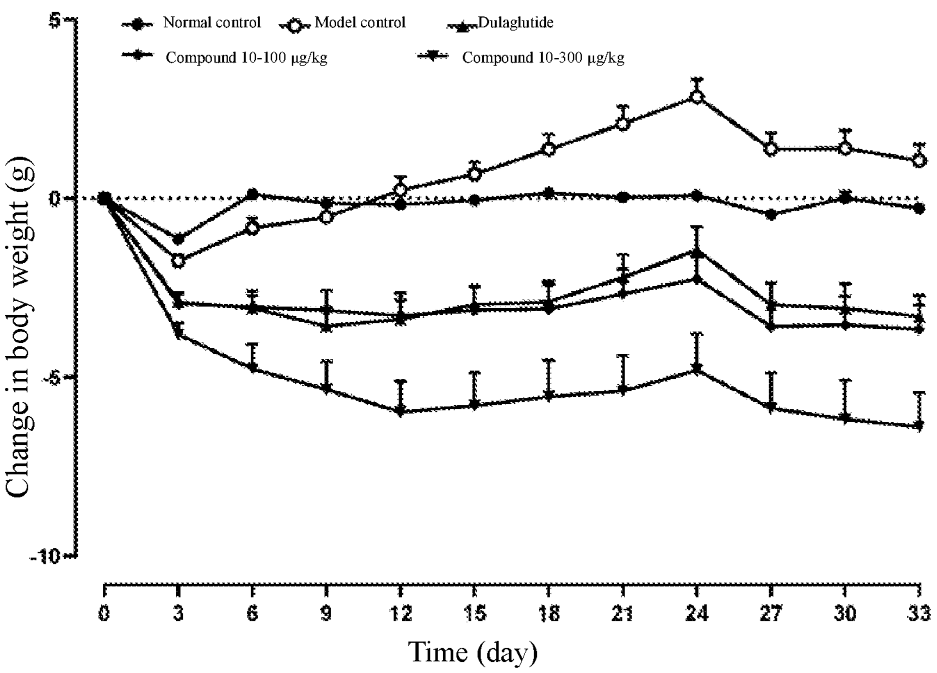
FIG. 11*a* shows the long-term weight loss effect of the title compound of Example 11 according to the present invention, dulaglutide and vehicle (model control group) on high fat diet-induced obese C57BL mice or normal mice (normal control group).
Figure 11B:
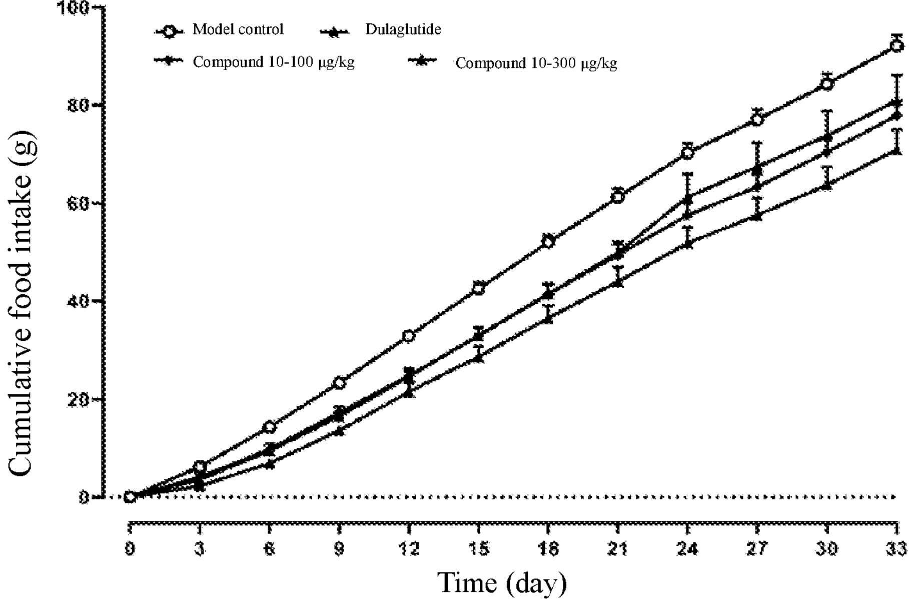
FIG. 11*b* shows the control effect of the title compound of Example 11 according to the present invention, dulaglutide and vehicle (model control group) on the long-term food intake in high fat diet-induced obese C57BL mice.
Figure 11C:
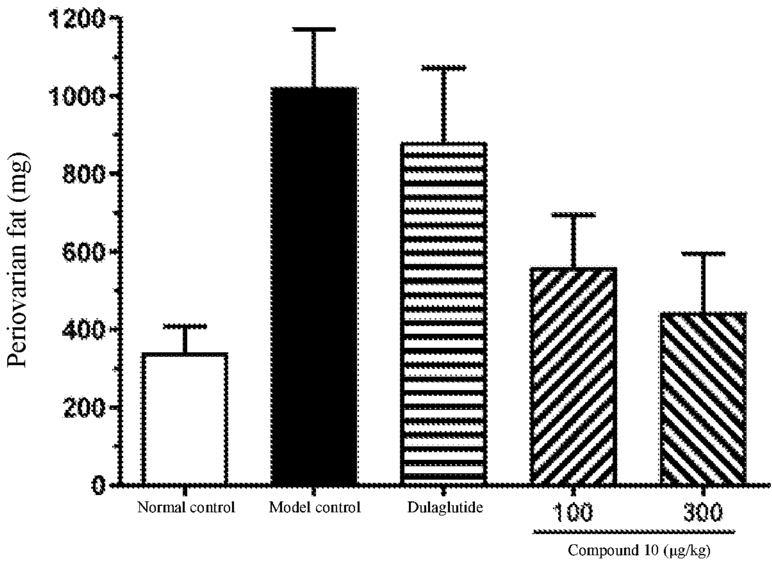
FIG. 11*c* shows the periovarian fat-reducing effect of the title compound of Example 11 according to the present invention, dulaglutide and vehicle (model control group) on high fat diet-induced obese C57BL female mice.
Figure 11D:
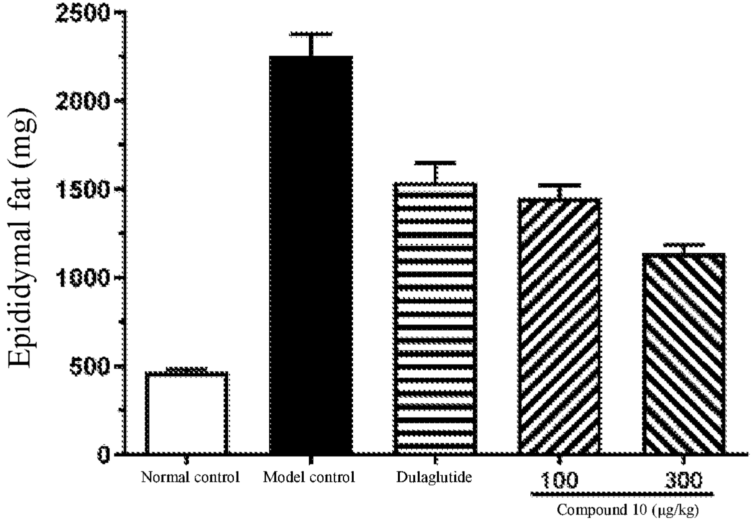
FIG. 11*d* shows the epididymal fat-reducing effect of the title compound of Example 11 according to the present invention, dulaglutide and vehicle (model control group) on high fat diet-induced obese C57BL male mice.

FIGS. 10a-10e show that the GLP-1 derivatives disclosed herein still have a surprisingly improved hypoglycemic effect after the long-term administration. As shown in FIGS. 10a and 10b, compound 10 of Example 11 has a superior hypoglycemic effect on db/db mice after the administration compared to dulaglutide. As shown in FIG. 10c, compound 10 has a superior hypoglycemic effect on db/db mice after the long-term administration compared to dulaglutide. As shown in FIGS. 10d-10e, the GLP-1 derivatives disclosed herein have a more significant inhibition effect on blood glucose compared to dulaglutide, and have a superior hypoglycemic effect to dulaglutide.

Example 27. Pharmacodynamic Study on High Fat Diet-Induced Obese C57BL Mice

A pharmacodynamic study was performed on high fat diet-induced obese C57BL mice by experimental procedures similar to those described in Example 13, except that the control compound used was dulaglutide administered at a dose of 300 μg/kg.

The administration was performed once every 3 days for a total of 11 times by subcutaneous administration (s.c., 5 μL/g body weight) at back of the neck. The GLP-1 derivatives were administered about 10:30 a.m. (time 0), and the blood glucose of the mice was evaluated at 3 h, 6 h, 9 h, 12 h, 24 h, 48 h and 72 h after the administration. Meanwhile, the body weight and food intake of the mice were monitored every 3 days. Subcutaneous fat, perirenal fat and perigenital fat were weighed at the end of the experiment.

FIGS. 11a-11d show that the GLP-1 derivatives disclosed herein have surprisingly improved weight loss, diet control, and fat-decreasing effects.

Example 28

B29K(N(ε)-docosanedioyl-γGlu-12×OEG), desB30 Human Insulin (Compound 15)

Compound B29K(N(ε)-docosanedioyl-γGlu-12×OEG), desB30 human insulin was prepared by procedures similar to those described in section 2 of Example 6.

LC-MS (ESI): m/z=1585.98$[M+5H]^{5+}$

The intermediate tert-butyl docosanedioyl-γGlu-(12×OEG-OSu)-OtBu was prepared by procedures similar to those described in section 3 of Example 6.

LC-MS (Sciex100 API): m/z=2451.38$(M+1)^+$

Example 29

A14E, B16H, B25H, B29K(N(ε)-docosanedioyl-γGlu-18×OEG), desB30 Human Insulin (Compound 16)

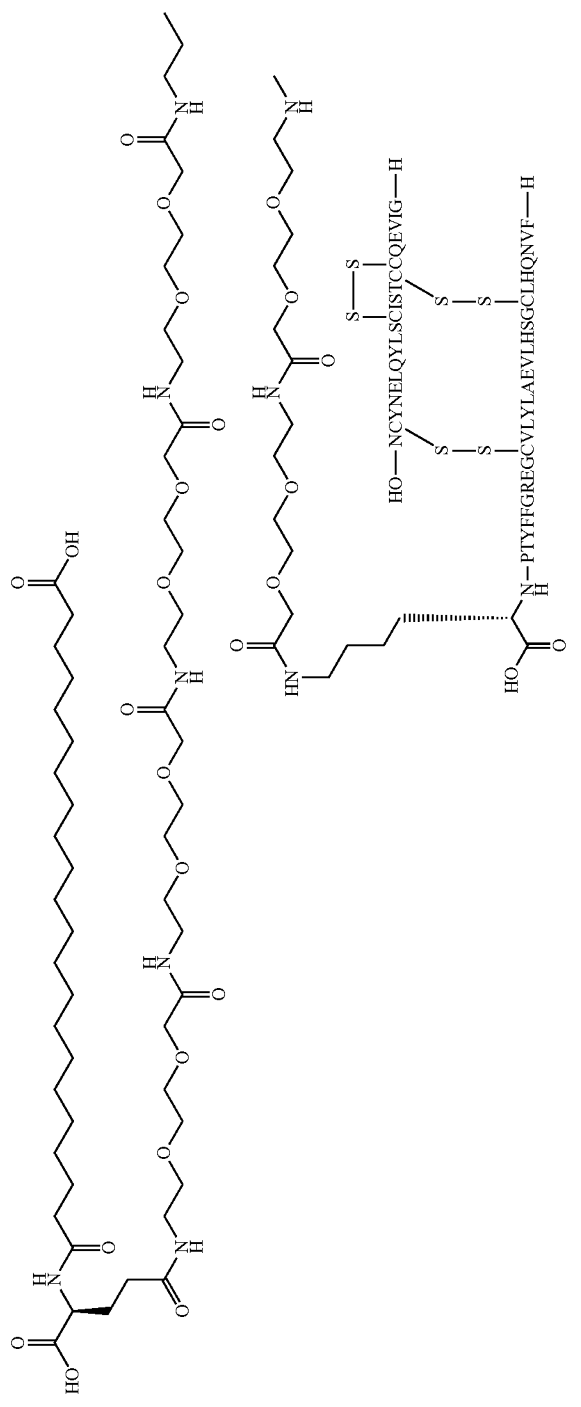
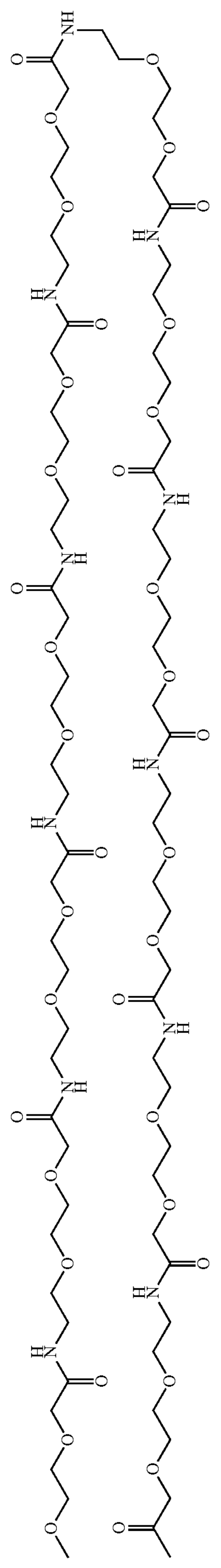

Compound A14E, B16H, B25H, B29K(N(ε)-docosanedioyl-γGlu-18×OEG), desB30 human insulin was prepared by procedures similar to those described in section 1 of Comparative Example 5.

LC-MS (ESI): m/z=1247.47[M+7H]$^{7+}$

The intermediate tert-butyl docosanedioyl-γGlu-(18×OEG-OSu)-OtBu was prepared by procedures similar to those described in section 2 of Comparative Example 5.

LC-MS (Sciex100 API): m/z=3320.83(M+1)$^{+}$

Example 30

A14E, B16H, B25H, B29K(N(ε)-docosanedioyl-γGlu-24×OEG), desB30 Human Insulin (Compound 17)

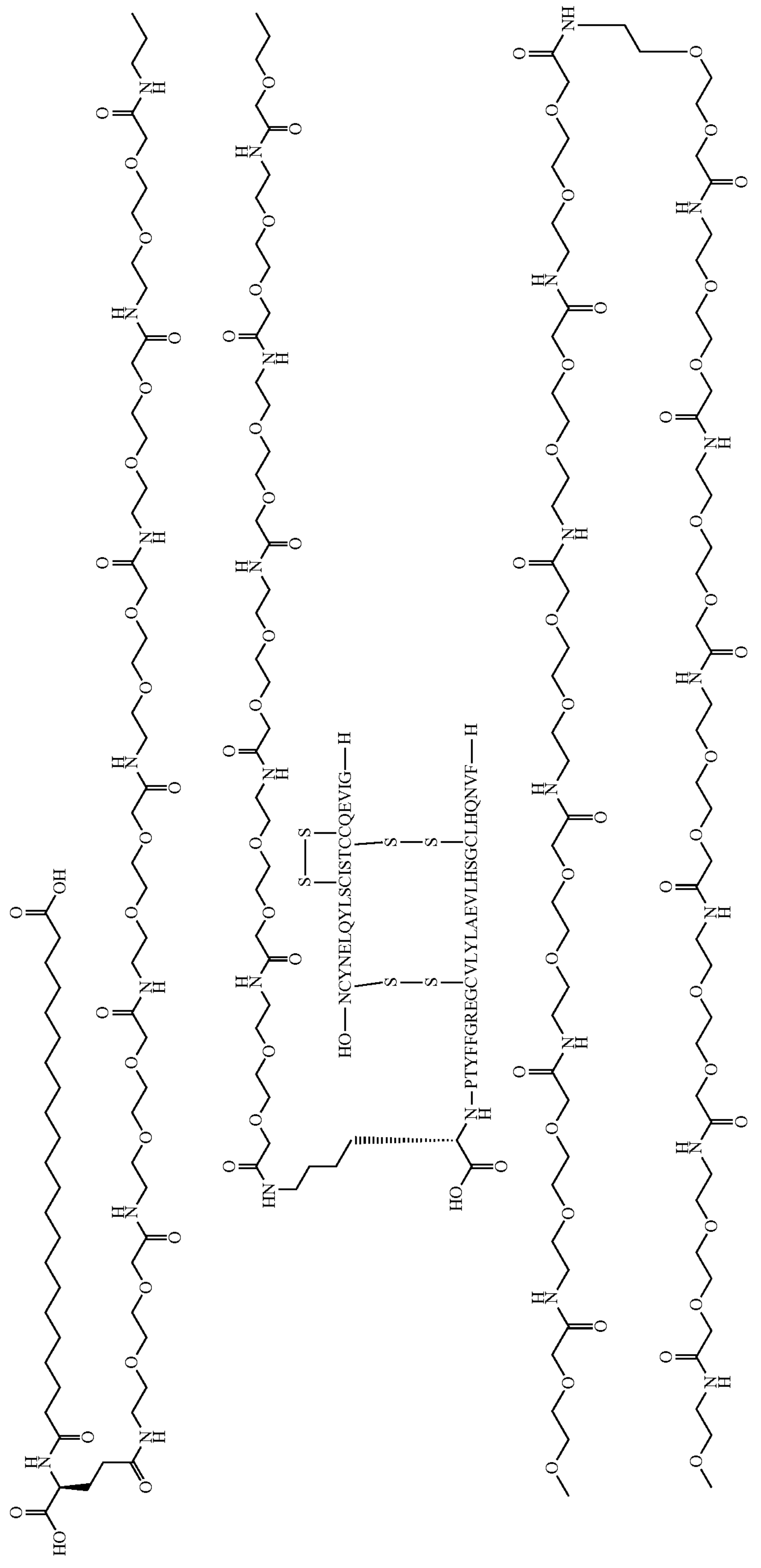

Compound A14E, B16H, B25H, B29K(N(ε)-docosanedioyl-γGlu-24×OEG), desB30 human insulin was prepared by procedures similar to those described in section 1 of Comparative Example 5.

LC-MS (ESI): m/z=873.35[M+11H]$^{11+}$

The intermediate tert-butyl docosanedioyl-γGlu-(24×OEG-OSu)-OtBu was prepared by procedures similar to those described in section 2 of Comparative Example 5.

LC-MS (Sciex100 API): m/z=4192.27(M+1)$^+$

Example 31

B29K(N(ε)-docosanedioyl-γGlu-OEG), desB30 Human Insulin (Compound 18)

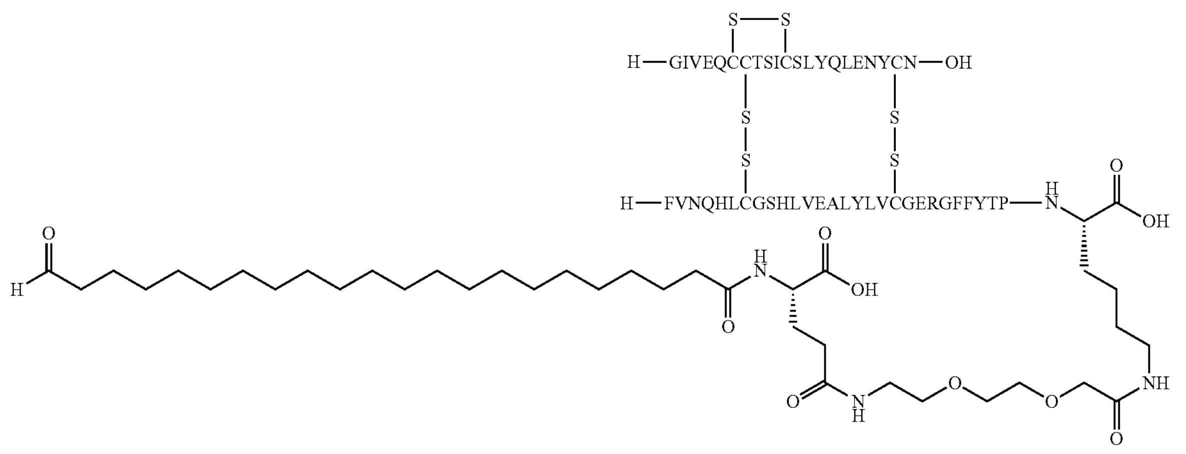

Compound B29K(N(ε)-docosanedioyl-γGlu-OEG), desB30 human insulin was prepared by procedures similar to those described in section 2 of Example 6.

LC-MS (ESI): m/z=1266.8122[M+5H]$^{5+}$

The intermediate tert-butyl docosanedioyl-γGlu-(OEG-OSu)-OtBu was prepared by procedures similar to those described in section 3 of Example 6.

LC-MS (Sciex100 API): m/z=854.57(M+1)$^+$

Example 32

B29K(N(ε)-docosanedioyl-γGlu-12×PEG), desB30 Human Insulin (Compound 19)

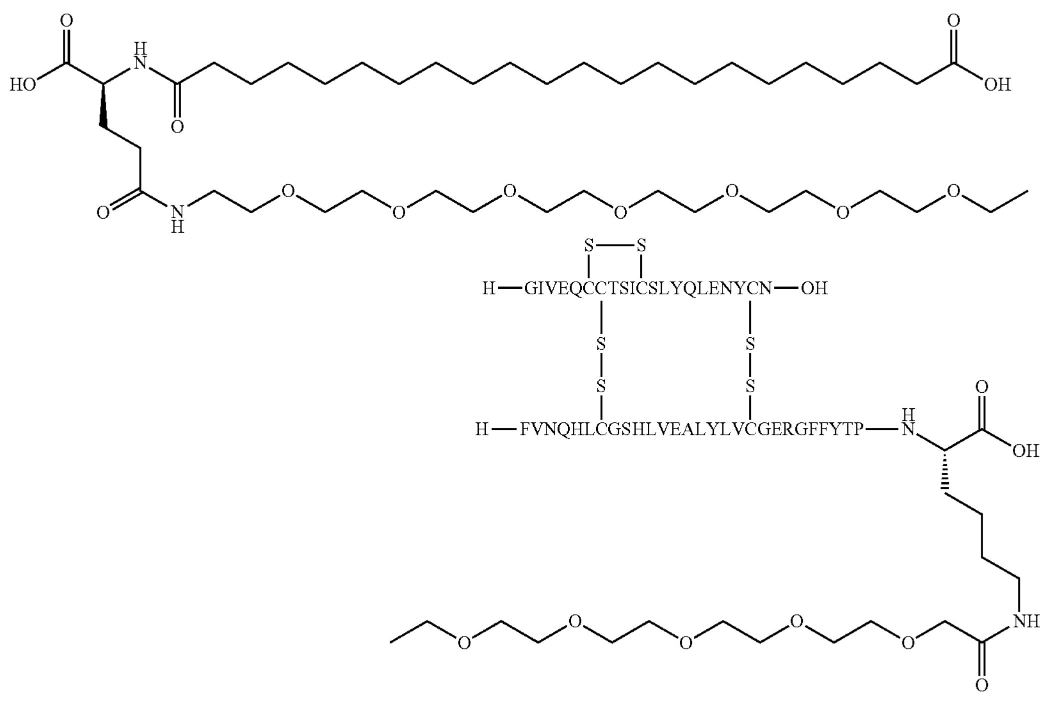

Compound B29K(N(ε)-docosanedioyl-γGlu-12×PEG), desB30 human insulin was prepared by procedures similar to those described in section 2 of Example 6.

LC-MS (ESI): m/z=1354.8667$[M+5H]^{5+}$

The intermediate tert-butyl docosanedioyl-γGlu-(12×PEG-OSu)-OtBu was prepared by procedures similar to those described in section 3 of Example 6.

LC-MS (Sciex100 API): m/z=1294.83$(M+1)^+$

The present invention has been illustrated by the above examples, but it should be understood that the above examples are for illustrative and descriptive purposes only and are not intended to limit the present invention to the scope of the described examples. Furthermore, it will be understood by those skilled in the art that the present invention is not limited to the examples described above, and that many variations and modifications can be made in accordance with the teachings of the present invention, all of which fall within the scope of the present invention as claimed. The protection scope of the present invention is defined by the appended claims and equivalents thereof.

The invention claimed is:

1. A compound of formula (B):

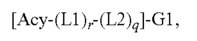

(B)

or a pharmaceutically acceptable salt, amide or ester thereof, wherein

G1 is a [Gly8, Arg34]GLP-1-(7-37) peptide of SEQ ID NO: 2;

[Acy-(L1)$_r$-(L2)$_q$] is a substituent linked to the ε amino group of the Lys residue at position 26 of the [Gly8, Arg34]GLP-1-(7-37) peptide;

r is 1;

q is 1 or 2;

Acy is a fatty diacid comprising 20, 21 or 22 carbon atoms, wherein formally, a hydroxyl group has been removed from one of the carboxyl groups in the fatty diacid;

L1 is the amino acid residue of γGlu;

L2 is-HN-$(CH_2)_2$-O-$(CH_2)_2$-O-$CH_2$-CO-;

Acy, L1 and L2 are linked by amide bonds; and the C-terminus of L2 is linked to the ε amino group of the Lys residue at position 26 of the [Gly8, Arg34] GLP-1-(7-37) peptide.

2. The compound according to claim 1, wherein, Acy is HOOC-$(CH_2)_{18}$-CO-, HOOC-$(CH_2)_{19}$-CO-, or HOOC-$(CH_2)_{20}$-CO-.

3. The compound according to claim 2, wherein, Acy is HOOC-$(CH_2)_{18}$-CO-, or HOOC-$(CH_2)_{20}$-CO-.

4. The compound according to claim 3, wherein the compound is selected from the group consisting of:

N-$\varepsilon^{26}$-[2-(2-[2-(2-[2-(2-[4-(19-carboxynonadecanoylamino)-4 (S)-carboxybutanoylamino]ethoxy)ethoxy]acetylamino)ethoxy]ethoxy) acetyl][Gly8, Arg34] GLP-1-(7-37) peptide;

N-ε[26]-[2-(2-[2-(4-[19-carboxynonadecanoylamino]-4 (S)-carboxybutanoylamino)ethoxy]ethoxy) acetyl] [Gly8, Arg34]GLP-1-(7-37) peptide; and N-ε[26]-[2-(2-[2-(2-[2-(2-[4-(21-carboxyheneicosanoylamino)-4 (S)-carboxybutanoylamino]ethoxy)ethoxy] acetylamino)ethoxy]ethoxy) acetyl][Gly8, Arg34] GLP-1-(7-37) peptide.

5. A pharmaceutical composition comprising the compound according to claim 1, and a pharmaceutically acceptable excipient.

6. A compound selected from the group consisting of:

N-ε[26]-[2-(2-[2-(4-[19-carboxynonadecanoylamino]-4 (S)-carboxybutanoylamino)ethoxy]ethoxy) acetyl] [Gly8, Arg34]GLP-1-(7-37) peptide; and N-ε[26]-[2-(2-[2-(2-[2-(2-[4-(21-carboxyheneicosanoylamino)-4 (S)-carboxybutanoylamino]ethoxy)ethoxy] acetylamino)ethoxy]ethoxy) acetyl][Gly8, Arg34] GLP-1-(7-37) peptide, or a pharmaceutically acceptable salt, amide or ester thereof.

7. A pharmaceutical composition comprising the compound according to claim 6, and a pharmaceutically acceptable excipient.

8. A compound having the structure:

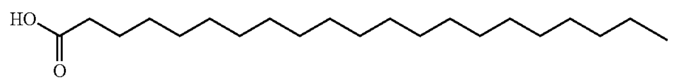

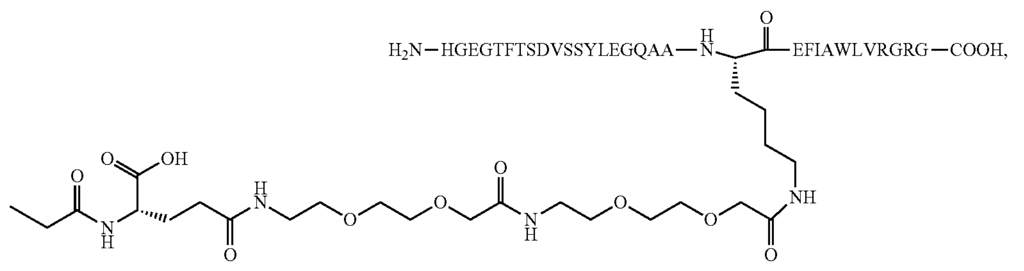

wherein the amino acid sequence in the compound is that of SEQ ID NO: 2.

9. A pharmaceutical composition comprising the compound according to claim 8, and a pharmaceutically acceptable excipient.

10. A compound having the structure:

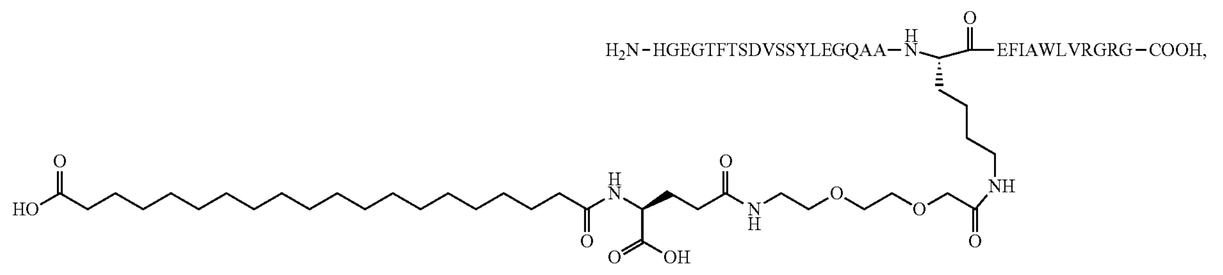

wherein the amino acid sequence in the compound is that of SEQ ID NO: 2.

11. A pharmaceutical composition comprising the compound according to claim 10, and a pharmaceutically acceptable excipient.

* * * * *